United States Patent
Jin et al.

(10) Patent No.: US 11,446,215 B2
(45) Date of Patent: Sep. 20, 2022

(54) MACROMONOMER BASED LIGHT-CURABLE DENTAL IMPRESSION MATERIAL

(71) Applicant: DENTSPLY SIRONA Inc., York, PA (US)

(72) Inventors: Xiaoming Jin, Middletown, DE (US); Yi Liu, Dover, DE (US); Stefano Gulmini, Rovigo (IT); Stefano Cavaliere, Solesino (IT); Zhaonan Zhang, Bear, DE (US)

(73) Assignee: DENTSPLY SIRONA INC., York, PA (US)

( * ) Notice: Subject to any disclaimer, the term of this patent is extended or adjusted under 35 U.S.C. 154(b) by 152 days.

(21) Appl. No.: 16/415,229

(22) Filed: May 17, 2019

(65) Prior Publication Data

US 2019/0350818 A1 Nov. 21, 2019

Related U.S. Application Data

(60) Provisional application No. 62/736,772, filed on Sep. 26, 2018, provisional application No. 62/673,187, filed on May 18, 2018.

(30) Foreign Application Priority Data

Oct. 1, 2018 (EP) ..................................... 18198048

(51) Int. Cl.
| | | |
|---|---|---|
| *A61K 6/90* | (2020.01) | |
| *C08F 283/12* | (2006.01) | |
| *C08G 77/20* | (2006.01) | |
| *C08G 77/26* | (2006.01) | |

(52) U.S. Cl.
CPC ............ *A61K 6/90* (2020.01); *C08F 283/124* (2013.01); *C08G 77/20* (2013.01); *C08G 77/26* (2013.01)

(58) Field of Classification Search
CPC .... A61K 6/62; A61K 6/70; A61K 6/90; C08F 283/124; C08G 77/20; C08G 77/26; C08G 77/248; C08G 77/46; C08L 83/10; C08L 83/12; C08L 83/06
USPC ............ 522/148, 172, 99; 523/107, 109–118
See application file for complete search history.

(56) References Cited

U.S. PATENT DOCUMENTS

| | | | | |
|---|---|---|---|---|
| 4,116,786 A | * | 9/1978 | Hodakowski | C08F 299/06 428/425.8 |
| 4,298,738 A | | 11/1981 | Lechtken | |
| 4,324,744 A | | 4/1982 | Lechtken | |
| 4,385,109 A | | 5/1983 | Lechtken | |
| 4,528,081 A | * | 7/1985 | Lien | C08G 77/20 522/39 |
| 4,543,398 A | * | 9/1985 | Bany | C08F 30/08 351/159.33 |
| 4,559,786 A | * | 12/1985 | Schuck | F01B 9/02 417/901 |
| 5,137,448 A | * | 8/1992 | Dougherty | C08L 83/06 433/214 |
| 5,426,131 A | * | 6/1995 | Katsamberis | C08J 7/0427 522/16 |
| 5,545,676 A | | 8/1996 | Palazzotto | |
| 5,849,812 A | | 12/1998 | Zech | |
| 6,180,741 B1 | * | 1/2001 | Yamaguchi | C08G 18/61 526/301 |
| 7,691,917 B2 | * | 4/2010 | Lai | C08G 18/672 523/106 |

FOREIGN PATENT DOCUMENTS

| | | |
|---|---|---|
| EP | 0173567 A2 | 3/1986 |
| EP | 3153150 A1 | 4/2017 |
| EP | 3231413 A1 | 10/2017 |

OTHER PUBLICATIONS

International Search Report; PCT/US2019/032825; Aug. 29, 2019 (completed); dated Sep. 11, 2019.
Written Opinion of the International Searching Authority; PCT/US2019/032825; Aug. 29, 2019 (completed); dated Sep. 11, 2019.
International Preliminary Report on Patentability; PCT/US2019/032825; Aug. 29, 2019 (completed); dated Sep. 11, 2019.
Jiye Cheng et al, "Synthesis and properties of photopolymerizable bifunctional polyether-modified polysiloxane polyurethane acrylate prepolymer", Journal of Adhesion Science and Technology,vol. 30, No. 1, 2016, p. 2-12.

* cited by examiner

*Primary Examiner* — Sanza L. McClendon
(74) *Attorney, Agent, or Firm* — Dentsply Sirona Inc.

(57) ABSTRACT

A light-curable dental impression material comprising
(a) a polymerizable polysiloxane resin composition comprising compounds of formula (I)

$$E\text{-}(L^1\text{-}Z)_n\text{-}L^2\text{-}E \qquad (I)$$

(b) a particulate filler; and
(c) a photoinitiator.

6 Claims, 6 Drawing Sheets

Note: All of the pastes listed in the FIGs. 5 and 6 were formulated with 15% wt/wt of filler mix and cured with LED curing pad. Tear strength was tested by using OLD test method (see the details in test method description).

MACROMONOMER BASED LIGHT-CURABLE DENTAL IMPRESSION MATERIAL

Field of the Invention

The present invention relates to a light-curable dental impression material. Moreover, the present invention relates to a use of the light-curable dental impression material of the present invention for the preparation of a dental impression.

BACKGROUND OF THE INVENTION

Dental impression materials are known. Dental impression materials are commonly available as reactive multi-component materials provided in packages including two compartments or two separate containers that keep the components isolated from each other during storage. Once the components are mixed, a chemical reaction is initiated that turns the mixed composition into a hardened mass during the setting time. Moreover, the working time and the setting time of conventional dental impression materials are limited and depend on the rate of the curing reaction. Therefore, storage stability of a dental impression material depends on the separation of reactive components and necessitates mixing prior to use which needs to be done chairside immediately prior to use so that the dental impression may be completed during the working time of usually only a few minutes.

Devices have been developed for the automatic mixing and dispensing of multi-component dental impression materials in order to provide high precision with regard to the homogeneity of the mixture, and the ratio of the two components to be mixed. Accordingly, the components of the dental impression material are simultaneously supplied from separate material chambers to a mixer during application of the dental impression material, which mixes and then dispenses a mixed paste. The paste may be supplied from the mixer directly onto a dental impression tray for immediate placement in a patient's mouth.

Once the material components have come into contact with each other in the mixing chamber, the mixture of the material in the mixing chamber can only be stored for a short time because the mixed material will soon set inside the mixing chamber unless dispensed and used. Therefore, the dental practitioner may have to remove and replace mixers several times each day.

Dental impression materials may be silicone impression material curable in an addition or condensation reaction whereby addition silicones are most popular. Although conventional addition silicone impression materials provide good detail reproduction, excellent dimensional stability, little shrinkage on set, addition silicones are inherently hydrophobic and as such require moisture control for optimal use. Finally, addition silicones have only a poor tear resistance.

Dental impression material based on cross-linking polysiloxanes are known. For example, U.S. Pat. No. 5,849,812 describes an addition-curing polyether dental impression material comprising (a) at least one polyether which has at least two optionally substituted vinyl and/or allyl end-groups, (b) an SiH component, (c) at least one platinum catalyst, (d) optional additives, and (e) organopolysiloxane with at least two alkenyl groups.

U.S. Pat. No. 5,137,448 discloses a dental impression composition that is polymerizable by having an initiator activated by actinic light within the visible light range of 360 to 600 nanometers, which contains a compound having at least two terminal acrylate unsaturations and an organosilicone containing backbone.

SUMMARY OF THE INVENTION

It is the problem of the present invention to provide a dental impression material which is highly tolerant to moisture, which has adjustable working and setting times, and which has excellent tear resistance while providing at the same time good detail reproduction without adhesion to core build-up materials or composite restorations, excellent dimensional stability, and reduced shrinkage on set, and which may be provided as a single composition which does not need mixing prior to use.

Moreover, it is the problem of the present invention to provide a use of the dental impression material of the present invention.

The present invention provides a light-curable dental impression material comprising:

(a) a polymerizable polysiloxane resin composition comprising compounds of the following formula (I):

$$\text{E-(L}^1\text{-Z)}_n\text{-L}^2\text{-E} \qquad (I)$$

wherein the E which may be the same or different, independently represent a monovalent group selected from a group containing a polymerizable carbon-carbon double bond, a group containing a polysiloxane moiety, a $C_{2\text{-}20}$ alkoxy group, a $C_{2\text{-}20}$ thioalkyl group, and a RNH group, wherein R is a $C_{2\text{-}20}$ alkyl group;

$L^1$ which may be the same or different when more than one $L^1$ is present, represents a divalent group of the following formula (II):

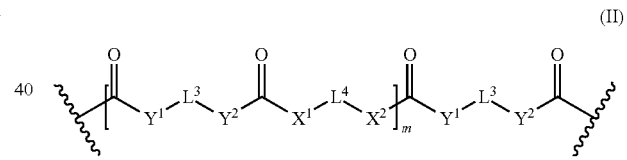

(II)

wherein $L^3$ which may be the same or different when more than one $L^3$ is present, independently represents a divalent linker group which may be substituted with up to four substituents of the formula (III):

$$-L^1\text{-E} \qquad (III)$$

wherein $L^1$ and E are as defined above;

$L^4$ which may be the same or different when more than one $L^4$ is present, independently represents a divalent linker group which may be substituted with up to four substituents of the formula (III), wherein $L^1$ and E are as defined above;

$X^1$, $X^2$, $Y^1$, and $Y^2$,
which may be the same or different, and when more than one $X^1$, $X^2$, $Y^1$, or $Y^2$, is present, the $X^1$, $X^2$, $Y^1$, and $Y^2$ may be the same or different, independently represent an oxygen atom, a sulfur atom and a group NR', wherein R' is a hydrogen atom or a $C_{1\text{-}4}$ alkyl group;

m represents 0 or an integer of from 1 to 40;

Z represents a divalent linker group which may additionally be substituted with up to four substituents selected from polysiloxane groups and groups of the formula (III), wherein $L^1$ and E are as defined above;

$L^2$ represents a single bond or a divalent group of the formula (II), wherein $L^3$, $L^4$, $X^1$, $X^2$, $Y^1$, $Y^2$ and m are independently as defined for $L^1$;

n represents 0 or an integer of from 1 to 4;

provided that a compound of formula (I) contains at least one monovalent group E having a polymerizable carbon-carbon double bond, a compound of formula (I) contains at least one polysiloxane group, and provided that when n is 0, then $L^2$ is a divalent group of the formula (II);

(b) a particulate filler; and (c) a photoinitiator.

When m is greater than 1, then $L^3$, $L^4$, $X^1$, $X^2$, $Y^1$ and $Y^2$ may each be independently the same or different as defined above such that the repeating unit

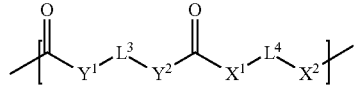

of the divalent group formula (II) may be same or different.

It is to be understood that the divalent group of formula (II) may include an oligomer or polymer chain of the same repeating unit or alternate oligomer or polymer chains of different repeating units and/or random polymer chains of different repeating units. Further, m of formula (II) may encompass i and j of specific embodiments of the compound of formula (I) as shown herein.

Further, the present invention provides a use of the light-curable dental impression material of the present invention for the preparation of a dental impression.

The present invention is based on the recognition that a specific composition of radically polymerizable polysiloxane compounds according to formula (I) may be used in a filled light-curable dental impression material given that such compounds contain at least one monovalent group E having a polymerizable carbon-carbon double bond, and at least one polysiloxane group so that the compounds have a low dynamic viscosity and may be cured in a radical polymerization reaction resulting in a cured material having limited adhesion to hard and soft tooth structure, core build-up materials or composite restorations.

The curing by radical polymerization allows to provide a convenient one component light-curable dental impression material which has high storage stability and which does not require mixing prior to use. Accordingly, the light-curable dental impression material may be provided as a ready-to-use dental tray. At the same time, the light-curable dental impression material provides, when cured, excellent tear resistance, good detail reproduction, excellent dimensional stability, and no shrinkage on set.

DETAILED DESCRIPTION OF THE PREFERRED EMBODIMENTS

Figure 1A:
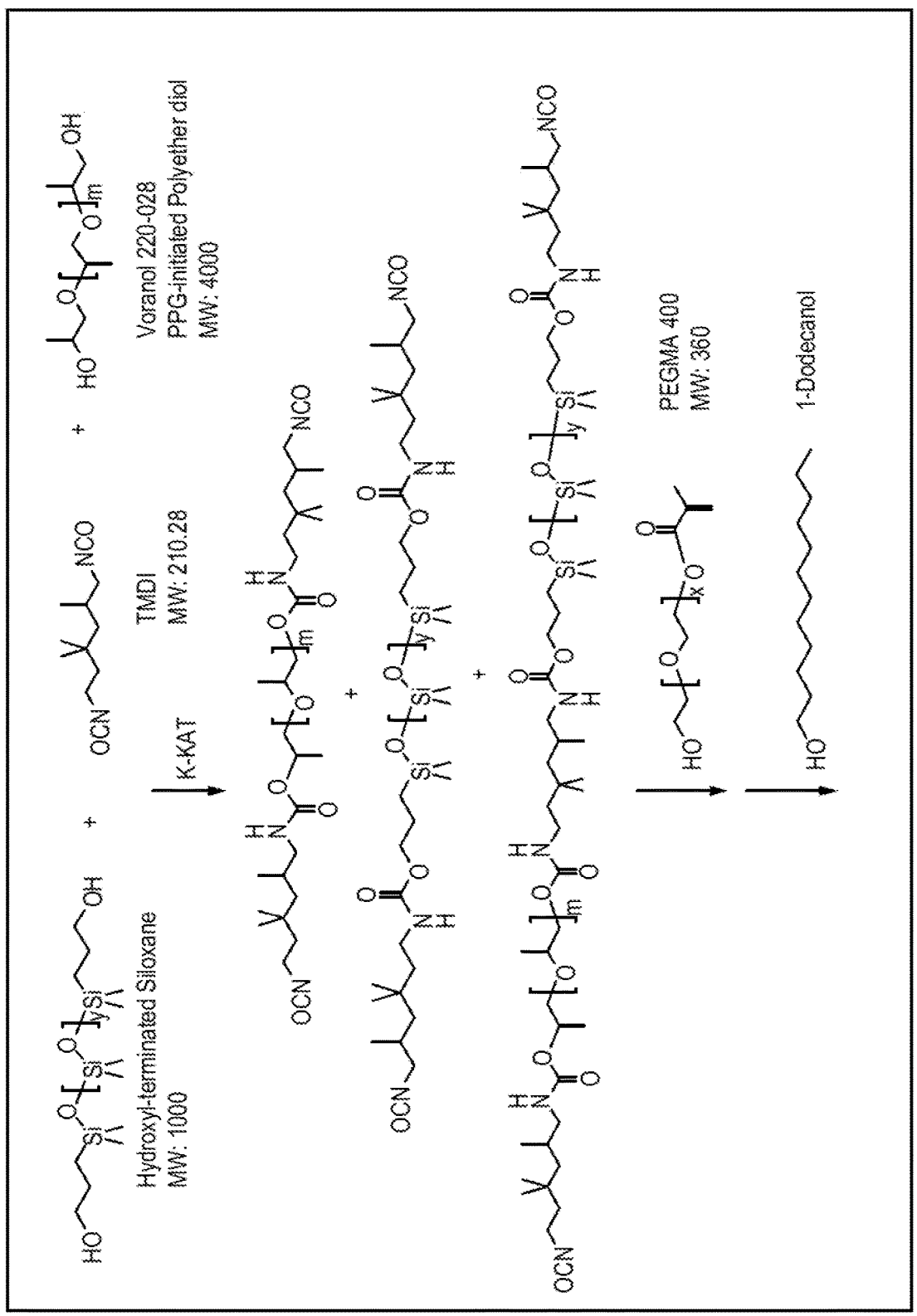
FIG. 1A and FIG. 1B shows a scheme of the synthesis procedure of compounds according to formula (I).

The terms "polymerization" and "polymerizable" relates to the combining or the capability to combine by covalent bonding of a large number of smaller molecules, such as monomers, to form larger molecules, that is, macromolecules or polymers. The monomers may be combined to form only linear macromolecules or they may be combined to form three-dimensional macromolecules, commonly referred to as crosslinked polymers. For example, monofunctional monomers form linear polymers, whereas monomers having at least two functional groups form crosslinked polymers also known as networks.

The term "$C_{2-20}$ alkylene group" according to the present invention represents a divalent $C_{2-20}$ hydrocarbon linker group. In particular, the linker group may be a hydrocarbon group which may be aliphatic and/or aromatic. Moreover, the linker group may be a straight-chain, branched and/or cyclic a hydrocarbon group. A $C_{2-20}$ hydrocarbon linker group may contain 1 to 8 heteroatoms selected from oxygen, nitrogen and sulphur, which divalent organic residue may be substituted with one or more substituents selected from the group consisting of a $C_{1-4}$ alkoxy groups, a hydroxyl group, a thiol group, and a $C_{6-14}$ aryl group. The $C_{2-20}$ alkylene group may be a linear or branched group. The hydrocarbon group may be substituted by 1 to 6 $C_{1-4}$ alkyl groups. Specific examples of the alkyl groups are methylene, ethylene, n-propylene, i-propylene, n-butylene, i-butylene or tert.-butylene. In a preferred embodiment, the hydrocarbon group may contain 1 to 5 oxygen atoms in the hydrocarbon group in the form of aliphatic or aromatic ether bonds, keto groups, carboxylic acid groups, or hydroxyl groups. In case of an aliphatic group, the $C_{2-20}$ alkylene group may be a straight chain or branched alkylene group or a cycloalkylene group. In case of an aromatic group, the $C_{2-20}$ alkylene group may be an arylene group or a $C_{3-14}$ heteroarylene group. Specifically, it may be a divalent substituted or unsubstituted $C_{2-20}$ alkylene group, substituted or unsubstituted $C_{6-14}$ arylene group, substituted or unsubstituted $C_{3-20}$ cycloalkylene group, substituted or unsubstituted $C_{7-20}$ arylenealkylenearylene group. Furthermore, the $C_{2-20}$ alkylene group represents a saturated aliphatic $C_{2-20}$ hydrocarbon chain which may contain 2 to 4 oxygen atoms or nitrogen atoms, and which may be substituted by 1 to 6 $C_{1-4}$ alkyl groups, or the $C_{2-20}$ alkylene group may be a substituted or unsubstituted $C_{7-20}$ arylenealkylenearylene group which may be substituted by 1 to 6 $C_{1-4}$ alkyl groups.

"Actinic radiation" is any electromagnetic radiation that is capable of producing photochemical action and can have a wavelength of at least 150 nm and up to and including 1250 nm, and typically at least 300 nm and up to and including 750 nm.

The term "electron donor" as used herein means a compound capable of contributing electrons in a photochemical process. Suitable examples include organic compounds having heteroatoms with electron lone pairs, for example amine compounds.

The present invention provides a light-curable dental impression material. The light-curable dental impression material is preferably a one-pack composition packaged in a syringe or provided on a ready-to-use dental impression tray. Alternatively, the light-curable dental impression material of the present invention may also be a two-pack composition, in particular when formulated as a dual cure composition containing an additional redox initiator system.

When packaged in a syringe or provided on a ready-to-use dental impression tray, the composition must be shielded from actinic light during storage.

The light-curable dental impression material of the present invention comprises a polymerizable polysiloxane resin composition comprising compounds of the formula (I) having a polymerizable moiety in combination with a polysiloxane moiety. The polymerizable polysiloxane resin composition comprises compounds of the formula (I) which are macromonomers. The macromonomers may be obtained by reacting a first reactant and a second reactant in a specific stoichiometric ratio so that an excess with regard to the molar amount of reactive groups of the second reactant is present, and using a third reactant in a specific ratio to end-cap any excess reactive end-groups.

The reaction of the first reactant and the second reactant is preferably an addition polymerization. However, a polycondensation is also possible.

The end-capping reaction of the third reactant with excess functional groups of the second reactant is preferably also an addition polymerization. However, a polycondensation is again possible.

In case of a polyaddition reaction, the formation of a urethane bond is preferred. Alternatively, the formation of urea or S-thiocarbamate linkages by the reaction of the first and second reactants is also possible. Accordingly, the first reactant may be a diol, or alternatively a diamine or a dithiol, and the second reactant may be a diisocyanate.

Figure 1B:
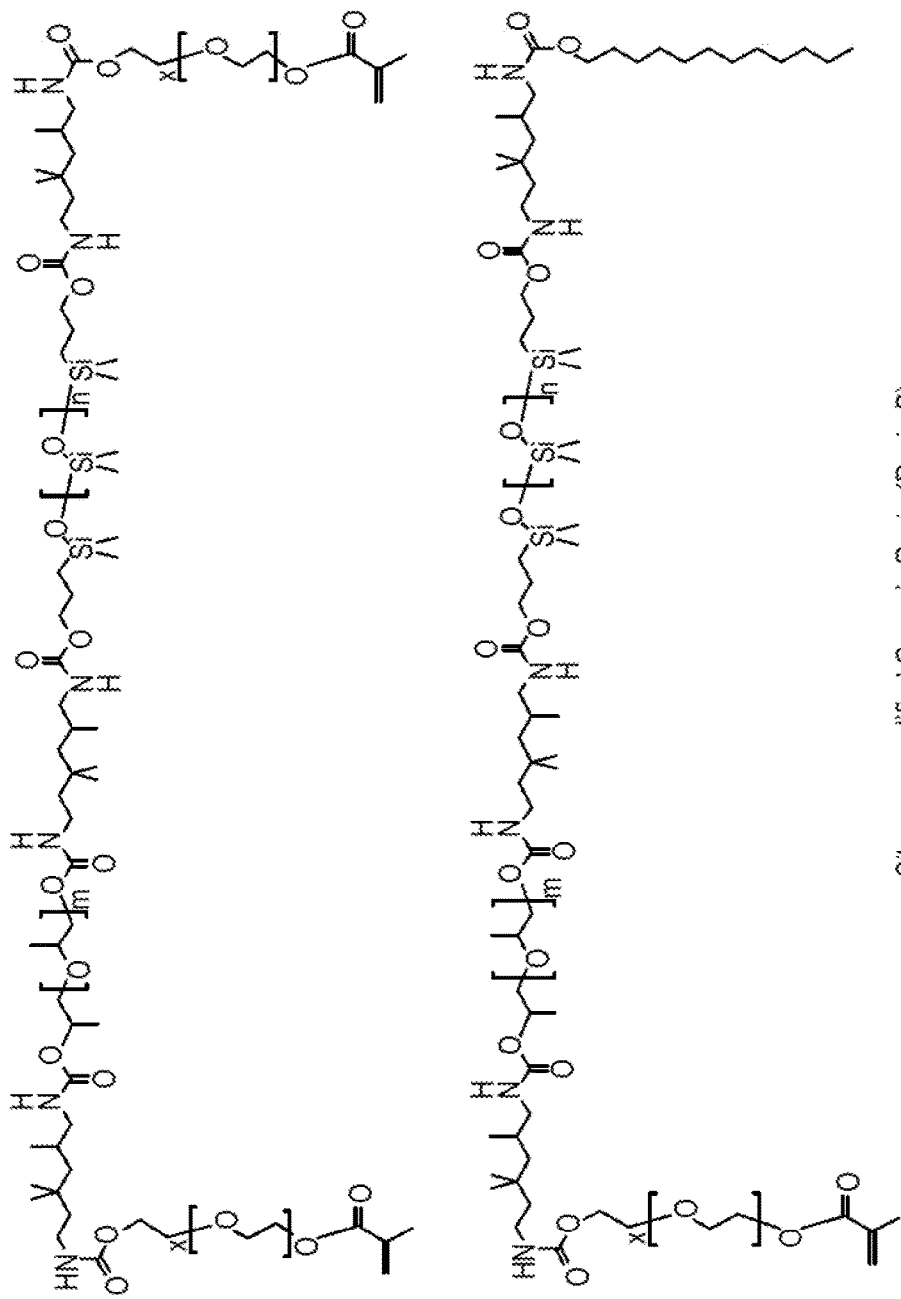

In case of polyfunctional reactants such as trifunctional reactants, branching may be introduced into the macromonomer. According to the present invention, it is possible to use a di- or polyalcohol as the first reactant and a di- or polyisocyanate as the second reactant whereby an isocyanate-terminated polyurethane prepolymer is formed which is endcapped with a monofunctional third reactant such as an alcohol as shown in FIG. 1A and FIG. 1B. Alternatively, the use a di- or polyamine or di- or polythiol as the first reactant and a di- or polyisocyanate as the second reactant results in an isocyanate-terminated urea or S-carbamate prepolymer which is endcapped with a monofunctional third reactant such as an alcohol, amine or thiol compound.

However, according to the present invention, it is also possible to use a di- or polyisocyanate as the first reactant and a di- or polyalcohol as the second reactant whereby a hydroxyl-terminated prepolymer is formed which is end-capped with a monofunctional third reactant such as an isocyanate. Alternatively, it is possible to use a di-or polyisocyanate as the first reactant and a di- or polyamine or di- or polythiol as the second reactant whereby an amine or thiol-terminated prepolymer is formed which is end-capped with a monofunctional third reactant such as an isocyanate.

The first, second and third reactants may be mixtures of two or more different compounds. Any of the first, second and third reactants may contain one or more polysiloxane moieties. Preferably, the third component introduces a radical polymerizable moiety into the macromonomer.

According to a preferred embodiment, the light-curable dental impression material of the present invention further comprises additional polymerizable compounds, notably compounds which are compounds of formula (I), but lack any polysiloxane moiety. Specifically, the light-curable dental impression material of the present invention preferably comprises additional polymerizable macromonomers. The polymerizable macromonomers may be obtained by reacting a fourth reactant and a fifth reactant in a specific stoichiometric ratio so that an excess with regard to the molar amount of reactive groups of the fifth reactant is present, and using a sixth reactant in a specific ratio to end-cap any excess reactive end-groups.

The reaction of the fourth reactant and the fifth reactant is preferably an addition polymerization. However, a polycondensation is also possible. The end-capping reaction of the sixth reactant with excess functional groups of the fifth reactant is preferably also an addition polymerization. However, a polycondensation is again possible.

In case of a polyaddition reaction, the formation of a urethane bond is preferred. Alternatively, the formation of urea or S-thiocarbamate linkages by the reaction of the fourth and fifth reactants is also possible. Accordingly, the fourth reactant may be a diol, or alternatively a diamine or a dithiol, and the second reactant may be a diisocyanate.

Figure 2:
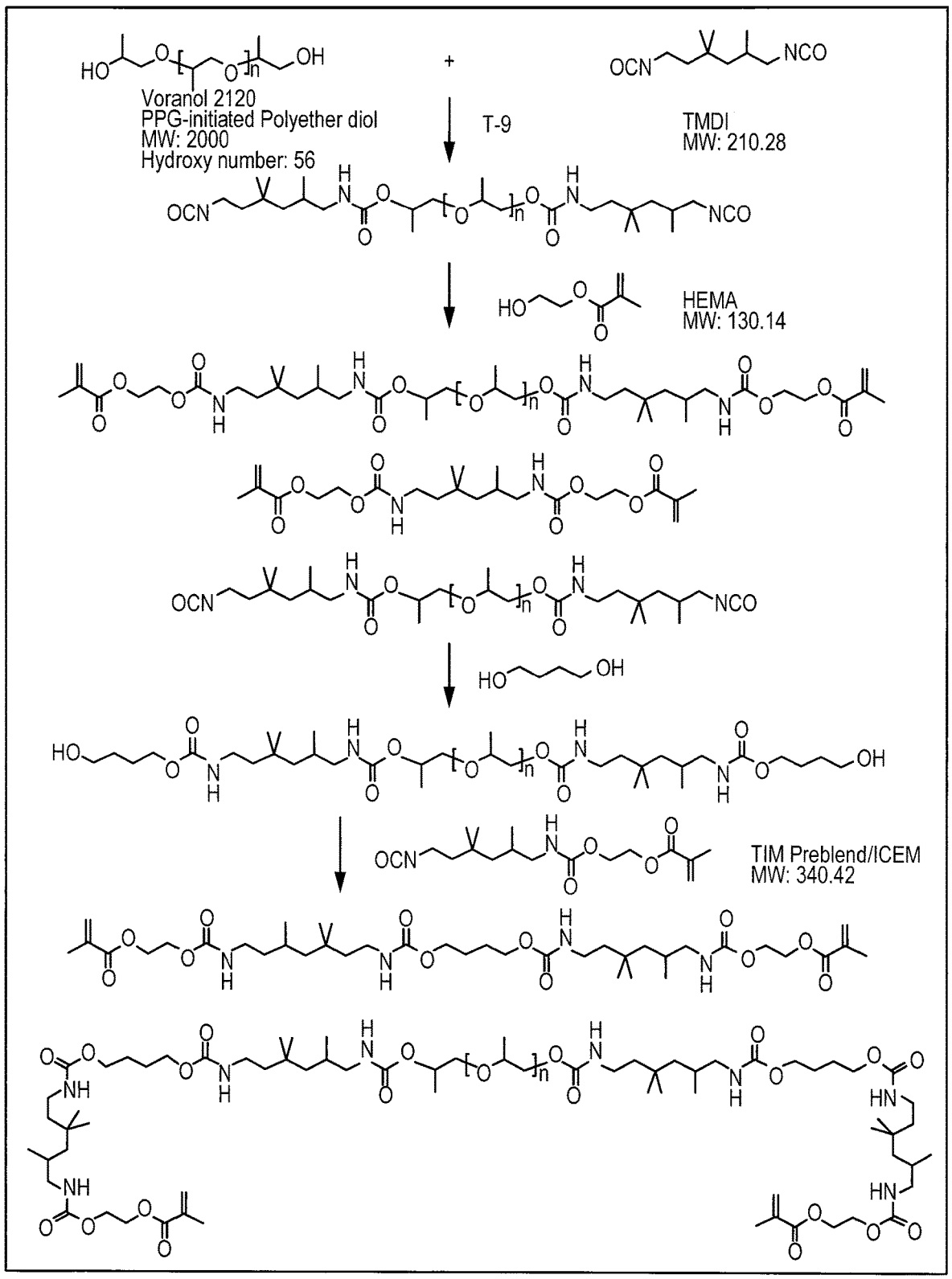
FIG. 2 shows a scheme of the synthesis procedure of macromonomers which may be used in combination with the compounds according to formula (I).

In case of polyfunctional reactants, branching may be introduced into the macromonomer. According to the present invention, it is possible to use a di- or polyalcohol as the fourth reactant and a di- or polyisocyanate as the fifth reactant whereby an isocyanate-terminated prepolymer is formed which is endcapped with a monofunctional sixth reactant such as an alcohol as shown in FIG. 2. Alternatively, the use a di- or polyamine or di- or polythiol as the fourth reactant and a di- or polyisocyanate as the fifth reactant results in an isocyanate-terminated urea or S-carbamate prepolymer which is endcapped with a monofunctional third reactant such as an alcohol, amine or thiol compound.

However, according to the present invention, it is also possible to use a di -or polyisocyanate as the fourth reactant and a di- or polyalcohol as the fifth reactant whereby a hydroxyl-terminated polyurethane prepolymer is formed which is end-capped with a monofunctional sixth reactant such as an isocyanate. Alternatively, it is possible to use a di- or polyisocyanate as the fourth reactant and a di- or polyamine or di- or polythiol as the second reactant whereby an amine or thiol-terminated polyurea or poly-S-thiocarbamate prepolymer is formed which is end-capped with a monofunctional third reactant such as an isocyanate.

The fourth, fifth and sixth reactants may be mixtures of two or more different compounds. None of the first, second and third reactants may contain any polysiloxane moiety in case of the additional polymerizable macromonomers. Reactants which do not contain any polysiloxane moiety used for preparing a polymerizable polysiloxane resin composition comprising compounds of the formula (I) may be used for preparing the additional polymerizable macromonomers. Preferably, the sixth component introduces a radical polymerizable moiety into the additional polymerizable macromonomer.

The Polymerizable Polysiloxane Resin Composition

The light-curable dental impression material of the present invention comprises a polymerizable polysiloxane resin composition comprising compounds of the following formula (I):

$$E\text{-}(L^1\text{-}Z)_n\text{-}L^2\text{-}E \qquad (I)$$

According to a preferred embodiment, the polymerizable polysiloxane resin composition has a total siloxane content in a range of from 10 to 40% wt/wt, more preferably in a range of from 15 to 35% wt/wt. The total siloxane content of the polymerizable polysiloxane resin composition may be determined by $^{29}$Si-NMR.

In a compound of formula (I), E which may be the same or different, independently represent a monovalent group selected from a group containing a polymerizable carbon-carbon double bond, a group containing a polysiloxane moiety, a $C_{2-20}$ alkoxy group, a $C_{2-20}$ thioalkyl group, and a RNH group, wherein R is a $C_{2-20}$ alkyl group.

According to a preferred embodiment, E is a group containing a polymerizable carbon-carbon double bond, preferably a (meth)acryloyl group, a (meth)acrylamide group or an allyl (meth)acrylamide group, more preferably a (meth)acryloyl group.

According to preferred embodiment, the monovalent groups E contain (meth)acrylate groups so that the total (meth)acrylate content of the polymerizable polysiloxane resin composition is in a range of from 0.20 to 0.50 mmol/g, more preferably from 0.25 to 0.45 mmol/g. The total (meth)acrylate content of the polymerizable polysiloxane resin composition is determined by using $^1$H-NMR.

According to a preferred embodiment, E is a group according to the following formula (IV):

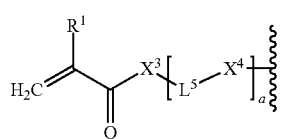

(IV)

wherein

R$^1$ represents a hydrogen atom or a $C_{1-12}$ alkyl group;

X$^3$ represents an oxygen atom, a sulfur atom or a group NR$^2$, wherein R$^2$ is a hydrogen atom, $C_{1-12}$ alkyl group, or an allyl group;

L$^5$ is a divalent hydrocarbon linker group or polysiloxane containing linker group, preferably a $C_{2-20}$ alkylene group;

X$^4$ represents an oxygen atom, a sulfur atom or a group NR$^3$, wherein R$^3$ is a hydrogen atom, or a $C_{1-12}$ alkyl group; and a represents an integer of from 1 to 20.

Preferably, R$^1$ represents a $C_{1-4}$ alkyl group, more preferably a methyl group.

According to a first embodiment, X$^3$ preferably represents an oxygen atom or a sulfur atom, more preferably an oxygen atom. According to a second embodiment, X$^3$ preferably represents a group NR$^2$, wherein R$^2$ is a hydrogen atom, $C_{1-12}$ alkyl group, or an allyl group.

Preferably, X$^4$ represents an oxygen atom or a sulfur atom, more preferably an oxygen atom.

L$^5$ is a divalent hydrocarbon linker group or polysiloxane containing linker group. A polysiloxane containing linker group may be a polysiloxane group or contain one or more hydrocarbon fragments in the main chain. Preferably, L$^5$ is a linear or branched $C_{2-3}$ alkylene group.

According to a preferred embodiment, the group -[L$^5$-X$^4$]— is selected from the following groups:

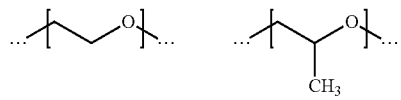

Preferably, a is an integer of from 1 to 10.

According to a preferred embodiment, E is a polysiloxane group of the following formula (V):

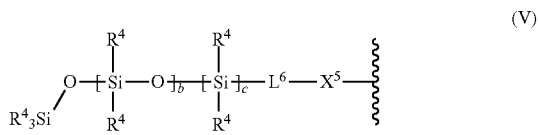

(V)

wherein

R$^4$ which may be the same or different, independently represent a straight-chain, branched or cyclic alkyl group;

L$^6$ is a divalent hydrocarbon linker group, preferably a $C_{2-20}$ alkylene group;

X$^5$ represents an oxygen atom, a sulfur atom or a group NR$^5$, wherein R$^5$ is a hydrogen atom, or a $C_{1-12}$ alkyl group;

b is 0 or an integer of from 1 to 1000; and c is 0 or 1.

According to a preferred embodiment, R$^4$ is a straight chain, optionally substituted $C_{1-12}$ alkyl group, preferably it is a straight chain optionally substituted $C_{1-6}$ alkyl group.

According to a preferred embodiment, R$^4$ is a branched, optionally substituted $C_{1-12}$ alkyl group, preferably it is a branched, optionally substituted $C_{1-6}$ alkyl group.

According to a preferred embodiment, R$^4$ is a cyclic, optionally substituted $C_{1-12}$ alkyl group, preferably it is a cyclic, optionally substituted $C_{1-6}$ alkyl group.

More preferably, R$^4$ is a methyl group.

Preferably, X$^5$ represents an oxygen atom or a sulfur atom, more preferably an oxygen atom.

Preferably, b is an integer of from 1 to 1000, more preferable it is an integer of from 1 to 100, and even more preferably it is an integer of from 1 to 10.

Preferably, c is 1.

According to a preferred embodiment, E is a linear optionally substituted $C_{2-20}$ alkoxy group.

According to a preferred embodiment, E is a branched optionally substituted $C_{2-20}$ alkoxy group.

Preferably, E is a linear optionally substituted $C_{2-15}$ alkoxy group, more preferably it is a linear unsubstituted $C_{2-15}$ alkoxy group, and even more preferably it is a linear unsubstituted $C_{12}$ alkoxy group.

According to a preferred embodiment, E is a linear optionally substituted $C_{2-20}$ thioalkyl group.

According to a preferred embodiment, E is a branched optionally substituted $C_{2-20}$ thioalkyl group.

Preferably, E is a linear optionally substituted $C_{2-15}$ thioalkyl group, more preferably it is a linear unsubstituted $C_{2-15}$ thioalkyl group.

According to a preferred embodiment, E is a RNH group, wherein R is a $C_{2-20}$ alkyl group.

Preferably, R is a linear optionally substituted $C_{2-20}$ alkyl group.

Preferably, R is a branched optionally substituted $C_{2-20}$ alkyl group.

Preferably, R is a linear optionally substituted $C_{2-15}$ alkyl group, more preferably it is a linear unsubstituted $C_{2-15}$ alkyl group, and even more preferably it is a linear unsubstituted $C_{2-6}$ alkyl group.

In a compound of formula (I), $L^1$ represents a divalent group of the following formula (II):

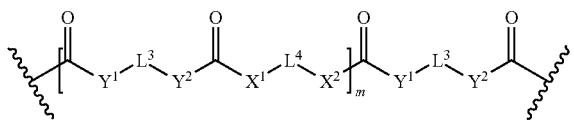
(II)

wherein $L^3$ which may be the same or different when more than one $L^3$ is present, independently represents a divalent linker group which may be substituted with up to four substituents of the formula (III):

-$L^1$-E    (III)

wherein $L^1$ and E are as defined above;

$L^4$ which may be the same or different when more than one $L^4$ is present, independently represents a divalent linker group which may be substituted with up to four substituents of the formula (III), wherein $L^1$ and E are as defined above;

$X^1$, $X^2$, $Y^1$, and $Y^2$,
which may be the same or different, and when more than one $X^1$, $X^2$, $Y^1$, or $Y^2$, is present, the $X^1$, $X^2$, $Y^1$, and $Y^2$ may be the same or different, independently represent an oxygen atom, a sulfur atom and a group NR', wherein R' is a hydrogen atom or a $C_{1-4}$ alkyl group;

m represents 0 or an integer of from 1 to 40.

When m is greater than 1, then $L^3$, $L^4$, $X^1$, $X^2$, $Y^1$ and $Y^2$ may each be independently the same or different as defined above such that the repeating unit

of the divalent group formula (II) may be same or different.

It is to be understood that the divalent group of formula (II) may include an oligomer or polymer chain of the same repeating unit or alternate oligomer or polymer chains of different repeating units and/or random polymer chains of different repeating units. Further, m of formula (II) may encompass i and j of specific embodiments of the compound of formula (I) as shown herein.

According to a preferred embodiment, $L^3$ represents a $C_{2-20}$ alkylene group as defined above which may contain up to 10 heteroatoms in the main chain, which are selected from oxygen, sulfur or $NR^\#$, wherein $R^\#$ represents a hydrogen atom or a straight chain, branched or cyclic $C_{1-6}$ alkyl group.

According to a preferred embodiment, $L^3$ represents a group according to the following formula (VI):

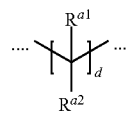
(VI)

wherein
$R^{a1}$ and $R^{a2}$
which may be the same or different, independently represent a hydrogen atom, a $C_{1-6}$ linear or branched alkyl group, a $C_{4-10}$ aryl group, a polymerizable double bond containing organic residue, preferably a (meth)acrylate group containing organic residue, a group of the following formula $[-X''L'']_m R^{a3}$, wherein X'' represents O, S, or $NR^{a4}$ wherein $R^{a4}$ represents a hydrogen atom, an organic residue containing a polymerizable double bond, preferably an organic residue containing a (meth)acrylate group, a linear or branched $C_{1-6}$ alkyl group, or a $C_{4-10}$ aryl group, L'' represents a $C_{1-6}$ linear or branched alkyl group, a $C_{4-10}$ aryl group, or a $SiR^{a5}_2$ group wherein $R^{a5}$ which may be the same or different, independently represent an organic residue containing a polymerizable double bond, preferably an organic residue containing a (meth)acrylate group, or a $C_{1-4}$ alkyl group, preferably a methyl group, m is an integer from 1 to 20, and $R^{a3}$ is an organic residue containing a polymerizable double bond, preferably an organic residue containing a (meth)acrylate group, a $C_{1-4}$ alkyl group, or a $C_{4-10}$ aryl group, and $R^{a1}$ and $R^{a2}$ may comprise a group of the formula (III);

d is an integer of from 1 to 20, preferably an integer of from 1 to 10, and more preferably d is 6.

Preferably, $L^3$ is selected from the following groups:

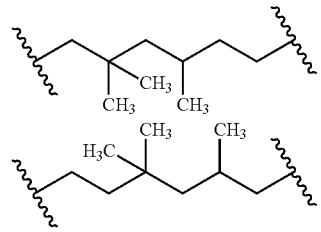

According to a preferred embodiment, $L^3$ represents a group according to the following formula (VII):

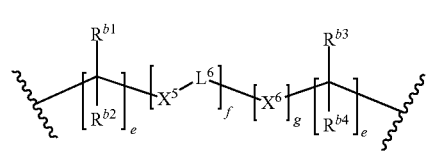
(VII)

wherein
$R^{b1}$, $R^{b2}$, $R^{b3}$ and $Rb^4$
which may be the same or different, independently represent a hydrogen atom, a $C_{1-6}$ linear or branched alkyl group, a $C_{4-10}$ aryl group, a polymerizable double bond containing organic residue, preferably a (meth)acrylate group containing organic residue, a group of the following formula $[-X'''L''']_m R^{b5}$, wherein X''' represents O, S, or $NR^{b6}$ wherein $R^{b6}$ represents a hydrogen atom, an organic residue containing a polymerizable double bond, preferably an organic residue containing a (meth)acrylate group, a linear or branched $C_{1-6}$ alkyl group, or a $C_{4-10}$ aryl group, L''' represents a $C_{1-6}$ linear or branched alkyl group, a $C_{4-10}$ aryl group, or a $SiR^{b7}{}_2$ group wherein $R^{b7}$ which may be the same or different, independently represent an organic residue containing a polymerizable double bond, preferably an organic residue containing a (meth)acrylate group, or a $C_{1-4}$ alkyl group, preferably a methyl group, m is an integer from 1 to 20, and $R^{b5}$ is an organic residue containing a polymerizable double bond, preferably an organic residue containing a (meth)acrylate group, a $C_{1-4}$ alkyl group, or a $C_{4-10}$ aryl group, and $R^{b1}$, $R^{b2}$, $R^{b3}$, and $R^{b4}$ may comprise a group of the formula (III);

$X^5$ and $X^6$
which may be the same or different, and when more than one $X^5$ or $X^6$, are present, the $X^5$ and $X^6$ may be the same or different, independently represent an oxygen atom, a sulfur atom and a group $NR^N$, wherein $R^N$ is a hydrogen atom or a $C_{1-4}$ alkyl group;

$L^6$
is a divalent hydrocarbon linker group, preferably a $C_{2-20}$ alkylene group;

e
is an integer of from 1 to 10;

f
is an integer of from 1 to 100; specifically 1 to 40 or 40 to 100 and g
is 0 or 1.

Preferably, $L^6$ is a linear or branched $C_{2-3}$ alkylene group.

According to a preferred embodiment, the group -[$L^6$-$X^5$]— is selected from the following groups:

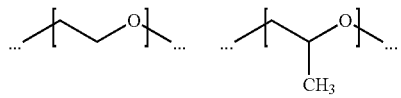

According to a preferred embodiment, $L^3$ represents a group according to the following formula (VIII):

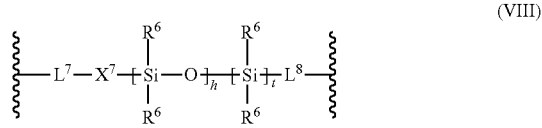

wherein
$R^6$
which may be the same or different, independently represent a straight-chain, branched or cyclic alkyl group;

$X^7$
represent an oxygen atom, a sulfur atom and a group $NR^{N1}$, wherein $R^{N1}$ is a hydrogen atom or a $C_{1-4}$ alkyl group;

$L^7$ and $L^8$
is a divalent hydrocarbon linker group, preferably a $C_{2-20}$ alkylene group;

h
is 0 or an integer of from 1 to 1000;

t
is 0 or 1.

$L^3$ may also be a polysiloxane group of the following formula (VIIIa), (VIIIb), or (VIIIc)

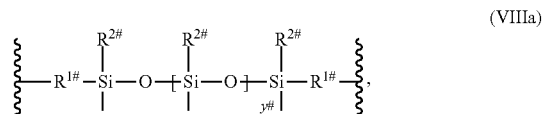

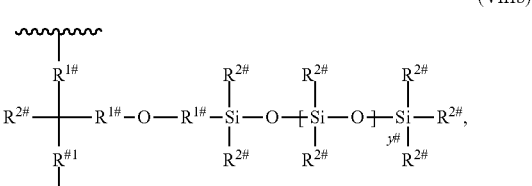

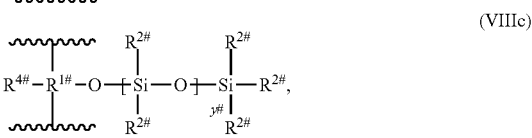

wherein
$R^{1\#}$ is an alkylene having 1 to 8 carbon atoms;
$R^{2\#}$ is an alkyl having from 1 to 4 carbon atoms;
$R^{4\#}$ is an alkyl, alkoxy or a cycloalkyl group;
$y^\#$ is an integer from 5 to 20.

According to a preferred embodiment, $R^6$ is a straight chain, optionally substituted $C_{1-12}$ alkyl group, preferably it is a straight chain optionally substituted $C_{1-6}$ alkyl group.

According to a preferred embodiment, $R^6$ is a branched, optionally substituted $C_{1-12}$ alkyl group, preferably it is a branched, optionally substituted $C_{1-6}$ alkyl group.

According to a preferred embodiment, $R^6$ is a cyclic, optionally substituted $C_{1-12}$ alkyl group, preferably it is a cyclic, optionally substituted $C_{1-6}$ alkyl group.

More preferably, $R^6$ is a methyl group.

Preferably, $X^7$ represents an oxygen atom.

Preferably, $L^7$ and $L^8$ which may be the same or different, independently represent a linear or branched $C_{2-3}$ alkylene group.

More preferably, $L^7$ and $L^8$ which may be the same or different, independently are selected from the following groups:

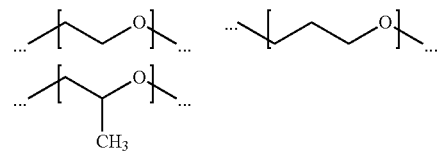

h is an integer of from 1 to 40, preferably, h is an integer of from 1 to 20, more preferably it is an integer of from 1 to 10.

Preferably, t is 1.

According to a preferred embodiment, $L^4$ may represent any group as defined according to $L^3$.

According to a preferred embodiment, $L^4$ represents a group according to the following formula (IX):

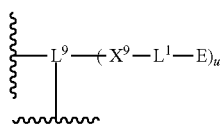 (IX)

wherein
E and $L^1$ are defined as above;
$L^9$ is a divalent hydrocarbon linker group, preferably a $C_{2-20}$ alkylene group;
$X^9$ when more than one $X^9$ is present the $X^9$ groups may be the same or different, independently represent an oxygen atom, a sulfur atom and a group $NR^{N2}$, wherein $R^{N2}$ is a hydrogen atom or a $C_{1-4}$ alkyl group;
u is an integer of from 1 to 4.

Preferably, $X^9$ is an oxygen atom or a sulfur atom, more preferably it is an oxygen atom.

Preferably, u is 1 or 2, more preferably it is 2.

According to a preferred embodiment, the group according to formula (IX) is selected from the following groups:

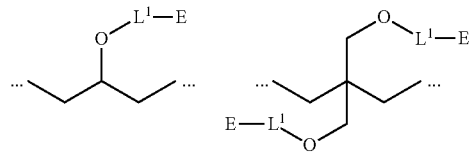

In a group of formula (II), $X^1$ and $X^2$ which may be the same or different, and when more than one $X^1$, and $X^2$ is present, the $X^1$, and $X^2$ may be the same or different, independently represent an oxygen atom, a sulfur atom and a group NR', wherein R' is a hydrogen atom or a $C_{1-4}$ alkyl group. Preferably, $X^1$ and $X^2$ represent an oxygen atom.

In a group of formula (II), $Y^1$ and $Y^2$ which may be the same or different, and when more than one $Y^1$, and $Y^2$ is present, the $Y^1$, and $Y^2$ may be the same or different, independently represent an oxygen atom, a sulfur atom and a group NR', wherein R' is a hydrogen atom or a $C_{1-4}$ alkyl group. Preferably, $Y^1$ and $Y^2$ represent a group NR', wherein R' is a hydrogen atom or a $C_{1-4}$ alkyl group. More preferably, $Y^1$ and $Y^2$ represent a group NR', wherein R' is a hydrogen atom.

In a group of formula (II), m represents 0 or an integer of from 1 to 40.

In a preferred embodiment m is 0.

In a preferred embodiment m is an integer of from 1 to 10.

Preferably, m is 1 or 2.

In a compound of formula (I), Z represents any group as defined according to $L^3$.

In a preferred embodiment, Z represents any group as defined according to $L^4$.

Preferably, Z represents a group according to formula (IX).

In a compound of formula (I), $L^2$ represents any group as defined according to $L^3$ or $L^4$. Preferably, $L^2$ represents any group as defined according to $L^3$.

Preferably, $L^2$ is selected from the following groups:

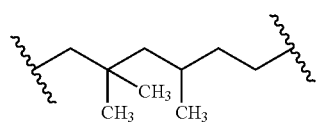

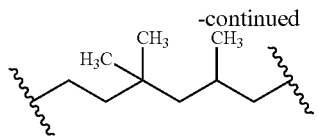

In a preferred embodiment, $L^2$ represents a single bond.

In a compound of formula (I), n represents 0 or an integer of from 1 to 4.

In a preferred embodiment, n is >0.

In a preferred embodiment, n is 0 and $L^2$ is a divalent group of formula (II), wherein m is 0.

In a preferred embodiment, n=0 and $L^2$ represents a divalent group of the formula (II), wherein
$L^3$ is a divalent $C_{1-12}$ hydrocarbon group or a polysiloxane group;
$L^4$ which may be the same or different when more than one $L^4$ is present, independently represents a divalent linker group which may be substituted with up to four substituents of the formula (III), wherein $L^1$ and E are as defined above;
$X^1$ and $X^2$ are oxygen atoms,
$Y^1$ and $Y^2$ are NH groups, and
m is an integer of from 1 to 40.

In a preferred embodiment, n is >0 and $L^2$ represents a divalent group of the formula (II), wherein
$L^3$ is a divalent $C_{1-12}$ hydrocarbon group or a polysiloxane group;
$L^4$ which may be the same or different when more than one $L^4$ is present, independently represents a divalent linker group which may be substituted with up to four substituents of the formula (III), wherein $L^1$ and E are as defined above;
$X^1$ and $X^2$ are oxygen atoms,
$Y^1$ and $Y^2$ are NH groups, and
m is an integer of from 1 to 40.

According to a preferred embodiment, $L^1$ and $L^2$ independently represent a divalent group of the formula (II), wherein
$L^3$ is a divalent $C_{1-12}$ hydrocarbon group or a polysiloxane group;
$L^4$ which may be the same or different when more than one $L^4$ is present, independently represents a divalent linker group which may be substituted with up to four substituents of the formula (III), wherein $L^1$ and E are as defined above;
$X^1$ and $X^2$ are oxygen atoms,
$Y^1$ and $Y^2$ are NH groups,
m is an integer of from 1 to 40; and
Z is a divalent $C_{1-12}$ hydrocarbon group.

When m is greater than 1, then $L^3$, $L^4$, $X^2$, $Y^1$ and $Y^2$ may each be independently the same or different as defined above such that the repeating unit

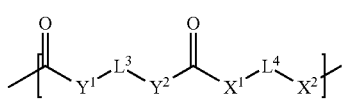

of the divalent group formula (II) may be same or different.

It is to be understood that the divalent group of formula (II) may include an oligomer or polymer chain of the same repeating unit or alternate oligomer or polymer chains of different repeating units and/or random polymer chains of different repeating units. Further, m of formula (II) may encompass i and j of specific embodiments of the compound of formula (I) as shown below:

According to a specific embodiment, the compound of formula (I) is a compound of any one of the following formulae:

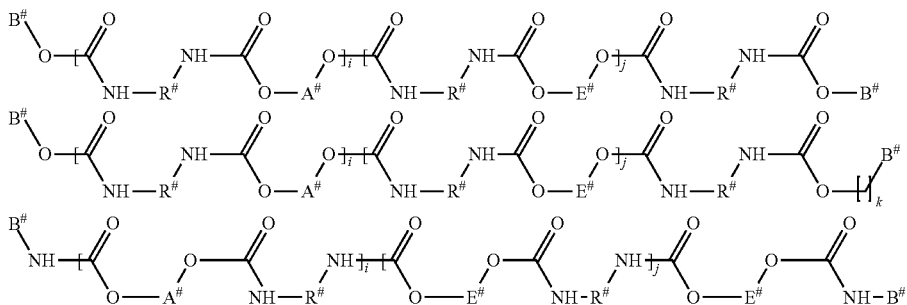

wherein
$B^\#$ is

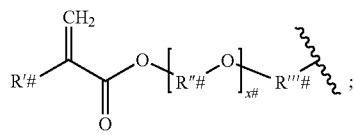

$A^\#$ is

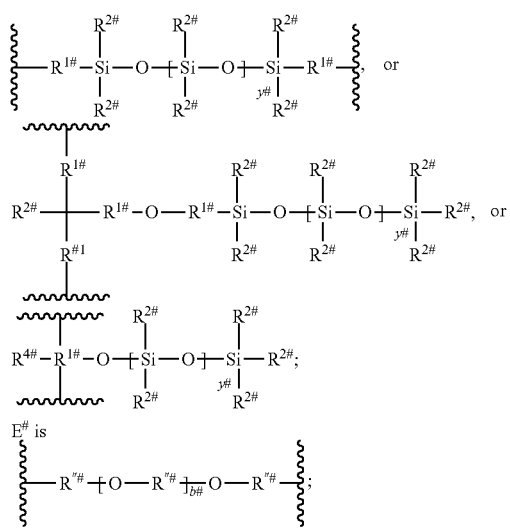

$E^\#$ is

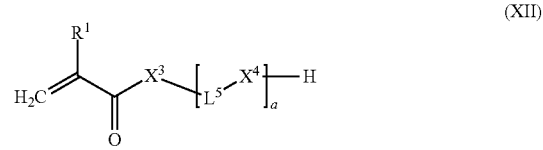

$R^\#$ is an alkylene having from 2 to 25 carbon atoms;
$R'^\#$ is H or $CH_3$;
$R''^\#$ is an alkylene having from 2 to 15 carbon atoms;
$R^{1\#}$ is an alkylene having 1 to 8 carbon atoms;
$R^{2\#}$ is an alkyl having from 1 to 4 carbon atoms;
$R^{4\#}$ is an alkyl, alkoxy or a cycloalkyl group;
i and j are independently an integer from 1 to 20;
x# is an integer from 2 to 10;
y# is an integer from 5 to 20;
b# is an integer from 50 to 100; and
k is an integer from 5 to 15.

According to a preferred embodiment, the compound of formula (I) has a molecular weight of 100 to 10.000 Da, more preferably 300 to 2000 Da.

Preferably, a compound of formula (I) has a dynamic viscosity in the range of from 0.001 to 100 Pas, more preferably 0.1 to 10 Pas. The dynamic viscosity is a measure of the internal resistance of a fluid to flow. The dynamic viscosity can be measured with various types of viscometers and rheometers at a temperature of 25° C.

According to a preferred embodiment, wherein $-L^1-Z-$ represents a divalent group of the formula (II), which is obtainable by reacting a diisocyanate compound, a diol compound, and a polyol compound having at least three hydroxyl groups.

According to a preferred embodiment, $L^2$ represents a divalent group of the formula (II), which is obtainable by reacting a diisocyanate compound and a diol compound.

According to a preferred embodiment, the polymerizable polysiloxane resin mixture is obtainable by reacting a mixture comprising:

(a) x equivalents of one or more di- or polyol compounds of the following formula (X):

$$HO-L^4(OH)_l \qquad (X)$$

wherein
$L^4$ is an (l+1)-valent linker group; and
l is an integer of from 1 to 5;

(b) y equivalents of one or more compounds of the following formula (XI):

$$OCN-L^3NCO \qquad (XI)$$

wherein
$L^3$ is a divalent linker group; and (c) z equivalents of one or more compounds of the following formula (XII):

wherein
$R^1$ represents a hydrogen atom or a $C_{1-12}$ alkyl group;
$X^3$ represents an oxygen atom, a sulfur atom or a group $NR^2$, wherein $R^2$ is a hydrogen atom, $C_{1-12}$ alkyl group, or an allyl group;
$L^5$ is a divalent hydrocarbon linker group, preferably a $C_{2-20}$ alkylene group; and $X^4$ represents an oxygen atom, a sulfur atom or a group $NR^3$, wherein $R^3$ is a hydrogen atom, or a $C_{1-12}$ alkyl group, a represents an integer of from 1 to 20, wherein $0.05 \leq x/y \leq 0.66$, and $2y - \bar{f}x \leq z \leq 1.5(2y - \bar{f}x)$, wherein x, y, and z are the molar equivalents of components (a), (b) and (c) and $\bar{f}$ is the mean hydroxyl functionality of component (a):

$$\bar{f} = \sum_{l=1}^{3} \frac{x_l}{x}(l+1)$$

wherein I is as defined in formula (X) and $x_I/x$ is the molar fraction of the compounds having a hydroxyl functionality of I+1.

The mixture contains x molar equivalents of component (a), y molar equivalents of component (b), and z molar equivalents of component (c).

The molar equivalents are adjusted so that $0.05 \leq x/y \leq 0.66$, and $2y - fx \leq z \leq 1.5(2y - fx)$, wherein f is the mean hydroxyl functionality of component (a) defined by the following formula:

$$\bar{f} = \sum_{l=1}^{3} \frac{x_l}{x}(l+1)$$

wherein I is as defined in formula (X) and $x_I/x$ is the molar fraction of the compounds having an hydroxyl functionality of I+1.

Accordingly, the molar equivalents x of component (a) depend on the functionality of the one or more di- and/or polyhydroxyl compounds contained in component (a). According to a preferred embodiment, I is 1. When I is 1, then f is 2. According to a further preferred embodiment, the mixture contains one compound of formula (I), preferably wherein I is 1. As a result, compounds according to formula (I) are linear.

According to the present invention, the molar equivalent y is larger than the molar equivalent x in that $0.05 \leq x/y \leq 0.66$. Given that y>x and depending on the molar ratio of r'=x/y, the polymerization degree (Pa) increases according to Pa= $(1+r')/(1-r')$. In case x/y>0.66, the viscosity of the polymerizable composition may become excessively large so that large amounts of a solvent or reactive diluent are required for providing a light-curable dental impression material of the present invention. In case x/y<0.05, the polymerizable composition contains an excess of reaction products between component (b) and component (c) whereby the mechanical properties of the light-curable dental impression material of the present invention are deteriorated.

The mixture contains z molar equivalents of a one or more and chain terminating compounds (c). The amount of z is selected according to the present invention so that $2y - fx \leq z \leq 1.5(2y - fx)$, wherein f is the mean hydroxyl functionality of component (a) defined above. Preferably, z is 2y-fx. In case x<2y-fx, then the content of end groups in the macromers contained in the polymerizable mixture of the present invention may be reduced which is not preferable in view of the mechanical properties of the dental composite of the present invention. In case z>1.5(2y-fx), the excess of chain terminating compounds may compete with the reaction of component (a) and component (b) and interfere with the macromer formation.

The average molecular weight $\bar{M}$ of the polymerizable mixture may be estimated according to the following formula:

$$\bar{M} = x\overline{M_{(a)}} + y\overline{M_{(b)}} + z\overline{M_{(c)}}$$

In the above formula $\overline{M_{(a)}}$ is the average molecular weight of component (a), $\overline{M_{(b)}}$ is the average molecular weight of component (b), and $\overline{M_{(c)}}$ is the average molecular weight of component (c).

According to an alternative embodiment, the polymerizable polysiloxane resin mixture is obtainable by reacting a mixture comprising:

(a') x equivalents of one or more di- or polyisocyanate compounds of the following formula (X'):

$$OCN-L^{4'}(NCO)_{I'} \quad (X')$$

wherein $L^{4'}$ is an (I'+1)-valent linker group; and

I' is an integer of from 1 to 5;

(b') y equivalents of one or more diol compounds of the following formula (XI'):

$$HO-L^{3'}OH \quad (XI')$$

wherein $L^{3'}$ is a divalent linker group; and (c') z equivalents of one or more compounds of the following formula (XII'):

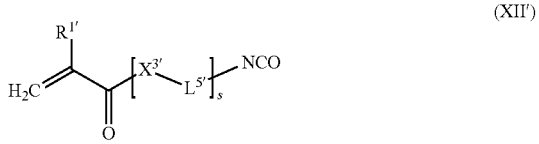

(XII')

wherein $R^{1'}$ represents a hydrogen atom or a $C_{1-12}$ alkyl group;

$X^{3'}$ represents an oxygen atom, a sulfur atom or a group $NR^2$, wherein $R^2$ is a hydrogen atom, $C_{1-12}$ alkyl group, or an allyl group;

$L^{5'}$ is a divalent hydrocarbon linker group, preferably a $C_{2-20}$ alkylene group;

s is 0 or an integer of from 1 to 6; and wherein $0.05 \leq x/y \leq 0.66$, and $2y - \bar{f}x \leq z \leq 1.5(2y - \bar{f}x)$, wherein x, y, and z are the molar equivalents of components (a'), (b') and (c') and $\bar{f}$ is the mean isocyanate functionality of component (a):

$$\bar{f} = \sum_{l=1}^{3} \frac{x_l}{x}(l+1)$$

wherein I is I' as defined in formula (X') and $x_I/x$ is the molar fraction of the compounds having an isocyanate functionality of I'+1.

The mixture contains x molar equivalents of component (a'), y molar equivalents of component (b'), and z molar equivalents of component (c').

The molar equivalents are adjusted so that $0.05 \leq x/y \leq 0.66$, and $2y - fx \leq z \leq 1.5(2y - fx)$, wherein f is the mean isocyanate functionality of component (a) defined by the following formula:

$$\bar{f} = \sum_{l=1}^{3} \frac{x_l}{x}(l+1)$$

wherein I is as defined in formula (X) and $x_I/x$ is the molar fraction of the compounds having an hydroxyl functionality of I+1.

Accordingly, the molar equivalents x of component (a) depend on the functionality of the one or more di- and/or polyhydroxyl compounds contained in component (a). According to a preferred embodiment, I is 1. When I is 1, then f is 2. According to a further preferred embodiment, the mixture contains one compound of formula (I), preferably wherein I is 1. As a result, compounds according to formula (I) are linear.

According to the present invention, the molar equivalent y is larger than the molar equivalent x in that $0.05 \leq x/y \leq 0.66$. Given that y>x and depending on the molar ratio of r'=x/y, the polymerization degree (Pa) increases according to Pa= (1+r')/(1−r'). In case x/y>0.66, the viscosity of the polymerizable composition may become excessively large so that large amounts of a solvent or reactive diluent are required for providing a light-curable dental impression material of the present invention. In case x/y<0.05, the polymerizable composition contains an excess of reaction products between component (b) and component (c) whereby the mechanical properties of the light-curable dental impression material of the present invention are deteriorated.

The mixture contains z molar equivalents of a one or more and chain terminating compounds (c). The amount of z is selected according to the present invention so that $2y-fx \leq z \leq 1.5(2y-fx)$, wherein f is the mean isocyanate functionality of component (a) defined above. Preferably, z is 2y−fx. In case x<2y−fx, then the content of end groups in the macromers contained in the polymerizable mixture of the present invention may be reduced which is not preferable in view of the mechanical properties of the dental composite of the present invention. In case z>1.5(2y−fx), the excess of chain terminating compounds may compete with the reaction of component (a) and component (b) and interfere with the macromer formation.

The average molecular weight $\bar{M}$ of the polymerizable mixture may be estimated according to the following formula:

$$\bar{M} = x\overline{M_{(a)}} + y\overline{M_{(b)}} + z\overline{M_{(c)}}$$

In the above formula $\overline{M_{(a)}}$ is the average molecular weight of component (a'), $\overline{M_{(b)}}$ is the average molecular weight of component (b'), and $\overline{M_{(c)}}$ is the average molecular weight of component (c').

Preferably, the light-curable dental impression material comprises 2 to 95 percent by weight, based on the total weight of the light-curable dental impression material, of a polymerizable polysiloxane resin composition comprising compounds of formula (I). More preferably, the light-curable dental impression material comprises 4 to 20 percent by weight, based on the total weight of the light-curable dental impression material, of compounds of formula (I).

Additionally, the light-curable dental impression material may preferably comprise up to 75 percent by weight, based on the total weight of the light-curable dental impression material, of polymerizable compounds of formula (I), but lack any polysiloxane moiety. Preferably, the light-curable dental impression material may comprises 10 to 50 percent by weight, based on the total weight of the light-curable dental impression material, of such polymerizable compounds of formula (I) lacking any polysiloxane moiety.

In the preparation of the polymerizable compounds of formula (I), coupling agents may be used. Examples of suitable coupling agents are bismuth compounds such as bismuth 2-ethyl hexanoate (K-KAT 348), tin compounds such as dibutyl tin dioctanoate, and tertiary amines such as 1,4-diazabicyclo[2.2.2]octane (DABCO).

The Filler

The light-curable dental impression material of the present invention comprises a filler. The filler is a particulate filler which has preferably a mean particle size in the range of from 0.05 to 75 µm as measured, for example, by electron microscopy or by using a conventional laser diffraction particle sizing method as embodied by a MALVERN Mastersizer S or MALVERN Mastersizer 3000 apparatus. The particulate filler may be a multimodal particulate filler representing a mixture of two or more particulate fractions having different average particle sizes. The particulate reactive filler may also be a mixture of particles of different chemical composition.

Preferably, the photocurable dental impression material comprises 10 to 60 percent by weight, more preferably 20 to 50 percent by weight, based on the total weight of the dental impression material of a filler.

The specific type of filler is not particularly limited. In order to achieve a usable depth of cure, preferred are fillers with a refractive index comparable to the one of the polymerisable resin mixture. Accordingly, any toxicologically acceptable inorganic, especially hydrophobic fillers may be employed such as silicas, aluminas, magnesias, titanias, inorganic salts, metallic oxides and glasses.

The filler may be a mixtures of different fillers such as silicone dioxides including crystalline forms, in particular particulate quartz, amorphous silicon dioxides, in particular diatomaceous earth, and silanated fumed silica.

The viscosity and thixotropicity of the uncured as well as the physical properties of the cured compositions may be controlled by varying the sizes and surface areas of the filler.

The filler may be surface treated with one or more silanating agents. Preferred silanating agents include those having at least one polymerizable double bond and at least one group that easily hydrolyses with water. Examples of such agents include 3-methacryloxypropyltrimethoxysilane, 3-methacryloxypropyldimethoxy-monochlorosilane, 3-methacryloxypropyldichloromonomethoxysilane, methacryloxypropyltri-chlorosilane, 3-methacryloxypropyldichloromonomethyl-silane, 3-methacryloxypropylmonochlorodimethylsilane, and mixtures thereof.

Preferred filler are fumed silica, quartz, cristobalite, calcium silicate, diatomaceous earth, zirconium silicate, montmorillonite such as bentonite, zeolite, including molecular sieves such as sodium aluminium silicate, metal oxide powder such as aluminium or zinc oxide or their mixed oxides, barium sulphate, calcium carbonate, plaster, and glass powder.

Preferably, the light-curable dental impression material comprises 5 to 50 percent by weight, based on the total weight of the light-curable dental impression material, of a particulate filler. More preferably, the filler is contained in an amount of from 10 to 45 percent by weight based on the total weight of the light-curable dental impression material.

The Photoinitiator

The light-curable dental impression material of the present invention comprises a photoinitiator. The photoinitiator generates free radicals upon exposure to actinic light. Free radicals may be typically produced by either of two pathways:
(1) a photoinitiator compound undergoes excitation by energy absorption with subsequent decomposition of the compound into one or more radicals (Norrish type I), or
(2) a photoinitiator compound undergoes excitation and the excited photoinitiator compound interacts with a second compound by either energy transfer or a redox reaction to form free radicals from any of the compounds (Norrish type II).

According to the present invention any compound or system capable of initiating the polymerization of the mixture of polymerizable silicone compounds according to the present invention may be used.

For example, a suitable photoinitiator system may be in the form of a binary or tertiary system. A binary systems may include a photoinitiator and an electron donor compound, and a tertiary system may include an iodonium, sulfonium or phosphonium salt, a photoinitiator, and an electron donor compound, as for example described in U.S. Pat. No. 5,545,676.

Suitable photoinitiators are monoketones and diketones that absorb some light within a range of about 400 nm to about 520 nm (preferably, about 450 nm to about 500 nm). Particularly suitable compounds include alpha diketones that have some light absorption within a range of about 400 nm to about 520 nm (even more preferably, about 450 to about 500 nm). Examples include camphor quinone, benzil, furil, 3,3,6,6-tetramethylcyclo-hexanedione, phenanthraquinone, 1-phenyl-1,2-propanedione and other 1-aryl-2-alkyl-1,2-ethanediones, and cyclic alpha diketones.

Moreover, suitable photoinitiators are compounds of the following formula (III) as disclosed in EP 3231413 A1 and EP 3153150 A1:

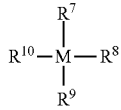

(XIII)

In a compound of formula (XIII), M is Ge or Si.

Moreover, in a compounds of formula (XIII), $R^7$, $R^8$ and $R^9$ may be the same or different, independently represent an organic group. Preferably, $R^7$ and $R^8$ independently from each other represent a substituted or unsubstituted hydrocarbyl or hydrocarbylcarbonyl group, and $R^9$ represents a substituted or unsubstituted hydrocarbyl group. The hydrocarbyl group may be an alkyl group, a cycloalkyl group, a cycloalkylalkyl group, an arylalkyl group or an aryl group. An alkyl group may be linear $C_{1-20}$ or branched $C_{3-20}$ alkyl group, typically a linear $C_{1-8}$ or branched $C_{3-8}$ alkyl group. Examples for $C_{1-16}$ alkyl groups can include linear or branched alkyl groups having 1 to 6 carbon atoms, preferably 1 to 4 carbon atoms, for example, methyl, ethyl, n-propyl, isopropyl, n-butyl, isobutyl, sec-butyl, tert-butyl, n-pentyl, isopentyl and n-hexyl. A cycloalkyl group may be a $C_{3-20}$ cycloalkyl group, typically a $C_{3-8}$ cycloalkyl group. Examples of the cycloalkyl group can include those having 3 to 6 carbon atoms, for example, cyclopropyl, cyclobutyl, cyclopentyl and cyclohexyl.

A cycloalkylalkyl group may have 4 to 20 carbon atoms and may include a combination of a linear or branched alkyl group having 1 to 6 carbon atoms and a cycloalkyl group having 3 to 14 carbon atoms. Examples of the cycloalkyl-alkyl(-) group can for example, include methylcyclopropyl, methylcyclobutyl, methylcyclopentyl, methylcyclohexyl, ethylcyclopropyl, ethylcyclobutyl, ethylcyclopentyl, ethylcyclohexyl, propylcyclopropyl, propylcyclobutyl, propylcyclopentyl, propylcyclohexyl. An arylalkyl group may be a $C_{7-20}$ arylalkyl group, typically a combination of a linear or branched alkyl group having 1 to 6 carbon atoms and an aryl group having 6 to 10 carbon atoms. Specific examples of an arylalkyl group are a benzyl group or a phenylethyl group. An aryl group can include aryl groups having 6 to 10 carbon atoms. Examples of the aryl group are phenyl and naphtyl.

The hydrocarbylcarbonyl groups of $R^7$ and $R^8$ represent acyl groups ($R_{org}$-(C=O)—) in which the organic residue $R_{org}$ is a hydrocarbyl residue as defined above.

Compound of formula (XIII) may contain one or two hydrocarbylcarbonyl groups, that is either one of $R^7$ and $R^8$ is a hydrocarbylcarbonyl group, or both $R^7$ and $R^8$ are hydrocarbylcarbonyl groups. Preferably, compound of formula (XIII) contains one hydrocarbylcarbonyl group. Preferably, the hydrocarbylcarbonyl group is an arylcarbonyl group, more preferably a benzoyl group. Preferably, $R^7$ and $R^8$ are independently selected from the group consisting of a linear $C_{1-6}$ or branched $C_{3-8}$ alkyl group, and a phenyl or benzoyl group which may optionally be substituted by one to three substitutents selected from halogen atoms, a nitro group, a $C_{1-4}$ alkoxy group and a —$NR^xR^y$ group wherein $R^x$ and $R^y$ independently from each other represent a $C^{1-4}$ alkyl group, and $R^9$ is a linear or branched $C_{3-6}$ alkyl group or a phenyl group. Most preferably, $R^7$ and $R^8$ are independently selected from the group of a linear $C_{1-4}$ or branched $C_3$ or $C_4$ alkyl group, and a phenyl or benzoyl group which may optionally be substituted with one substituent selected from the group consisting of selected from a halogen atom, a nitro group, a $C_{1-4}$ alkoxy group and a -$NR^xR^y$ group wherein $R^x$ and $R^y$ independently from each other represent a $C_{1-4}$ alkyl group, and $R^9$ is a linear $C_{1-4}$ or branched $C_3$ or $C_4$ alkyl group.

Moreover, in a compounds of formula (XIII), $R^{10}$ represents a hydrogen atom, an organic or organometallic group, provided that when $R^{10}$ is a hydrogen atom, the initiator system further comprises a sensitizer compound having a light absorption maximum in the range from 300 to 600 nm.

According to a first preferred embodiment, $R^{10}$ represents a group of the following formula (XIV):

(XIV)

wherein $R^{11}$
(i) is a group of the following formula (XV):

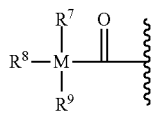

(XV)

wherein

M, $R^7$, $R^8$ and $R^9$ have the same meaning as defined above for formula (XIII), whereby the compound of formula (XIII) may be symmetrical or unsymmetrical; or (ii) is a group of the following formula (XVI):

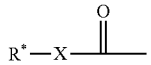
(XVI)

wherein

X represents a single bond, an oxygen atom or a group $NR^{x1}$, wherein $R^{x1}$ represents a substituted or unsubstituted hydrocarbyl group;

R* represents a substituted or unsubstituted hydrocarbyl group, a trihydrocarbylsilyl group, a mono(hydrocarbylcarbonyl)dihydrocarbylsilyl group or a di(hydrocarbylcarbonyl)monohydrocarbylsilyl group; or (iii) when M is Si, $R^{11}$ may be a substituted or unsubstituted hydrocarbyl group.

For R* of formula (XVI) being a trihydrocarbylsilyl-group, a mono(hydrocarbylcarbonyl)-dihydrocarbylsilyl group or a di(hydrocarbylcarbonyl)monohydrocarbylsilyl group, each of the hydrocarbyl and hydrocarbylcarbonyl groups has the same meaning as defined for $R^7$, $R^8$ and $R^9$ and is independently selected therefrom.

In formula (XVI), $R^{x1}$ has the same meaning as defined for $R^9$ and is independently selected therefrom.

According to a second preferred embodiment, $R^{10}$ represents a hydrogen atom. Accordingly, the initiator system further comprises a sensitizer compound. The sensitizer compound is preferably an alpha-diketone sensitizer compound having a light absorption maximum in the range from 300 to 500 nm. The alpha-diketone sensitizer is capable of absorbing visible light and forming a photoexcitation complex with a hydrogen donating compound of formula (XIII). The alpha-diketone photoinitiator compound may be selected from camphorquinone, 1,2-diphenylethane-1,2-dione (benzil), 1,2-cyclohexanedione, 2,3-pentanedione, 2,3-hexanedione, 3,4-hexanedione, 2,3-heptanedione, 3,4-heptanedione glyoxal, biacetyl, 3,3,6,6-tetramethylcyclohexanedione, 3,3,7,7-tetramethyl-1,2-cycloheptanedione, 3,3,8,8-tetramethyl-1,2-cyclooctanedione; 3,3,18,18-tetramethyl-1,2-cyclooctadecanedione; dipivaloyl; furil, hydroxybenzil, 2,3-butanedione, 2,3-octanedione, 4,5-octanedione, and 1-phenyl-1,2-propanedione. Camphorquinone is the most preferred alpha-diketone photoinitiator. According to a preferred embodiment, the light-curable dental impression material contains the alpha-diketone sensitizer in an amount from 0.01 to 5 percent by weight, based on the total weight of composition.

Preferably, in the compounds of formula (XIII), M is Si.

For example, compounds of formula (XIII) wherein $R^{11}$ has the formula (XV) and which are symmetrical may be have the following structural formulae:

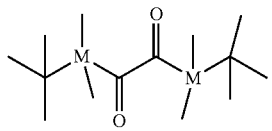 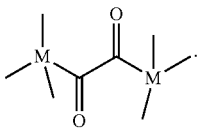

For example, compounds of formula (XIII) wherein $R^{11}$ represents a group of formula (XVI) wherein X is a bond, an oxygen atom or a $NR^{X1}$ group, and R* represents a substituted or unsubstituted hydrocarbyl group may have the following structural formulae:

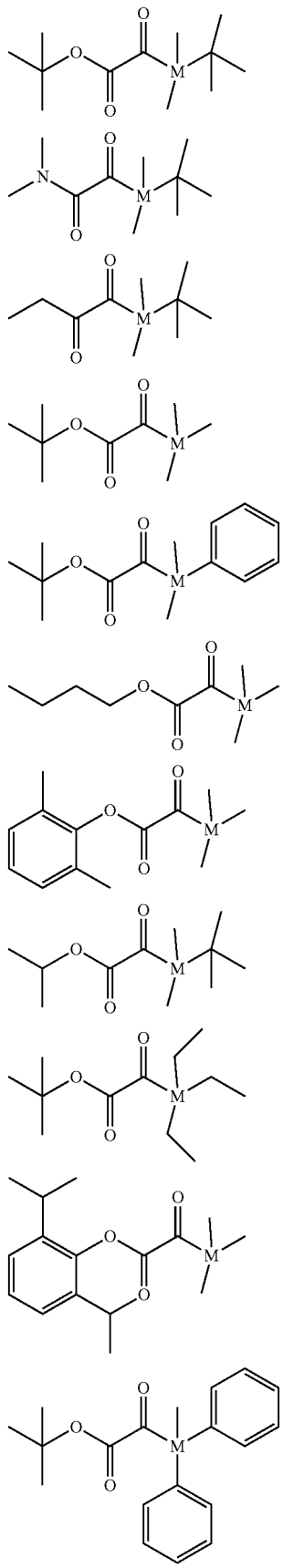

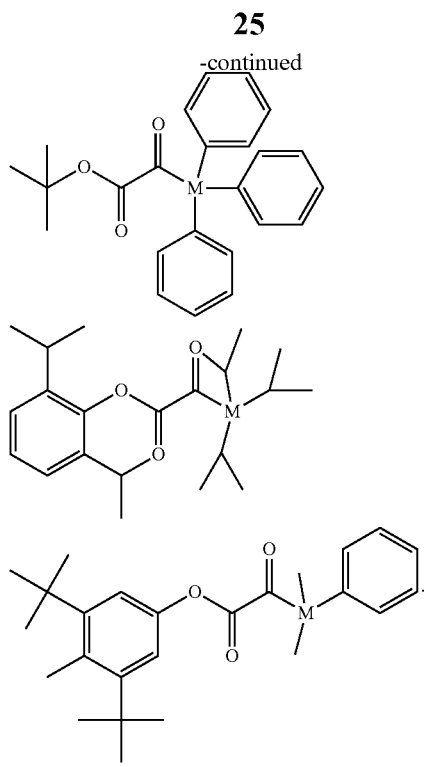

For example, compounds of formula (XIII) wherein R represents a group of formula (XVI) wherein R* represents a trihydrocarbylsilyl group have the following structural formulae:

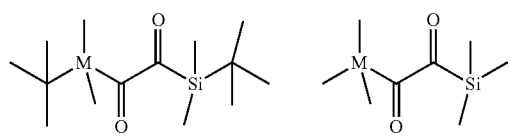

For example, compounds of formula (XIII) wherein M is Si and $R^{11}$ represents a substituted or unsubstituted hydrocarbyl group may have the following structural formulae:

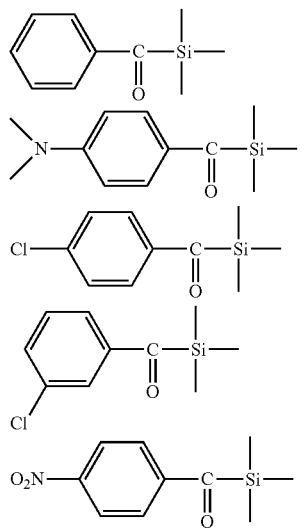

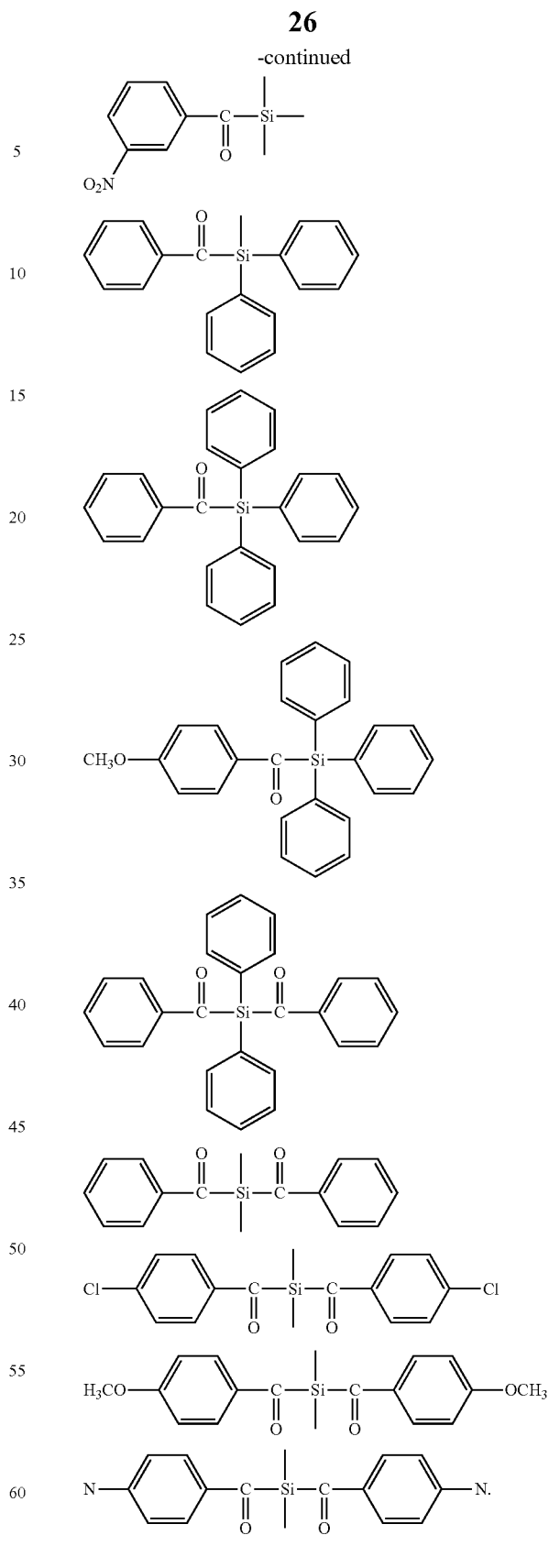

Preferably, compound of formula (XIII) is selected from the group consisting of:

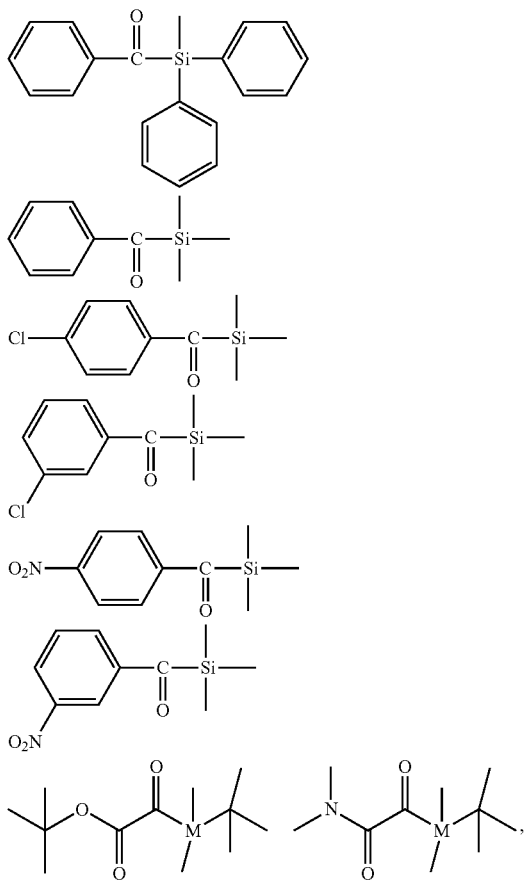

wherein compounds of formula (XIII) with M=Si are particularly preferred.

More preferably, compound of formula (XIII) is selected from the group consisting of:

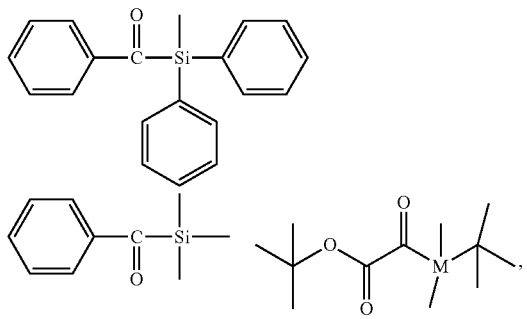

wherein it is particularly preferred that M=Si.

Most preferably, compound of formula (XIII) is tert-butyl (tert-butyldimethylsilyl)glyoxylate) (DKSi).

A suitable photoinitiator system may also include phosphine oxides typically having a functional wavelength range of about 380 nm to about 1200 nm. Examples of phosphine oxide free radical initiators with a functional wavelength range of about 380 nm to about 450 nm include acyl and bisacyl phosphine oxides such as those described in U.S. Pat. Nos. 4,298,738, 4,324,744 and 4,385,109 and EP 0 173 567. Specific examples of the acylphosphine oxides include 2,4,6-trimethylbenzoyldiphenylphosphine oxide, bis(2,4,6-trimethylbenzoyl)phenylphosphine oxide, dibenzoylphenylphosphine oxide, bis(2,6-dimethoxybenzoyl)phenylphosphine oxide, tris(2,4-dimethylbenzoyl)phosphine oxide, tris(2-methoxybenzoyl)phosphine oxide, 2,6-dimethoxybenzoyldiphenyl phosphine oxide, 2,6-dichlorobenzoyldiphenylphosphine oxide, 2,3,5,6-tetramethylbenzoyldiphenylphosphine oxide, benzoyl-bis(2,6-dimethylphenyl) phosphonate, and 2,4,6-trimethylbenzoylethoxyphenylphosphine oxide. Commercially available phosphine oxide photoinitiators capable of free-radical initiation when irradiated at wavelength ranges of greater than about 380 nm to about 450 nm include bis(2,4,6-trimethylbenzoyl)phenyl phosphine oxide (IRGACURE 819), bis(2,6-dimethoxybenzoyl)-(2,4,4-trimethylpentyl) phosphine oxide (CGI 403), a 25:75 mixture, by weight, of bis(2,6-dimethoxybenzoyl)-2,4,4-trimethylpentyl phosphine oxide and 2-hydroxy-2-methyl-1-phenylpropan-1-one (IRGACURE 1700), a 1:1 mixture, by weight, of bis(2,4,6-trimethylbenzoyl)phenyl phosphine oxide and 2-hydroxy-2-methyl-1-phenylpropane-1-one (DAROCUR 4265), and ethyl 2,4,6-trimethylbenzylphenyl phosphinate (LUCIRIN LR8893X). Typically, the phosphine oxide initiator is present in the composition in catalytically effective amounts, such as from 0.01 percent by weight to 5.0 percent by weight, based on the total weight of the composition.

Suitable electron donor compounds include substituted amines, e.g., ethyl dimethylaminobenzoate and/or dimethylamino benzonitrile.

Tertiary amine reducing agents may be used in combination with an acylphosphine oxide Examples of suitable aromatic tertiary amine include N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-isopropylaniline, N,N-dimethyl-4-t-butylaniline, N,N-dimethyl-3,5-di-t-butylaniline, N,N-bis(2-hydroxyethyl)-3,5-dimethylaniline, N,N-bis(2-hydroxyethyl)-p-toluidine, N,N-bis(2-hydroxyethyl)-3,4-dimethylaniline, N,N-bis(2-hydroxyethyl)-4-ethylaniline, N,N-bis(2-hydroxyethyl)-4-isopropylaniline, N,N-bis(2-hydroxyethyl)-4-t-butylaniline, N,N-bis(2-hydroxyethyl)-3,5-di-isopropylaniline, N,N-bis(2-hydroxyethyl)-3,5-di-t-butylaniline, 4-N,N-dimethylaminobenzoic acid ethyl ester, 4-N,N-dimethylaminobenzoic acid methyl ester, 4-N,N-dimethylaminobenzoic acid n-butoxyethyl ester, 4-N,N-dimethylaminobenzoic acid 2-(methacryloyloxy) ethyl ester, 4-N,N-dimethylaminobenzophenone ethyl 4-(N,N-dimethylamino) benzoate and N,N-dimethylaminoethyl methacrylate. Examples of an aliphatic tertiary amine include trimethylamine, triethylamine, N-methyldiethanolamine, N-ethyldiethanolamine, N-n-butyldiethanolamine, N-lauryldiethanolamine, triethanolamine, 2-(dimethylamino) ethyl methacrylate, N-methyldiethanolamine dimethacrylate, N-ethyldiethanolamine dimethacrylate, triethanolamine monomethacrylate, triethanolamine dimethacrylate, and triethanolamine trimethacrylate.

One or more amine reducing agents may be present in the composition in an amount from 0.01 percent by weight to 5.0 percent by weight, based on the total weight of the composition.

According to a further preferred embodiment, the photo initiator further comprises an iodonium compound of the following formula (XVII):

$$R^{12}\text{-}I^{30}\text{-}R^{13}A\text{-} \qquad (XVII)$$

wherein

R$^{12}$ and R$^{13}$ which are independent from each other, represent an organic moiety, and A- is an anion;

For example, diaryl iodonium salt may be selected from (4-methylphenyl)[4-(2-methylpropyl) phenyl] iodonium hexafluoroantimonate, include (4-methylphenyl)[4-(2-methylpropyl) phenyl] iodonium tetrafluoroborate, diphenyliodonium (DPI) tetrafluoroborate, di(4-methylphenyl)iodonium (Me2-DPI) tetrafluoroborate, phenyl-4-methylphenyliodonium tetrafluoroborate, di(4-heptylphenyl)iodonium tetrafluoroborate, di(3-nitrophenyl)iodonium hexafluorophosphate, di(4-chlorophenyl)iodonium hexafluorophosphate, di(naphthyl)iodonium tetrafluoroborate, di(4-trifluoromethylphenyl)iodonium tetrafluoroborate, DPI hexafluorophosphate, Me2-DPI hexafluorophosphate; DPI hexafluoroarsenate, di(4-phenoxyphenyl)iodonium tetrafluoroborat, phenyl-2-thienyliodonium hexafluorophosphate, 3,5-dimethylpyrazolyl-4-phenyliodonium hexafluorophosphate, DPI hexafluoroantimonate, 2,2'-DPI tetrafluoroborate, di(2,4-dichlorophenyl)iodonium hexafluorophosphate, di(4-bromophenyl)iodonium hexafluorophosphate, di(4-nnethoxyphenyl)iodonium hexafluorophosphate, di(3-carboxyphenyl)iodonium hexafluorophosphate, di(3-methoxycarbonylphenyl)iodonium hexafluorophosphate, di(3-methoxysulfonylphenyl)iodonium hexafluorophosphate, di(4-acetamidophenyl)iodonium hexafluorophosphate, di(2-benzothienyl)iodonium hexafluorophosphate, and DPI hexafluorophosphate.

Particularly preferred iodonium compounds include diphenyliodonium (DPI) hexafluorophosphate, di(4-methylphenyl)iodonium (Me2-DPI) hexafluorophosphate, diaryliodonium hexafluoroantimonate, (4-methylphenyl)[4-(2-methylpropyl) phenyl] iodonium hexafluoroantimonate, (4-nnethylphenyl)[4-(2-methylpropyl)phenyl]iodonium hexafluorophosphate (Irgacure® 250, commercial product available from BASF SE), (4-methylphenyl)[4-(2-methylpropyl) phenyl] iodonium tetrafluoroborate, 4-octyloxyphenyl phenyliodonium hexafluoroantimonate, 4-(2-hydroxytetradecyloxyphenyl)phenyliodonium hexafluoroantimonate, and 4-isopropyl-4'-methyldiphenyliodonium borate.

According to a particularly preferred embodiment, the iodonium compound is DPI hexafluorophosphate and/or 4-isopropyl-4'-methyldiphenyliodonium tetrakis(pentafluorophenyl) borate.

According to a further preferred embodiment, the photo initiator further comprises a sulfonium compound of the following formula (XVIII):

R$^{14}$R$^{15}$R$^{16}$S$^{+}$A$^{-}$ (XVIII)

wherein

R$^{14}$, R$^{15}$ and R$^{16}$ which are independent from each other, represent an organic moiety or wherein any two of R$^{14}$, R$^{15}$ and R$^{16}$ form a cyclic structure together with the sulfur atom to which they are bound, and A$^{-}$is an anion.

A preferred triaryl sulfonium salt is S-(phenyl)thianthrenium hexafluorophosphate:

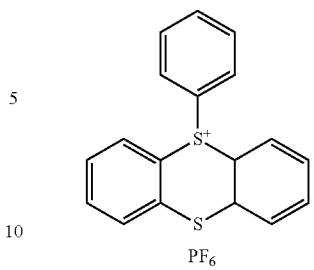

According to a further preferred embodiment, the photo initiator further comprises a phosphonium compound of the following formula (XIX):

R$^{17}$R$^{18}$R$^{19}$R$^{20}$P$^{+}$A$^{31}$ (XIX)

wherein

R$^{17}$, R$^{18}$, R$^{19}$, and R$^{20}$ which are independent from each other, represent an organic moiety, and A$^{-}$is an anion.

Particularly preferred phosphonium salts are the tetraalkyl phosphonium salts tetrakis-(hydroxymethyl)-phosphonium (THP) salt or a tetrakis-(hydroxymethyl)-phosphonium hydroxide (THPOH) salt, wherein the anion of the tetraalkyl phosphonium salt is selected from the group consisting of formate, acetate, phosphate, sulphate, fluoride, chloride, bromide and iodide.

According to a preferred embodiment, the light-curable dental impression material comprises 0.01 to 5 percent by weight, alternatively 0.1 to 5 percent by weight, more preferably 1 to 4 percent by weight, based on the total weight of the light-curable dental impression material, of a photoinitiator.

Optional Polvmerizable (Meth)Acrvlates or (Meth)Acrylamides

The light-curable dental impression material of the present invention may further comprise with up to 20 percent by weight based on the total weight of the composition of polymerizable (meth)acrylates or (meth)acrylamides.

The (meth)acrylate compounds may be selected from methyl acrylate, methyl methacrylate, ethyl acrylate, ethyl methacrylate, propyl acrylate, propyl methacrylate, isopropyl acrylate, isopropyl methacrylate, 2-hydroxyethyl acrylate, 2-hydroxyethyl methacrylate (HEMA), hydroxypropyl acrylate, hydroxypropyl methacrylate, tetrahydrofurfuryl acrylate, tetrahydrofurfuryl methacrylate, glycidyl acrylate, glycidyl methacrylate, bisphenol A glycerolate dimethacrylat ("bis-GMA", CAS-No. 1565-94-2), 4,4,6,16 (or 4,6,6,16)-tetramethyl-10,15-dioxo-11,14-dioxa-2,9-diazaheptadec-16-enoicacid 2-[(2-methyl-1-oxo-2-propen-1-yl)oxy] ethyl ester (CAS no. 72869-86-4)_(UDMA), glycerol mono- and di- acrylate such as 1,3-glycerol dimethacrylate (GDM), glycerol mono-and dimethacrylate, ethyleneglycol diacrylate, ethyleneglycol dimethacrylate, polyethyleneglycol diacrylate (where the number of repeating ethylene oxide units vary from 2 to 30), polyethyleneglycol dimethacrylate (where the number of repeating ethylene oxide units vary from 2 to 30 especially triethylene glycol dimethacrylate ("TEGDMA"), neopentyl glycol diacrylate, neopentylglycol dimethacrylate, trimethylolpropane triacrylate, trimethylol propane trimethacrylate, mono-, di-, tri-, and tetra- acrylates and methacrylates of pentaerythritol and dipentaerythritol, 1,3-butanediol diacrylate, 1,3-butanediol dimethacrylate, 1,4-butanedioldiacrylate, 1,4-butanediol dimethacrylate, 1,6-hexane dial diacrylate, 1,6-hexanediol dimethacrylate, di-2-methacryloyloxethyl hexamethylene dicarbamate, di-2-methacryloyloxyethyl trimethylhexanethylene dicarbamate, di-2-methacryloyl oxyethyl dimethylbenzene dicarbamate, methylene-bis-2-methacryloxyethyl-4-cyclohexyl carbamate, di-2-methacryloxyethyl-dimethylcyclohexane dicarbamate, methylene-bis-2-methacryloxyethyl-4-cyclohexyl carbamate, di-1-methyl-2-methacryloxyethyl-trimethylhexamethylene dicarbamate, di-1-methyl-2-methacryloxyethyl-dimethylbenzene dicarbamate, di-1-methyl-2-methacryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-2-methacryloxyethyl-4-cyclohexyl carbamate, di-1-methyl-2-methacryloxyethyl-hexamethylene dicarbamate, di-1-methyl-2-methacryloxyethyl-trimethylhexamethylene dicarbamate, di-1-methyl-2-methacryloxyethyl-dimethylbenzene dicarbamate, di-1-methyl-2-metha-cryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-1-chloromethyl-2-methacryloxyethyl4-cyclohexyl carbamate, 2,2'-bis(4-methacryloxyphenyl)propane, 2,2'bis(4-acryloxyphenyl)propane, 2,2'-bis[4(2-hydroxy-3-methacryloxy-phenyl)]propane, 2,2'-bis[4(2-hydroxy-3-acryloxy-phenyl)propane, 2,2'-bis(4-methacryloxyethoxyphenyl)propane, 2,2'-bis(4-acryloxyethoxyphenyl)propane, 2,2'-bis(4-methacryloxypropoxyphenyl)propane, 2,2'-bis(4-acryloxypropoxyphenyl)propane, 2,2'-bis(4-methacryloxydiethoxyphenyl)propane, 2,2'-bis(4-acryloxydiethoxyphenyl)propane, 2,2'-bis[3(4-phenoxy)-2-hydroxypropane-1-methacrylate]propane, and 2,2'-bis[3(4-phenoxy)-2-hydroxypropane-1-acrylate]propane.

Preferred (meth)acrylamides may be selected from the following compounds.

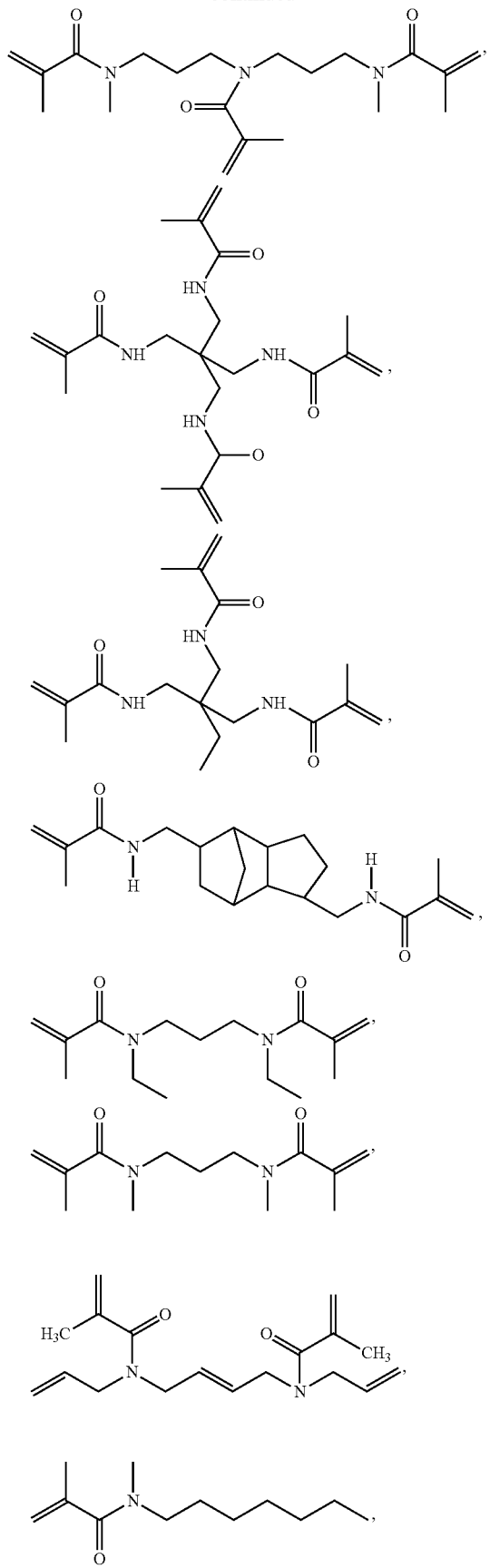

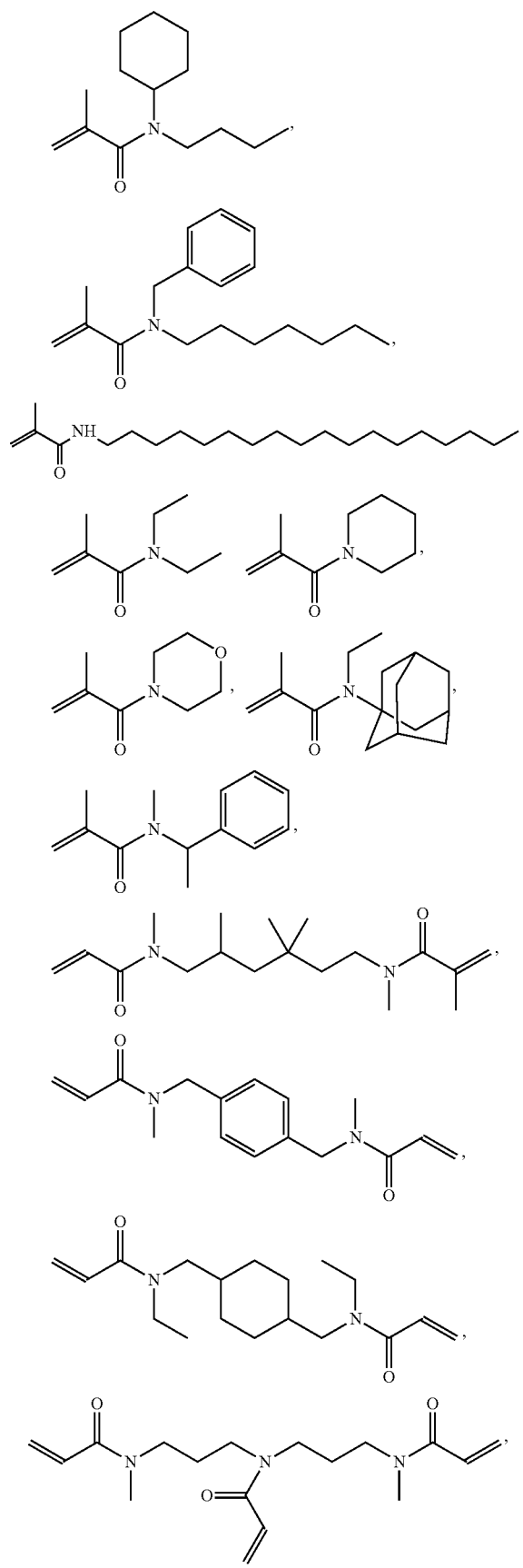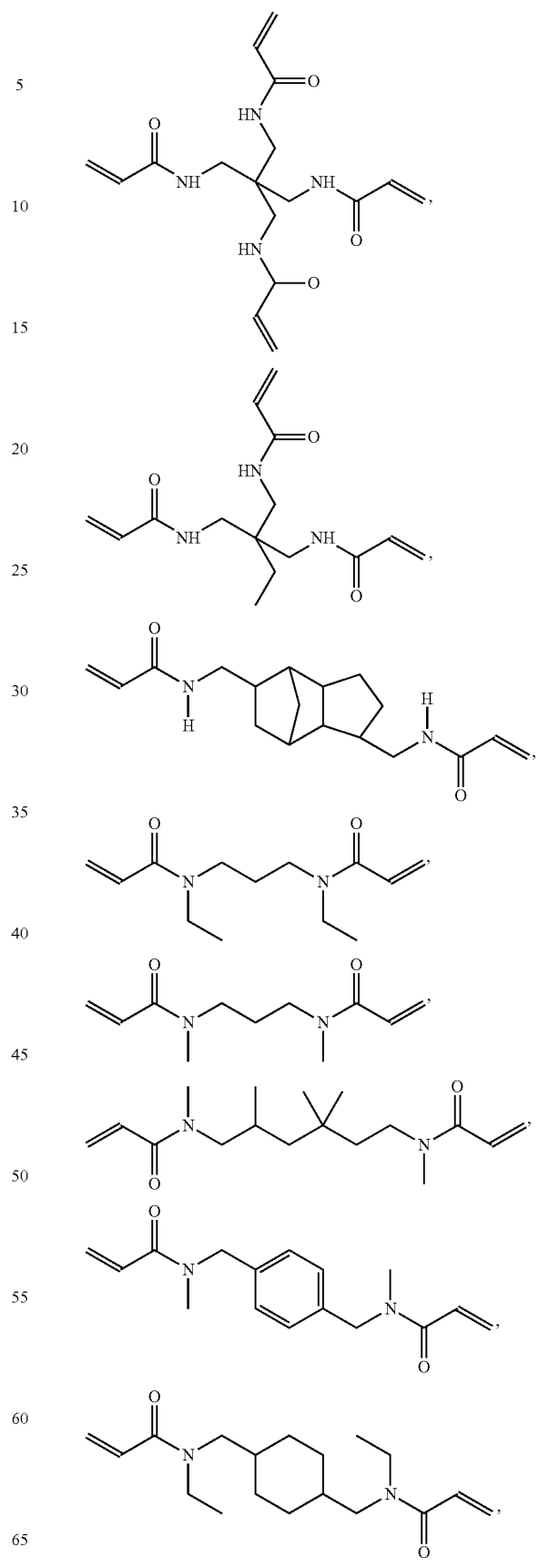

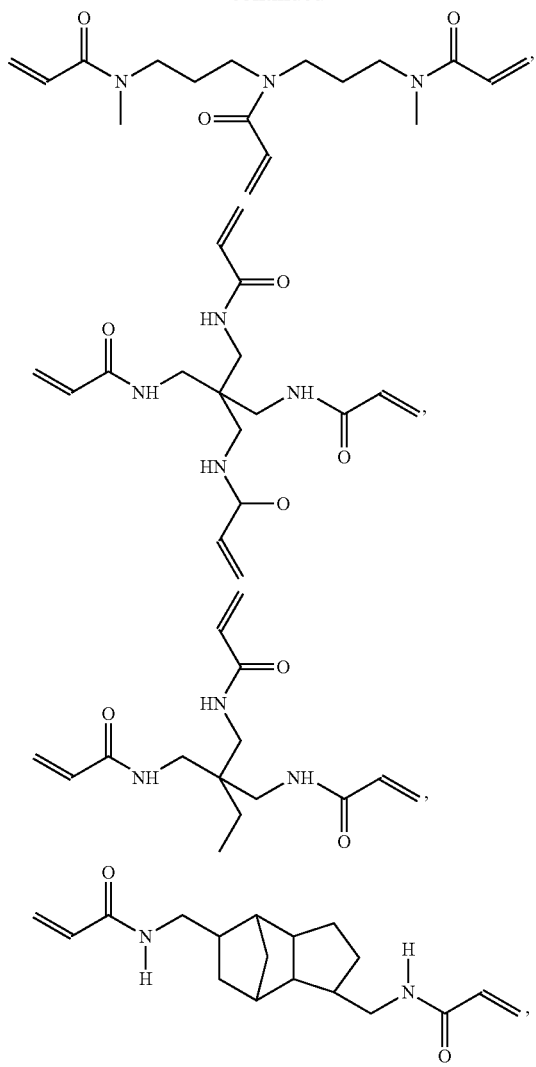
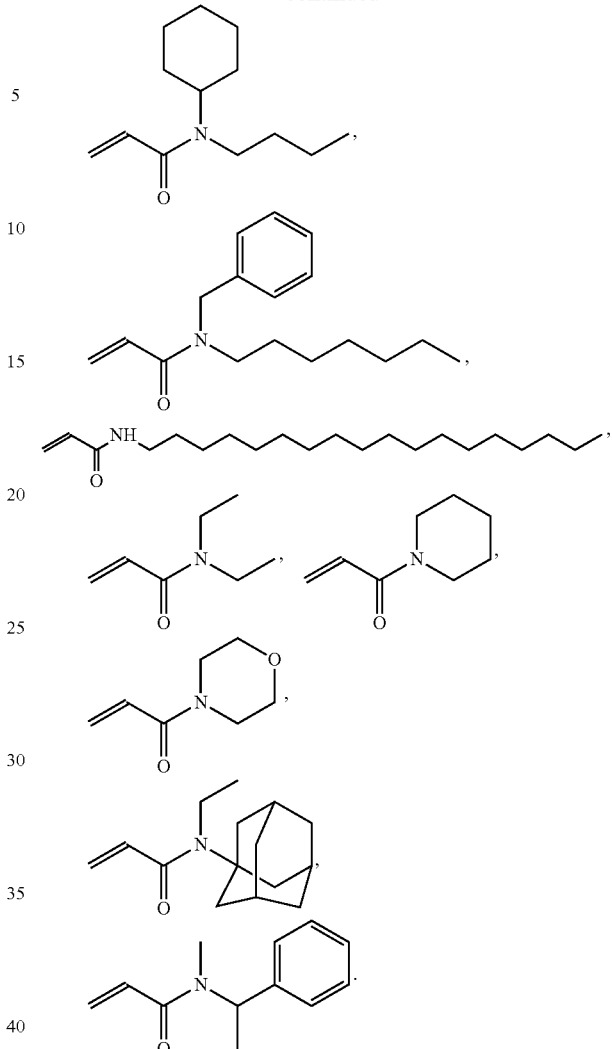
Most preferred are the bis-(meth)acrylamides:
N,N'-diallyl-1,4-bisacrylamido-(2E)-but-2-en (BAABE) having the structural formula
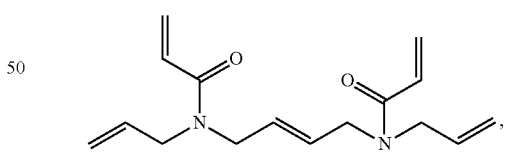
and
N,N'-diethyl-1,3-bisacrylamido-propan (BADEP) having the structural formula
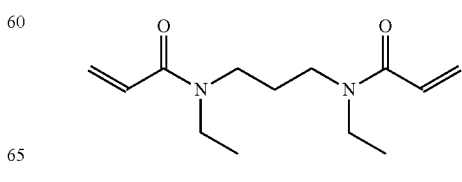

Further Components

Optionally, the light-curable dental impression material of the present invention may further comprise stabilizer(s), plasticizers, dyes/pigments and/or flavorants/sweeteners. Moreover, the light-curable dental impression material of the present invention may further comprise cationically polymerizable monomers.

The term "stabilizer" as used herein means any compound capable of preventing polymerizable compounds contained in the light-curable dental impression material from spontaneous polymerization during storage. However, the stabilizer does not disturb or prevent intended polymerisation curing of the light-curable dental impression material during application.

For example, the stabilizer may be a conventional stabilizer selected from the group consisting of hydroquinone, hydroquinone monomethylether, tent-butyl-hydroquinone, tert-butylhydroxyanisol, propyl gallate and 2,6-di-tert-butyl-p-cresol. From these conventional stabilizers, 2,6-di-tert-butyl-p-cresol is preferred. Furthermore, anaerobic stabilzers such TEMPO, phenothiazine, galvanoxyl radical may be used.

The light-curable dental impression material according to the invention may contain the stabilizer in an amount of 0.001 to 1 percent by weight, preferably 0.005 to 0.8 percent by weight based on the total weight of the composition. When the amount of the stabilizer is below the above indicated lower limit of 0.001, then storage stability of the light-curable dental impression material might be insufficient, since the amount of stabilizer is too small to provide a stabilizing effect. However, when the amount of stabilizer is above the maximum threshold of 1 percent by weight, then the applicability of the light-curable dental impression material might be negatively affected, since higher amounts of stabilizer may disturb or even substantially prevent intended polymerization curing of the light-curable dental impression material during application.

The light-curable dental impression material according to the invention may contain one or more plasticizers so as to improve the softness of impression material upon curing, reduce the affinity between cured impression and dental substrate, and enhance clean removal of the impression from dental substrate. Suitable plasticizers are nontoxic in the oral environment and may include, for example, mineral oils, vegetable oils, hydrogenated vegetable oils, silicone oils, phthalate derivatives such as dibutyl phthalate, diethyl phthalate and dioctyl phthalate, fatty alcohols, fatty (meth)acrylates, glycerin, glycerides, and other macromolecules such as polyethylene glycols, polypropylene glycols, polytetrahydrofurans, polyvinyl alcohols, polyether-modified polysiloxanes, xathan gum, cellulosepolyalkylene glycols and hydrocarbon waxes including their halogenated and/or hydrogenated derivatives.

The light-curable dental impression material may comprise 0.1 to 20 wt. % plasticizer, optionally 1 to 10 wt. % plasticizer, based on the total weight of the composition.

The dyes and pigments are selected in such a way that they render color to the light-curable dental impression material while imparting no or low absorption and scattering of the actinic light as measured by, for example, UV-Vis spectroscopy. Suitable dyes and pigments are soluble in the polymerizable resin matrix, or have a mean particle size in the range of from 0.05 to 75 μm as measured, for example, by electron microscopy or by using a conventional laser diffraction particle sizing method. In some embodiments, thermochromic pigments including leuco dyes and thermochromic liquid crystals are used that, upon heating at physiological temperatures, change from high-absorbance color to low-absorbance color within the wave length range of actinic light.

The light-curable dental impression material may comprise 1 ppm to 10% of dyes and/or pigments by weight, optionally 4 ppm to 5% by weight, based on the total weight of the composition.

According to a specific embodiment, the light-curable dental impression material according to the invention may include additional cationic polymerizable resins including a compound having one or more cationic polymerizable groups according to the following formula (XX).

$$(K)_o\!\!-\!\!R^{21} \qquad\qquad (XX)$$

wherein
K=cationicaliy polymerizable group
$R^{21}$=organic moiety
o≥1

Preferably, K represents a vinyl ether group, a vinyl ester group, a vinyl siloxane group, an epoxide group, an oxetane group and a furane group.

More preferably, K represents a vinyl ether group and a vinyl ester group, most preferably K represents a vinyl ether group.

Preferably, $R^{21}$ represents an o-valent $C_{1-30}$ hydrocarbyl groups which may contain 1-15 heteroatoms selected from O, S, Si, and which may be substituted by 1-15 substituents selected from $C_{1-4}$ alkyl groups, $C_{4-10}$ aryl groups, $C_{4-9}$ heteroaryl groups, halogen atoms, $C_{1-4}$ alkoxy groups, ester groups, thioether groups, silyi groups, and siloxane groups.

The hydrocarbyl group may be an alkyl group, a cycloalkyl group, a cycloalkylalkyl group, an arylalkyl group or an aryl group.

An alkyl group may be straight-chain or branched $C_{1-30}$ alkyl group, typically a $C_{1-6}$ alkyl group. Examples for a $C_{1-6}$ alkyl group can include linear or branched alkyl groups having 1 to 6 carbon atoms, preferably 1 to 4 carbon atoms, for example, methyl, ethyl, n-propyl, isopropyl, n-butyl, isobutyl, sec-butyl, tert-butyl, n-pentyl, isopentyl and n-hexyl.

A cycloalkyl group may be a $C_{3-20}$ cycloalkyl group, typically a $C_{3-8}$ cycloalkyl group. Examples of the cycloalkyl group can include those having 3 to 6 carbon atoms, for example, cyclopropyl, cyclobutyl, cyclopentyl and cyclohexyl.

A cycloalkylalkyl group may have 4 to 20 carbon atoms and may include a combination of a linear or branched alkyl group having 1 to 6 carbon atoms and a cycloalkyl group having 3 to 14 carbon atoms. Examples of the cycloalkylalkyl group can for example, include methylcyclopropyl, methylcyclobutyl, methylcyclopentyl, methylcyclohexyl, ethylcyclopropyl, ethylcyclobutyl, ethylcyclopentyl, ethylcyclohexyl, propylcyclopropyl, propylcyclobutyl, pro pyl-cyclopentyl, propylcyclohexyl.

An arylalkyl group may be a $C_{7-20}$ arylalkyl group, typically a combination of a linear or branched alkyl group having 1 to 6 carbon atoms and an aryl group having 6 to 10 carbon atoms. Specific examples of an arylalkyl group are a benzyl group or a phenylethyl group.

An aryl group can include aryl groups having 6 to 10 carbon atoms. Examples of the aryl group are phenyl and naphthyl.

The hydrocarbylcarbonyl groups of $R^{21}$ represent acyl groups ($R^{22}$-(C=O)-) in which the organic residue $R^{22}$ is a hydrocarbyl residue as defined above.

Preferably, the hydrocarbylcarbonyl group is an arylcarbonyl group, more preferably a benzoyl group.

Preferably, $R^{21}$ is selected from the group consisting of a straight chain or branched $C_{1-6}$ alkyl group, and a phenyl or benzoyl group which may optionally be substituted by one to three substitutents selected from halogen atoms, $C_{1-4}$ alkoxy groups.

Preferably, o is between 1 and 4, more preferably o is 2.

More preferably, the reactive diluent is a compound of the formula (XXI)

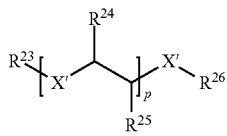

(XXI)

wherein
$R^{23}$ and $R^{26}$ which may be the same or different, independently represent a hydrogen atom, a $C_{1-4}$ alkyl group, a vinyl group, a vinyl silyl group, an epoxide group, an oxetane group, a furane group,
$R^{24}$ and $R^{25}$ which may be the same or different, independently represent a hydrogen atom, a $C_{1-4}$ alkyl group, or a vinyl ether group, a vinyl ester group, a vinyl siloxane group, an epoxide group, an oxetane group, a furane group,
X' represents an oxygen, a sulfur or a carbon atom,
p represents an integer of from 1 to 10,
provided that at least one cationic polymerizable group is present in the compound of formula (XXI).

In a preferable embodiment, X' represents an oxygen atom, $R^{24}$ represents a hydrogen atom, or a methyl group, $R^{25}$ represents a hydrogen atom, $R^{23}$ and $R^{26}$ represent vinyl groups, more preferable X' represents an oxygen atom, $R^{24}$ and $R^{25}$ represent a hydrogen atom, $R^{23}$ and $R^{26}$ represent vinyl groups.

A particular suitable reactive diluent is ethylene glycol vinyl ether.

The present invention also provides the use of the light-curable dental impression material according to the present invention for the preparation of a dental impression.

It was found that the acid residues in the raw material Silmer OH Di-10 (a hydroxyl-terminated siloxane) have a significant negative impact on the performance of the formulated composition from the polymerizable resin B derived from hydroxyl-terminated siloxanes. Due to the inconsistent quality of off the shelf/impure hydroxyl-terminated siloxane from the same manufacturer and/or different manufacturers, efforts were made to identify the root causes of such inconsistent quality of off the shelf/impure raw materials. Once the active impurities were identified, an effective process was developed to remove/clean up those active impurities in order to ensure good quality of hydroxyl-terminated siloxanes as well as performance of formulated composition from the polymerizable resin B derived from such treated hydroxyl-terminated siloxanes.

"off the shelf" and "impure" are used interchangeably.

The active impurities that were identified include allyl alcohol, aldehydes and acids, along with additional unidentified compounds. Generally high acid values of 0.25-0.55 mgKOH/g were found from such off the shelf hydroxyl-terminated siloxanes (Silmer OH Di-10 from Siltech or DMS-C16 from Gelest), which was designated as low quality hydroxyl-terminated siloxanes. It was also found that some off the shelf materials could readily turn into low quality hydroxyl-terminated siloxanes with increasing acid value, due to normal aging at room temperature.

Solid acid-absorbent materials were used to treat low quality hydroxyl-terminated siloxanes in order to ensure good quality of hydroxyl-terminated siloxanes.

In an embodiment, a light curable dental impression material having improved shore hardness and improved tear strength may be provided. The impression material comprises a polymerizable polysiloxane resin mixture obtained by a process comprising steps of:

(a) treating an impure dial compound of formula (Xa)

$$HO-L^4(OH) \quad (Xa)$$

wherein $L^4$ is a polysiloxane group of the formula (VIIIa)

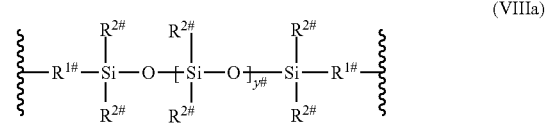

(VIIIa)

wherein
$R^{1\#}$ is an alkylene having 1 to 8 carbon atoms;
$R^{2\#}$ is an alkyl having from 1 to 4 carbon atoms; and
$y^\#$ is an integer from 5 to 20;
with a solid acid absorbent material to obtain purified compound of formula (Xa).

(b) reacting a mixture comprising:
(i) x equivalents of purified compound of formula (Xa) and one or more di- or polyol compounds of the following formula $$HO-L^{4''}(OH)_{l''} \quad (Xa')$$

wherein
$L^{4'''}$ is an (l''+1)-valent linker group; and
l'' is an integer of from 1 to 5,
(ii) y equivalents of one or more compounds of a following formula (XI):

$$OCN-L^3NCO \quad (XI)$$

wherein
$L^3$ is a divalent linker group of Formula (VI)

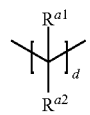

(VI)

wherein
$R^{a1}$ and $R^{a2}$ which may be a same or different, independently represent a hydrogen atom, a $C_{1-6}$ linear or branched alkyl group, a $C_{4-10}$ aryl group, a polymerizable double bond containing organic residue, a group of the following formula $[-X''L'']_m R^{a3}$, wherein X'' represents O, S, or $NR^{a4}$ wherein $R^{a4}$ represents a hydrogen atom, an organic residue containing a polymerizable double bond, a linear or branched $C_{1-6}$ alkyl group, or a $C_{4-10}$ aryl group, L" represents a $C_{1-6}$ linear or branched alkyl group, a $C_{4-10}$ aryl group, or a $SiR^{a5}{}_2$ group wherein $R^{a5}$ which may be a same or different, independently represent an organic residue containing a polymerizable double bond, or a $C_{1-4}$ alkyl group, preferably a methyl group, m is an integer from 1 to 20, and $R^{a3}$ is an organic residue containing a polymerizable double bond, a $C_{1-4}$ alkyl group, or a $C_{4-10}$ aryl group ; and (iii) z equivalents of one or more compounds of a following formula (XII):

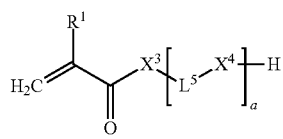

(XII)

wherein $R^1$ represents a hydrogen atom or a $C_{1-12}$ alkyl group;

$X^3$ represents an oxygen atom, a sulfur atom or a group $NR^2$, wherein $R^2$ is a hydrogen atom, $C_{1-12}$ alkyl group, or an allyl group;

$L^5$ is a divalent hydrocarbon linker group, preferably a $C_{2-20}$ alkylene group; and $X^4$ represents an oxygen atom, a sulfur atom or a group $NR^3$, wherein $R^3$ is a hydrogen atom, or a $C_{1-12}$ alkyl group, a represents an integer of from 1 to 20, wherein $0.05 \le x/y \le 0.66$, wherein x, y and z are the molar equivalents of component (a), (b) and (c)

to form the polymerizable polysiloxane resin mixture.

In one embodiment of the light curable dental impression material, the polymerizable polysiloxane resin composition comprises compounds of the following formula (I):

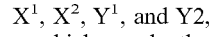

(I)

wherein the E which may be the same or different, independently represent a monovalent group selected from a group containing a polymerizable carbon-carbon double bond, a group containing a polysiloxane moiety, a $C_{2-20}$ alkoxy group, a $C_{2-20}$ thioalkyl group, and a RNH group, wherein R is a $C_{2-20}$ alkyl group;

$L^1$ which may be the same or different when more than one $L^1$ is present, represents a divalent group of the following formula (II):

(II)

wherein $L^3$ which may be the same or different when more than one $L^3$ is present, independently represents a divalent linker group which may be substituted with up to four substituents of the formula (III):

-$L^1$-E (III)

wherein $L^1$ and E are as defined above;

$L^4$ which may be the same or different when more than one $L^4$ is present, independently represents a divalent linker group which may be substituted with up to four substituents of the formula (III), wherein $L^1$ and E are as defined above;

$X^1$, $X^2$, $Y^1$, and Y2, which may be the same or different, and when more than one $X^1$, $X^2$, $Y^1$, or $Y^2$, is present, the $X^1$, $X^2$, $Y^1$, and $Y^2$ may be the same or different, independently represent an oxygen atom, a sulfur atom and a group NR', wherein R' is a hydrogen atom or a $C_{1-4}$ alkyl group;

m represents 0 or an integer of from 1 to 40;

Z represents a divalent linker group which may additionally be substituted with up to four substituents selected from polysiloxane groups and groups of the formula (III), wherein $L^1$ and E are as defined above;

$L^2$ represents a single bond or a divalent group of the formula (II), wherein $L^3$, $L^4$, $X^1$, $X^2$, $Y^1$, $Y^2$ and m are independently as defined for $L^1$;

n represents 0 or an integer of from 1 to 4;

provided that a compound of formula (I) contains at least one monovalent group E having a polymerizable carbon-carbon double bond, a compound of formula (I) contains at least one polysiloxane group, and provided that when n is 0, then $L^2$ is a divalent group of the formula (II);

In certain embodiment of the light curable dental impression material; $L^2$ and/or $L^3$ and/or $L^4$ independently represent a polysiloxane group of the following formula (VIIIa)

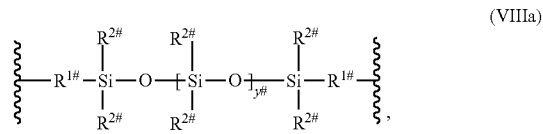

(VIIIa)

wherein $R^{1\#}$ is an alkylene having 1 to 8 carbon atoms;

$R^{2\#}$ is an alkyl having from 1 to 4 carbon atoms; and $y^{\#}$ is an integer from 5 to 20;

In one embodiment of the light curable dental impression material; the $L^{4'''}$ is a group formula (VII):

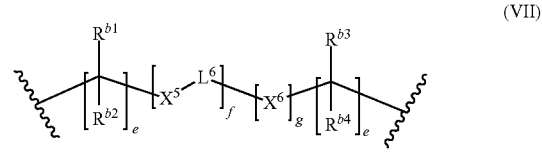

(VII)

wherein $R^{b1}$, $R^{b2}$, $R^{b3}$ and $R^{b4}$ ; which is a same or different, independently represent a hydrogen atom, a $C_{1-6}$ linear or branched alkyl group, a $C_{4-10}$ aryl group, a polymerizable double bond containing organic residue, a group of the following formula $[-X'''L''']_m R^{b5}$, wherein X''' represents O, S, or $NR^{b6}$ wherein $R^{b6}$ represents a hydrogen atom, an organic residue containing a polymerizable double bond, a linear or branched $C_{1-6}$ alkyl group, or a $C_{4-10}$ aryl group, L'" represents a $C_{1-6}$ linear or branched alkyl group, a $C_{4-10}$ aryl group, or a $SiR^{b7}_2$ group wherein $R^{b7}$ which is a same or different, independently represent an organic residue containing a polymerizable double bond or a $C_{1-4}$ alkyl group, m is an integer from 1 to 20, and $R^{b5}$ is an organic residue containing a polymerizable double bond, a $C_{1-4}$ alkyl group or a $C_{4-10}$ aryl group;

$X^5$ and $X^6$ which is a same or different, and when more than one $X^5$ or $X^6$, are present, the $X^5$ and $X^6$ is the same or different, independently represent an oxygen atom, a sulfur atom and a group $NR^N$, wherein $R^N$ is a hydrogen atom or a $C_{1-4}$ alkyl group;

$L^6$ is a divalent hydrocarbon linker group;

e is an integer of from 1 to 10;

f is an integer of from 1 to 100; and g is 0 or 1;

According to a preferred embodiment, the group $-[L^6-X^5]-$ is selected from the following groups:

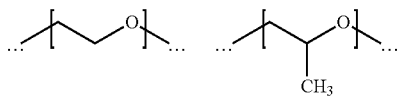

In an embodiment of the light curable dental impression material, $L^3$ is selected from the following groups:

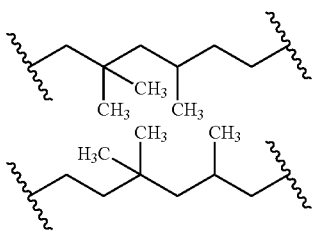

In one aspect, a process is provided for preparing a polymerizable polysiloxane resin mixture. The process includes the following steps:

(a) treating an impure diol compound of formula (Xa)

$$\text{HO-L}^4(\text{OH}) \quad \text{(Xa)}$$

wherein $L^4$ is a polysiloxane group of the formula (VIIIa)

 (VIIIa)

wherein $R^{1\#}$ is an alkylene having 1 to 8 carbon atoms;

$R^{2\#}$ is an alkyl having from 1 to 4 carbon atoms; and $y^\#$ is an integer from 5 to 20;

with a solid acid absorbent material to obtain purified compound of formula (Xa).

(b) reacting a mixture comprising:

(i) x equivalents of purified compound of formula (Xa) and one or more di or polyol compounds of the following formula $$\text{HO-L}^{4\prime\prime}(\text{OH})_{l\prime\prime} \quad \text{(X)}$$

wherein $L^{4\prime\prime}$ is an (l"+1)-valent linker group; and l" is an integer of from 1 to 5, (ii) y equivalents of one or more compounds of a following formula (XI):

$$\text{OCN-L}^3\text{NCO} \quad \text{(XI)}$$

wherein $L^3$ is a divalent linker group of Formula (VI)

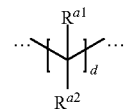 (VI)

wherein $R^{a1}$ and $R^{a2}$ which may be a same or different, independently represent a hydrogen atom, a $C_{1-6}$ linear or branched alkyl group, a $C_{4-10}$ aryl group, a polymerizable double bond containing organic residue, a group of the following formula $[-X''L'']_m R^{a3}$, wherein X" represents O, S, or $NR^{a4}$ wherein $R^{a4}$ represents a hydrogen atom, an organic residue containing a polymerizable double bond, a linear or branched $C_{1-6}$ alkyl group, or a $C_{4-10}$ aryl group, L" represents a $C_{1-6}$ linear or branched alkyl group, a $C_{4-10}$ aryl group, or a $SiR^{a5}_2$ group wherein $R^{a5}$ which may be a same or different, independently represent an organic residue containing a polymerizable double bond, or a $C_{1-4}$ alkyl group, preferably a methyl group, m is an integer from 1 to 20, and Rai is an organic residue containing a polymerizable double bond, a $C_{1-4}$ alkyl group, or a $C_{4-10}$ aryl group; and (iii) z equivalents of one or more compounds of a following formula (XII):

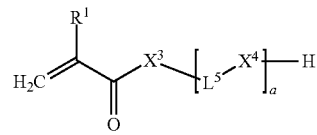 (XII)

wherein $R^1$ represents a hydrogen atom or a $C_{1-12}$ alkyl group;

$X^3$ represents an oxygen atom, a sulfur atom or a group $NR^2$, wherein $R^2$ is a hydrogen atom, $C_{1-12}$ alkyl group, or an allyl group;

$L^5$ is a divalent hydrocarbon linker group, preferably a $C_{2-20}$ alkylene group;

$X^4$ represents an oxygen atom, a sulfur atom or a group $NR^3$, wherein $R^3$ is a hydrogen atom, or a $C_{1-12}$ alkyl group; and a represents an integer of from 1 to 20, wherein $0.05 \leq x/y \leq 0.66$, wherein x, y and z are the molar equivalents of component (a), (b) and (c)

to form the polymerizable polysiloxane resin mixture.

Figure 5:
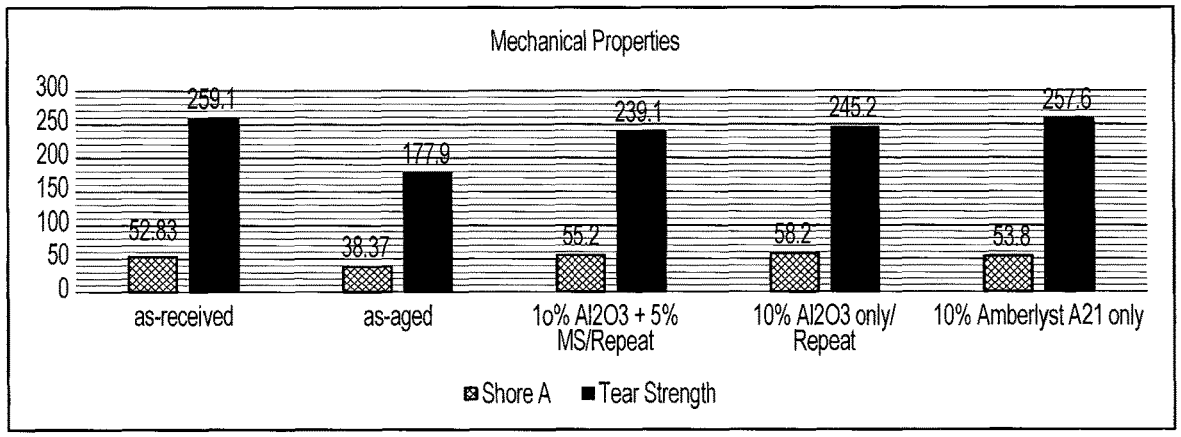
FIG. 5 shows a chart representing treatment effects of Silmer/lot 11801005 on mechanical properties of Combo Resins.
Figure 6:
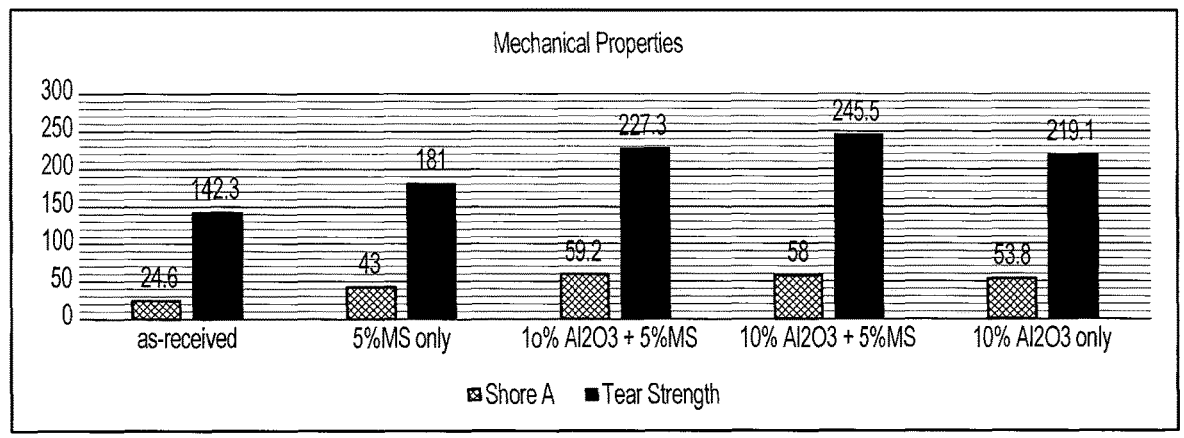
FIG. 6 shows a chart representing treatment effects of Silmer/lot11804022 on mechanical properties of Combo Resins.

Examples of solid acid-absorbent materials may include activated basic alumina oxide ($Al_2O_3$), molecular sieve (MS), weak basic ion-exchange resin such as Amberlyst A21 or combination thereof. Activated basic alumina oxide ($Al_2O_3$) and molecular sieve (MS) were used to treat low quality hydroxyl-terminated siloxanes such as silmer monomers with acid value of 0.234-0.297 mgKOH/g (lot#11801005 and lot# 11804022). There was not only significant reduction in total acid value from 0.234-0.297 mgKOH/g to 0.056 mgKOH/g but also increased pH (as evident from Table 15, 16 and 17). More importantly, the polymerizable urethane-polyether-siloxane copolymer could offer significantly enhanced mechanical properties, such as Shore A Harness and Tear Strength, respectively, in its formulated compositions (as depicted in FIGS. 5 and 6). The compositions were formulated as pastes with 15% wt/wt of filler mix and cured with LED curing pad.Tear strength was tested by using OLD test method (see the details in test method description).

The solid acid-absorbent material is added in an amount of from 1-10% wt/wt based on total weight of the off the shelf/impure hydroxyl-terminated siloxanes; alternatively from 1-5% based on total weight of the off the shelf hydroxyl-terminated siloxanes. 5-10%, wt/wt of such basic $Al_2O_3$ were found to work well. Molecular sieve is optional to reduce total moisture during such treatment. It was also demonstrated weak basic ion-exchange resin, Amberlyst A21, also work well to remove acidic impurities from low quality hydroxyl-terminated siloxane to allow them to regain good mechanical properties. Such effectiveness is evident by reduced low acid value (<0.06 mgKOH/g) to achieve higher pH (>4.0); complete removal of allyl alcohol; regained high reactivity in urethane reactions with increased exothermic temperature; consistent results of good mechanical properties for formulated IRON Pastes from Resin B derived from such pretreated Silmer monomers.

The present invention will now be further illustrated based on the following examples.

EXAMPLES

Typical compositions and processes to siloxane-modified Genesis Resin (FIG. 1A and FIG. 1B) and PEGMA-modified Genesis Resin:

Preparation Example 1

Siloxane-Modified Genesis Resin (FIG. 1A and FIG. 1B):

The following raw materials were used.

| Raw Material | Formula | Mn/g/mol |
|---|---|---|
| Poly(ethylene glycol) methacrylate | 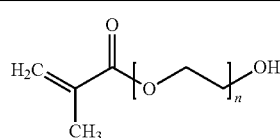 | ~360<br>~500 |
| TMDI |  | 210 |
| Voranol 2120 | 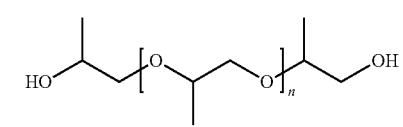 | 2000<br>4000 |
| Hydroxyl-terminated Siloxane (Carbinol 1K) | 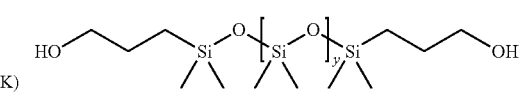 | 1000 |
| bismuth 2-ethyl hexanoate K-KAT 348 | 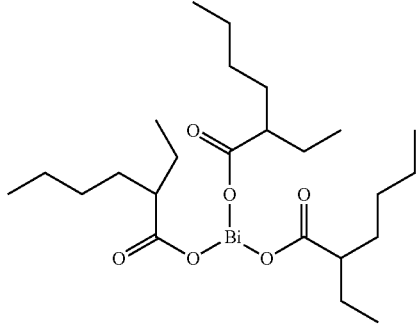 | |

Dry air was purged through a 1000 mL resin reaction kettle and the jack temperature was set at 50° C. Trimethyl hexamethylene diisocyanate (TMDI)(121.7 g, 0.58 mol) was added to the reaction kettle, followed by addition of Voranol- 220-028 (466.8 g, 0.12 mol), and then Silmer monomer (284.0 g, 0.29 mol), and 0.31 g of urethane catalyst (K-Kat®348, a Bismuth Carboxylate from King Industries) into the reaction system. The reaction was kept for additional 2-3 hours. Then sample was taken for analysis by FTIR and NMR to make sure all of hydroxyl group got reacted prior to proceeding to the next step. PEGMA (116.6 g, 0.32 mol) was added slowly to the reaction system for 30 min. The reaction was maintained at 50° C. for another 2 hours. Then 1-dodecanol (118.2 g, 0.10 mol) was added slowly into the system. The reaction was kept at 50° C. overnight, then butylated hydroxy toluene (BHT) (0.4 g) was added to the system prior to discharge. Sampling was made for FTIR and NMR. The resin was placed in 45° C. to clear out all the trapped air bubbles. Viscosity of 11Pa.s @25° C. resulted with MA content as 0.32 mmol/g and siloxane content as 28.2% wt/wt.

Examples 2 to 14

In a similar manner as described in Preparation Example 1, further siloxane-modified polyether-urethane dimethacrylate macromonomers were prepared.

The composition and properties of macromonomers of Preparative Examples 1 to 14 are as shown in the following Tables 1 and 2

TABLE 1

Compositions of Siloxane-modified Polyether-urethane Dimethacrylate Macromonomers

| Examples | Batch Size (grams) | Reaction Sequence (stepwise) | Voranol 2K/4K (grams) (mole) | DMS-C16 DMS-C21 (grams) | TMDI (grams) | K-KAT348 (ppm) | PEGMA 400 (grams) (mole) | Viscosity @25° C. (Pa · s) | MA Content mmol/g |
|---|---|---|---|---|---|---|---|---|---|
| 1 | 1213 | Voranol 2K/4k to TMDI | 300.0 0.1500 205.7 0.0514 | DMS-C21 450 0.100 | 105.45 0.5012 | 0.33 270 | 151.4 0.4205 | 34 opaque | 0.35 |
| 2 | 870 | Voranol 4k to TMDI | 401.80 0.1002 | DM5-C16 145.3 0.207 | 105.30 0.2010 | 0.30 340 | PE-350 193.3 0.537 | 14 Clear got gelled in 3 wksRT | 0.58 |
| 3 | 1028 | Voranol 2K to TMDI | 500.8 0.2500 | DMS-C21 250 0.0500 | 105.60 0.5000 | 0.33 320 | 172.0 0.47 | 20 opaque | 0.46 |
| 4 | 816 | Voranol 4k to TMDI | 400.4 0.100 | DMS-C16 140.0 0.200 | 106.6 0.0501 | 0.33 340 | 170.0 0.47 | 12 slightly hazy | 0.58 |
| 5 | 1035 | Voranol 2K/4Lk to TMDI | 315.0 0.1575 360 0.090 | DMS-C21 113 0.0225 | 95.0 0.450 | 0.33 320 | 170.0 0.47 | 24 opaque | 0.41 Silox 10.9% |
| 6 | 695 | Voranol 2k/4k to TMDI | 120.0 0.060 160.0 0.040 | DMS-C16 140.0 0.200 | 105.5 0.050 | 0.33 340 | 170.0 0.47 | 12 slightly hazy | 0.68 Silox 20.1% |
| 7 | 796 | Voranol 4k to TMDI | 400.0 0.100 | DMS-C16 175.0 0.250 | 105.5 0.050 | 0.33 340 | 100.0 0.47 C12OH 0.08 | 14 slightly hazy | 0.35 Silox 22.0% |

TABLE 2

Compositions of Siloxane-modified Polyether-urethane Dimethacrylate Macromonomers

| Resin Code | Batch Size (grams) | Reaction Sequence (stepwise) | Voranol 2K (grams) (mole) | Silmer OH Di-10 (grams) | TMDI (grams) | K-KAT348 (ppm) | PEGMA 400 (grams) (mole) | Viscosity @25° C. (Pa · s) | MA Content mmol/g |
|---|---|---|---|---|---|---|---|---|---|
| 8 | 875 | Three-steps: V4k/HTSi/TMDI PEGMA C12OH | 400.1 0.100 | 255.0 0.250 | 105.56 0.50 | 0.33 340 | 100.0 0.278 15.0 0.08 | 12 clear | 0.318 Silox 20.0% |
| 9 | 890 C12OH-free | Two-steps: V4k/HTSi/TMDI PEGMA | 400.1 0.100 | 255.0 0.250 | 105.56 0.50 | 0.33 340 | 129.0 0.358 | 13 clear | 0.402 Silox 28.6% |
| 10 | 1003 | Three-steps: V4k/HTSi/TMDI PEGMA C12OH | 463.8 0.116 | 282.1 0.277 | 121.7 0.579 | 0.30 300 | 116.6 0.324 17.3 0.09 | 11 clear | 0.323 Silox 20.0% |
| 11 | 1007 | Three-steps: V4k/HTSi/TMDI PEGMA C12OH | 466.8 0.117 | 284.0 0.278 | 121.8 0.579 | 0.30 300 | 116.6 0.324 18.2 0.10 | 11 clear | 0.322 Silox 20.0% |
| 12 | 1006 Low Temp. | Three-steps: V4k/HTSi/TMDI PEGMA C12OH | 464.9 0.116 | 285.6 0.280 | 121.9 0.579 | 0.32 320 | 116.1 0.324 17.0 0.09 | 13 clear | 0.322 Silox 20.0% |

TABLE 2-continued

Compositions of Siloxane-modified Polyether-urethane Dimethacrylate Macromonomers

| Resin Code | Batch Size (grams) | Reaction Sequence (stepwise) | Voranol 2K (grams) (mole) | Silmer OH Di-10 (grams) | TMDI (grams) | K-KAT348 (ppm) | PEGMA 400 (grams) (mole) | Viscosity @25° C. (Pa · s) | MA Content mmol/g |
|---|---|---|---|---|---|---|---|---|---|
| 13 | 1006 Dosing | Three-steps: V4k/TMDI + HTSi PEGMA C12OH | 464.9 0.116 | 285.6 0.280 | 121.9 0.579 | 0.32 320 | 116.1 0.324 17.0 0.09 | 15 clear | 0.322 Silox 20.0% |
| 14 | 1006 Low Cat. | Three-steps: V4k/HTSi + TMDI PEGMA C12OH | 464.9 0.116 | 285.6 0.280 | 121.9 0.579 | 0.21 210 | 116.1 0.324 17.0 0.09 | 13 clear | 0.322 Silox 20.0% |

Example 15 (Reference)

PEGMA-modified Genesis Resin as additional polymerizable macromonomers (FIG. 2):
The following raw materials were used.

| Raw Material | Formula | Mn/ g/mol |
|---|---|---|
| Poly(ethylene glycol) methacrylate | 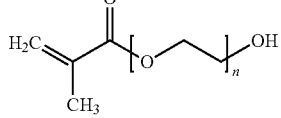 | ~360 ~500 |
| TMDI | 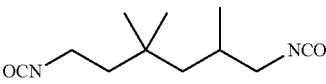 | 210 |
| Voranol 2120 | 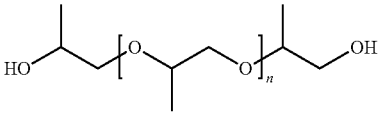 | 2000 4000 |
| bismuth 2-ethyl hexanoate K-KAT 348 | 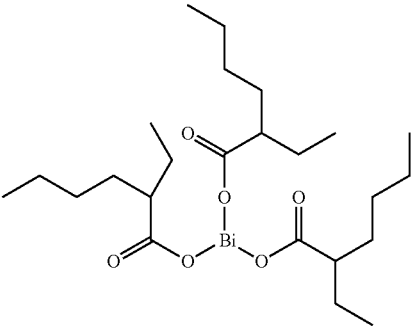 | |

Dry air was purged through a 1000 mL resin reaction kettle and the jack temperature was set at 50° C. Trimethyl hexamethylene diisocyanate (TMDI) (105.35 g, 0.50 mol) was added to the reaction kettle, followed by addition of Voranol 220-056 (400.4 g, 0.20 mol, Voranol 220-028 (400.6 g, 0.10 mol) and 0.304 g of urethane catalyst (K-Kat®348, a Bismuth Carboxylate from King Industries) into the reaction system. The reaction was kept for additional 2-3 hours. Then sample was taken for analysis by FTIR and NMR to make sure all of hydroxyl group got reacted prior to proceeding to the next step. PEGMA (161.9 g, 0.45 mol) was added slowly to the reaction system for 60 min. The reaction was kept at 50° C. overnight, then 0.4 g of BHT was added to the system prior to discharge. Sampling was made for FTIR and NMR. The resin was placed in 45° C. to clear out all the trapped air bubbles. Viscosity of 24 Pa.s @25° C. was resulted with MA content as 0.42 mmol/g.

Reference Examples 16 to 39

In a similar manner as described in Reference Example 15, further PEGMA-modified polyether-urethane dimethacrylate macromonomers were prepared.

The composition and properties of macromonomers of Reference Examples 15 to 39 are as shown in the following Tables 3 and 4

TABLE 3

Compositions of PEGMA-modified Polyether-urethane Dimethacrylate Oligomers

| Examples | Batch Size (grams) | Reaction Sequence (stepwise) | Voranol 2K (grams) (mole) | TMDI (grams) | K-KAT348 (grams) (ppm) | PEGMA-400 (grams) (mole) | 4EG Diol (grams) (mole) | Viscosity @25° C. (Pa · s) | MA Content mmol/g |
|---|---|---|---|---|---|---|---|---|---|
| 15 | 862 | Voranol 2K to TMDI | 545.95 0.2730 | 114.85 0.5462 | 0.1302 150 | 201.59 0.56 | | 13 clear | 0.65 |
| 16 | 810 | Voranol 2K to TMDI | 546.03 0.2730 | 114.93 0.5466 | 0.1305 160 | 129.73 0.3604 | 19.42 0.1000 | 35 clear | 0.44 |

TABLE 3-continued

Compositions of PEGMA-modified Polyether-urethane Dimethacrylate Oligomers

| Examples | Batch Size (grams) | Reaction Sequence (stepwise) | Voranol 2K (grams) (mole) | TMDI (grams) | K-KAT348 (grams) (ppm) | PEGMA-400 (grams) (mole) | 4EG Diol (grams) (mole) | Viscosity @25° C. (Pa·s) | MA Content mmol/g |
|---|---|---|---|---|---|---|---|---|---|
| 17 | 814 | Voranol 2K to TMDI | 545.594 0.2730 | 114.80 0.5460 | 0.1341 160 | 134.61 0.374 | 19.41 0.1000 | 37 clear | 0.44 |
| 18 | 814 | Voranol 2K to TMDI | 545.76 0.2730 | 114.89 0.5464 | 0.2010 245 | 134.11 0.3725 | 19.50 0.1004 | 42 clear | 0.44 |
| 19 | 795 | Voranol 2K to TMDI | 545.74 0.2730 | 114.76 0.5457 | 0.1972 250 | 134.42 0.3734 | | 14 clear | 0.46 |
| 20 | 800 | Voranol 2K to TMDI | 546.71 0.2729 | 114.75 0.5457 | 0.3032 380 | 129.41 0.3595 | BDO 9.03 0.1002 | 64 clear | 0.45 |
| 21 | 800 | Voranol 2K to TMDI | 545.93 0.2730 | 114.73 0.5456 | 0.3025 380 | 215.72 0.5992 | | 11 slightly hazy/noodor | 0.68 |
| 22 | 878 | Voranol 2K to TMDI | 546.93 0.2730 | 114.84 0.5461 | 0.3022 340 | 129.81 0.3606 | BDO 8.99 0.0998 | 62 clear | 0.45 |
| 23 | 950 | Voranol 2K to TMDI | 660.02 0.3300 | 114.83 0.5460 | 0.2980 250 | 174.94 0.4859 | | 24 clear | 0.51 |
| 24 | 945 | Voranol 2K to TMDI | 660.2 0.3301 | 114.74 0.5455 | 0.3031 320 | PEM6 LD 169.94 0.486 | | 26 clear strong odor | 0.51 |
| 25 | 1053 | Voranol 2K to TMDI | 659.77 0.3296 | 114.79 0.5459 | 0.3112 300 | PEM63P 277.91 0.5151 | | 15 Clear/ strong odor | 0.49 |
| 26 | 815 | Voranol 2K to TMDI | 545.89 0.2729 | 114.85 0.5462 | 0.3215 390 | PEGMA400 139.52 0.3876 | Isosorbide 14.59 0.0998 | 60 clear | 0.48 |
| 27 | 815 | Voranol 2K to TMDI | 546.12 0.2721 | 114.93 0.5466 | 0.3205 390 | PEGMA400 139.51 0.3875 | Isosorbide 14.60 0.0999 | 60 clear | 0.48 |
| 28 | 1012 | Voranol 2K to TMDI | 639.89 0.3199 | 134.78 0.6410 | 0.1609 160 | PEGMA400 237.16 0.6588 | | 13 clear | 0.65 |
| 29 | 1012 | Voranol 2K to TMDI | 639.75 0.3199 | 134.81 0.6411 | 0.1623 160 | PEGMA400 237.42 0.6595 | | 13 clear | 0.65 |
| 30 | 1005 | Voranol 2K to TMDI | 639.35 0.3197 | 134.56 0.6400 | 0.1661 165 | PEM6 LD 230.65 0.659 | | 12 clear strong odor | 0.66 |

TABLE 4

Compositions of PEGMA-modified Polyether-urethane Dimethacrylate Oligomers

| Examples | Batch Size (grams) | Reaction Sequence (stepwise) | Voranol 2K (grams) (mole) | TMDI (grams) | K-KAT348 (grams) (ppm) | PEGMAs (grams) (mole) | Chain Extnder (grams) (mole) | Viscosity @25° C. (Pa·s) | MA Content mmol/g |
|---|---|---|---|---|---|---|---|---|---|
| 31 | 1012 | TMDI to Voranol 2K | 639.93 0.3200 | 134.68 0.6405 | 0.1652 160 | PEGMA400 237.55 0.6599 | | 25 clear | 0.65 |
| 32 | 1005 | All-in-One | 640.02 0.2730 | 134.66 0.5460 | 0.1641 160 | PEM6 LD 230.65 0.659 | | 7 clear strong odor | 0.66 |
| 33 | 1012 | All-in-One | 640.13 0.3201 | 134.80 0.6411 | 0.1604 160 | PEGMA 400 237.03 0.6584 | | 6 clear | 0.65 |
| 34 | 970 | Voranol 4K to TMDI | 799.92 0.2000 | 63.13 0.3002 | 0.2611 270 | PE-350 107.05 0.2499 | | 19 clear | 0.26 |
| 35 | 930 | Voranol 4K to TMDI | 800.12 0.2000 | 57.85 0.2751 | 0.2539 270 | PEGMA 400 71.80 0.1994 | | 57 clear | 0.22 |
| 36 | 770 | Voranol 2K/4k to TMDI | 160.14 0.0801 479.99 0.1200 | 60.04 0.2855 | 0.2511 330 | PEGMA 400 68.44 0.1901 | | 60 clear | 0.25 |
| 37 | 770 | Voranol 2K/4k to TMDI | 159.99 0.080 480.18 0.1200 | 59.92 0.2850 | 0.2590 340 | PEGMA 400 68.63 0.1906 | | 59 clear | 0.25 |

TABLE 4-continued

Compositions of PEGMA-modified Polyether-urethane Dimethacrylate Oligomers

| Examples | Batch Size (grams) | Reaction Sequence (stepwise) | Voranol 2K (grams) (mole) | TMDI (grams) (mole) | K-KAT348 (grams) (ppm) | PEGMAs (grams) (mole) | Chain Extnder (grams) (mole) | Viscosity @25° C. (Pa · s) | MA Content mmol/g |
|---|---|---|---|---|---|---|---|---|---|
| 38 | 1012 | Voranol 2K to TMDI | 639.83 0.3199 | 134.50 0.6396 | 0.1624 160 | PEGMA 400 237.73 0.6604 | | 12 clear | 0.65 |
| 39 | 930 | All-in-One 2-steps | 540.05 0.2700 | 134.67 0.6404 | 0.1673 180 | PEGMA 400 237.44 0.6596 | Monolaurin 13.64 0.0497 | 12 clear | 0.71 |

Examples 40 to 50

The effect of the molecular weight of carbinols on the appearance of the siloxane-modified macromonomers was investigated. The results are summarized in Table 5.

TABLE 5

Effect of Molecular Weight of Carbinols on Appearance of Siloxane-modified Genesis Resins

| Examples | Siloxane Segments | Voranol Segments | Siloxane Content %, wt/wt | MA Content mmol/g | Viscosity @25° C. Pa · s | Appearance |
|---|---|---|---|---|---|---|
| 40 | DMS-C21 5000 | Voranol 2K Voranol 4K (1.5/1) | 37.3 | 0.35 | 34 | white opaque |
| 41 | DMS-C16, 600-850 | Voranol 4K | 16.7 | 0.54 | 14 | hazy and gelled |
| 42 | DMS-C21/ 5000 | Voranol 2K | 24.4 | 0.46 | 25 | white opaque |
| 43 | DMS-C16, 600-850 | Voranol 4K | 17.2 | 0.58 | 12 | slightly hazy |
| 44 | DMS-C21 5000 | Voranol 2K Voranol 4K (0.875/1) | 10.9 | 0.41 | 24 | opaque |
| 45 | DMS-C16, 600-850 | Voranol 2K Voranol 4K (0.75/1) | 20.1 | 0.68 | 12 | slightly hazy |
| 46 | DMS-C16, 600-850 | Voranol 4K | 22.0 | 0.35 | 14 | slightly hazy |
| 47 | DMS-C16, 600-850 | Voranol 4K | 14.5 | 0.29 | 16 | slightly hazy |
| 48 | DBE-C25 4000 | Voranol 2K | 8.4 | 0.43 | 22 | hazy gel-like |
| 49 | DBE-C25 4000 | Voranol 2K | 13.1 | 0.41 | 16 | hazy gel-like |
| 50 | none | Voranol 2K Voranol 4K (1/1) | 0 | 0.29 | 11 | clear |

Examples 51 to 53 (Reference)

Figure 3:
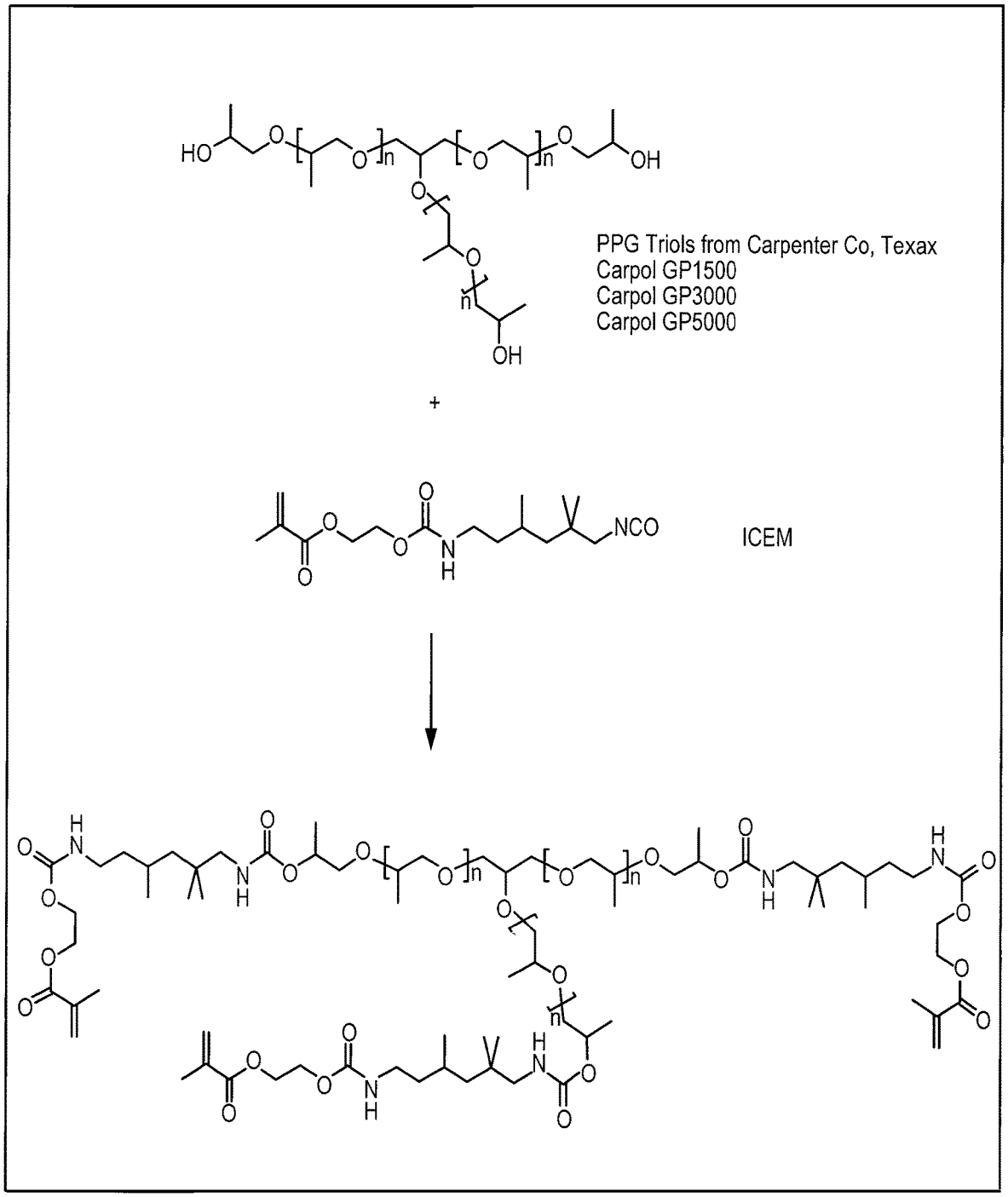
FIG. 3 shows a scheme of a reaction pathway towards high molecular weight cross-linkers having three or more polymerizable groups, which may be used in combination with the compounds according to formula (I).
Figure 4:
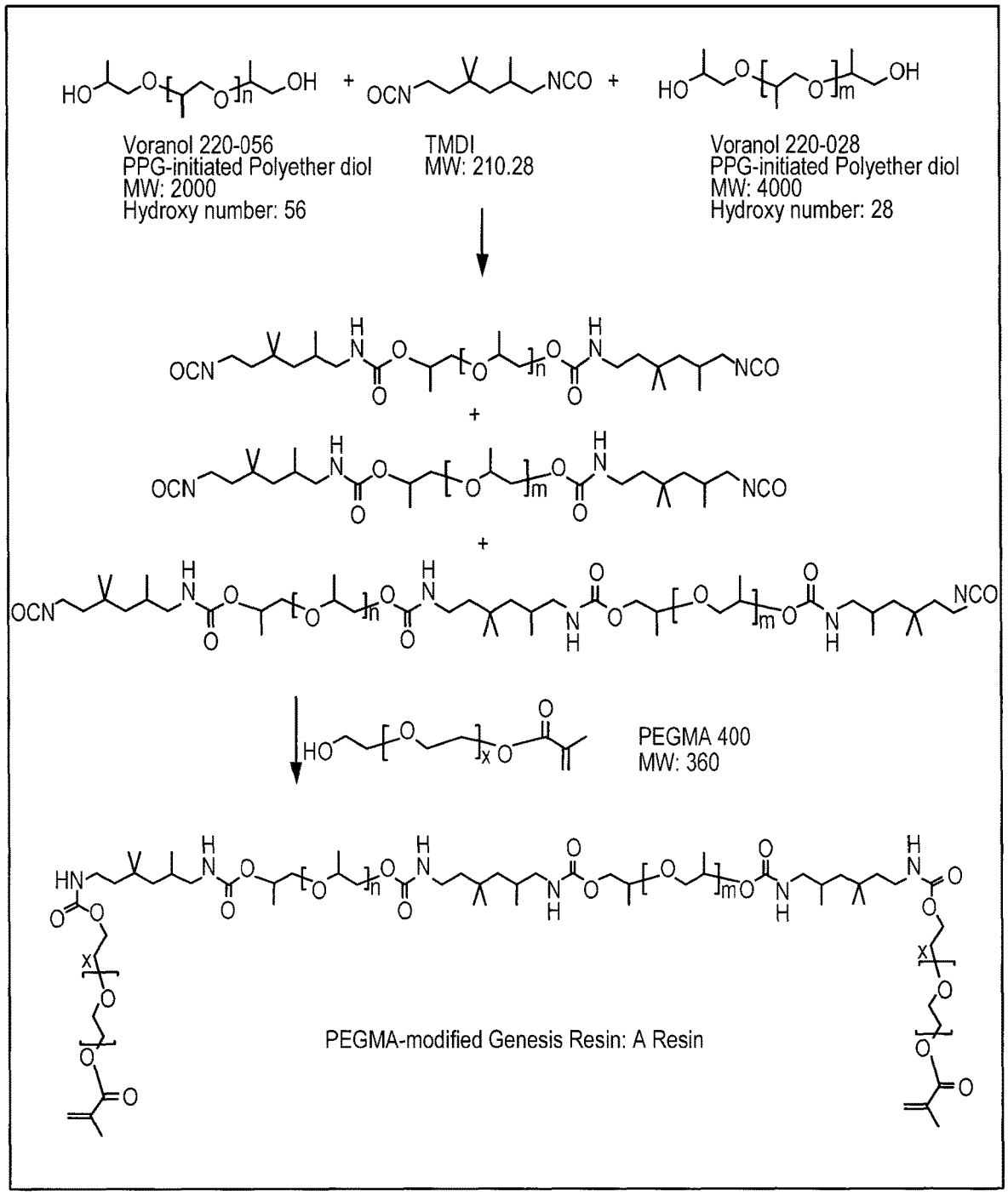
FIG. 4 shows a scheme of a reaction pathway towards further macromonomers which may be used in combination with the compounds according to formula (I).

Further additional polymerizable macromonomers in the form of trimethacrylated polyethers derived from Carpol triols were prepared as high molecular weight crosslinkers in accordance with the scheme shown in FIG. 3. The composition and properties of the additional polymerizable macromonomers are summarized in Table 6.

TABLE 6

Composition and Viscosity of triMethacrylated Polyethers derived from Carpol Triols

| Examples | Carpol G1500 (grams) | Carpol G3000 (grams) | Carpol G5000 (grams) | ICEM (grams) | K-KAT 348 (grams) | Viscosity Pa · S@25° C. | MA Content mmol/g |
|---|---|---|---|---|---|---|---|
| 51 | 0 | 0 | 765 | 153 | 0.35 | 24 | 1.17 |
| 52 | 0 | 612 | 0 | 204 | 0.35 | 62 | 0.73 |
| 53 | 550 | 0 | 0 | 368 | 0.35 | 101 | 0.49 |

Reference Examples 54 to 85 (FIG. 2, 4)

Standard Genesis Resin with T-9 via TMDI to Voranol Process (T2V)

Dry air was purged through a 1000 mL resin reaction kettle and the jack temperature was set at 50° C. Voranol-220-056 (545.01 g, 0.2726 mol) and urethane catalyst (T-9) (0.12 g) was added to the reaction kettle. Thereafter, trimethyl hexamethylene diisocyanate (TMDI) (114.22 g, 0.5431 mol) was charged into an additional funnel and started adding slowly into the reaction system through 2 hours. Then sample was taken for analysis by FTIR and NMR. HEMA (28.6 g) was added to the reaction system in 30 min, then 34.47 g of 1,4-butanediol (BDO) was charged into the system in 30 min too. The reaction was kept for 1 hr at 50° C., TIM preblend (ICEM) (65.01 g) was added in 30 min and it was kept further for overnight reaction at 50° C., finally additional 13.7 g of HEMA was added into the system. The reaction was kept in mixing at 50° C. overnight. BHT (0.4 g) was added to the system prior to discharge. Sampling was made for FTIR and NMR. The resin was placed in 45° C. to clear out all the trapped air bubbles. Viscosity of 55 Pa.s@25° C. was resulted.

Standard Genesis Resin with K-KAT via TMDI to Voranol Process (T2V)

Dry air was purged through a 1000 mL resin reaction kettle and the jack temperature was set at 50° C. Voranol-220-056 (546.27 g, 0.2732 mol) and 0.14 g of urethane catalyst (K-Kat®348, a bismuth carboxylate from King Industries) was added to the reaction kettle. Then trimethylhexamethylene diisocyanate (TMDI) (114.65 g, 0.5452mol) was charged into an additional funnel and started adding slowly into the reaction system through 2 hours. Then sample was taken for analysis by FTIR and NMR. HEMA (26.6 g) was added to the reaction system in 30 min, then 34.47 g of 1,4 butanediol (BDO) was charged into the system in 30 min too. The reaction was kept for 1 hr at 50° C. TIM preblend (ICEM) (64.86 g) was added in 30 min and the reaction was kept further for overnight reaction at 50° C., finally additional 13.06 g of HEMA was added into the system. The reaction was kept in mixing at 50° C. overnight. 0.4 g of BHT was added to the system prior to discharge. Sampling was made for FTIR and NMR. The resin was placed in 45° C. to clear out all the trapped air bubbles. Viscosity of 120 Pa.s @25° C. was resulted.

Modified Genesis resin with K-KAT via Voranol to TMDI Process (V2T)

Dry air was purged through a 1000 mL resin reaction kettle and the jack temperature was set at 50° C. Trimethyl hexamethylene diisocyanate (TMDI) (154.73 g (0.7358 mol) and 0.15 g of urethane catalyst (K-Kat®348, a Bismuth Carboxylate from King Industries) was added to the reaction kettle. Thereafter, Voranol-220-056 (545.77 g, 0.273 mol) was charged into an additional funnel started adding slowly into into the reaction system through 2 hours. Then sample was taken for analysis by FTIR and NMR. HEMA (39.04 g, 0.300 mol) was added to the reaction system in 30 min, then 31.5 (0.35 mol) of 1,4 butanediol (BDO) was charged into the system in 30 min too. The reaction was kept in mixing at 50° C. overnight, then 0.4 g of BHT was added to the system prior to discharge. Sampling was made for FTIR and NMR. The resin was placed in 45° C. to clear out all the trapped air bubbles. Viscosity of 90 Pa.s @25° C. was resulted.

Modified Genesis resin with K-KAT via All-in One Process (All-in-One):

Dry air was purged through a 1000 mL resin reaction kettle and the jack temperature was set at 50° C.Trimethyl hexamethylene diisocyanate (TMDI) (154.73 g (0.7358 mol), Voranol-220-056 (545.95 g, 0.273 mol), HEMA (64.71 g, 0.497 mol), of 1,4 Butanediol (BDO) (34.77, 0.3858 mol) and 0.27 g of urethane catalyst (K-Kat®348, a bismuth carboxylate from King Industries) was added to the reaction kettle. The reaction was kept in mixing at 50° C. overnight, then 0.4 g of BHT was added to the system prior to discharge. Sampling was made for FTIR and NMR. The resin was placed in 45° C. to clear out all the trapped air bubbles. Viscosity of 15 Pa.s @25° C. was resulted.

The composition and properties of the additional polymerizable macromonomers are summarized in Tables 7 to 10.

TABLE 7

| Comparable Examples | Batch Size (grams) | Reaction Sequence (stepwise) | Voranol (grams) (mole) | TMDI (grams) | T-9 (grams) (ppm) | HEMA (grams) (mole) | 1,4-Butanediol (grams) (mole) | ICEM (grams) (mole) | Viscosity @25° C. (Pa · s) |
|---|---|---|---|---|---|---|---|---|---|
| 54 | 800 | TMDI to Voranol | 545.31 (0.2726) | 114.91 (0.5465) | 0.11 (140) | 39.62 (0.3044) | 34.31 (0.3807)) | 64.92 (0.1905) | 35 |
| 55 | 800 | TMDI to Voranol | 545.01 (0.2725) | 114.22 (0.5431) | 0.12 (150) | 26.81 + 13.7 (0.3113) | 34.47 (0.3825) | 65.01 (0.1910) | 55 |

TABLE 7-continued

| Comparable Examples | Batch Size (grams) | Reaction Sequence (stepwise) | Voranol (grams) (mole) | TMDI (grams) | T-9 (grams) (ppm) | HEMA (grams) (mole) | 1,4-Butandiol (grams) (mole) | ICEM (grams) (mole) | Viscosity @25° C. (Pa · s) |
|---|---|---|---|---|---|---|---|---|---|
| 56 | 800 | TMDI to Voranol | 545.86 (0.2729) | 115.2 (0.5478) | 0.81 (1010) | 26.6 + 13.09 (0.3076) | 34.6 (0.3838) | 65.16 (0.1914) | 430 |
| 57 | 800 | TMDI to Voranol | 545.86 (0.2729) | 114.75 (0.5457) | 0.30 (370) | 26.7 + 13.2 (0.3061) | 34.7 (0.3852) | 65.0 (0.1909) | 70 |
| 58 | 800 | TMDI to Voranol | 544.85 (0.2701) | 114.74 (0.5457) | 0.12 (150) | 26.8 + 13.1 (0.3064) | 34.6 (0.3847) | 64.6 (0.1898) | 60 |
| 59 | 800 | TMDI to Voranol | 545.90 (0.2730) | 114.62 (0.5451) | 0.12 (150) | 26.7 + 13.1 (0.3058) | 34.4 (0.3825) | 64.7 (0.1900) | 60 |
| 60 | 800 | TMDI to Voranol | 546.05 (0.2725) | 114.68 (0.5455) | 0.12 (150) | 26.7 + 13.1 (0.3054) | 34.3 (0.3808) | 64.8 (0.1900 | 70 |
| 61 | 800 | TMDI to Voranol | 545.06 (0.2732) | 114.53 (0.5447) | 0.12 (150) | 26.6 + 13.1 (0.3047) | 34.6 (0.3835) | 64.2 (0.1887) | 75 |

TABLE 8

| Reference Examples | Batch Size (grams) | Reaction Sequence (stepwise) | Voranol (grams) (mole) | TMDI (grams) | T-9 (grams) (ppm) | HEMA (grams) (mole) | 1,4-Butandiol (grams) (mole) | ICEM (grams) (mole) | Viscosity @25° C. (Pa · s) |
|---|---|---|---|---|---|---|---|---|---|
| 62 | 800 | Voranol to TMD | 546.23 (0.2731) | 114.87 (0.5463) | 0.11 (140) | 26.97 + 13.4 (0.3102) | 34.59 (0.3838) | 68.2 (0.2003) | 20 |
| 63 | 200 | Voranol to TMD | 136.62 (0.0684) | 28.75 (0.1367) | 0.04 (200) | 6.62 + 3.31 (0.0762) | 8.64 (0.0959) | 16.205 (0.0476) | 10 |
| 64 | 200 | Voranol to TMD | 137.62 (0.0683) | 28.84 (0.1372) | 0.07 (350) | 9.62 (0.0739) | 8.72 (0.0968) | 16.5 (0.0485) | 15 |
| 65 | 200 | Voranol to TMD | 137.32 (0.0687) | 28.7 (0.1365) | 0.06 (300) | 6.72 + 3.57 (0.0791) | 8.98 (0.0996) | 16.34 (0.0480) | 10 |
| 66 | 800 | Voranol to TMD | 545.77 (0.2729) | 114.57 (0.5448) | 0.12 (150) | 26.8 + 13.27 (0.3079) | 34.48 (0.3826) | 65.02 (0.1910) | 10 |
| 67 | 800 | Voranol to TMD | 545.56 (0.2728) | 114.65 (0.5452) | 0.21 (260) | 39.88 (0.3064) | 34.86 (0.3868) | 66.41 (0.1951) | 35 |
| 68 | 800 | Voranol to TMD | 546.14 (0.2731) | 114.8 (0.5459) | 0.30 (380) | 26.7 + 13.16 (0.3060) | 34.65 (0.3845) | 65.12 (0.1913) | 40 |

TABLE 9

| | Batch Size (grams) | Reaction Sequence (stepwise) | Voranol (grams) (mole) | TMDI (grams) | K-KAT348 (grams) (Ppm) | HEMA (grams) (mole) | 1,4-Butandiol (grams) (mole) | ICEM (grams) (mole) | Viscosity @25° C. (Pa · s) |
|---|---|---|---|---|---|---|---|---|---|
| 69 | 800 | All in One-step | 545.96 (0.2730) | 154.73 (0.7358) | 0.2743 (340) | 64.71 (0.4972) | 34.77 (0.3858) | No ICEM | 15 |
| 70 | 800 | TMDI to Voranol | 546.30 (0.2732) | 114.8 (0.5459) | 0.2723 (340) | 26.6 + 13.17 (0.3059) | 34.33 (0.3809) | 64.84 (0.1905) | 140 |
| 71 | 800 | TMDI to Voranol | 546.27 (0.2731) | 114.65 (0.5452) | 0.1393 (170) | 26.6 + 13.13 (0.3057) | 34.47 (0.3825) | 64.86 (0.1905) | 120 |
| 72 | 800 | Voranol to TMDI | 546.4 (0.2732) | 114.57 (0.5448) | 0.1318 (170) | 26.6 + 13.06 (0.3048) | 34.44 (0.3822) | 64.51 (0.1895) | 50 |
| 73 | 800 | TMDI to Voranol | 546.26 (0.2731) | 114.55 (0.5447) | 0.0646 (80) | 26.7 + 13.09 (0.3054) | 34.32 (0.3808) | 64.56 (0.1896) | 45 |
| 74 | 800 | Two-steps | 546.09 (0.2730) | 114.53 (0.5447) | 0.0629 (80) | 39.64 (0.3046) | 34.55 (0.3834) | 64.73 (0.1901) | 35 |

TABLE 9-continued

| Batch Size (grams) | Reaction Sequence (stepwise) | Voranol (grams) (mole) | TMDI (grams) (mole) | K-KAT348 (grams) (Ppm) | HEMA (grams) (mole) | 1,4-Butanediol (grams) (mole) | ICEM (grams) (mole) | Viscosity @25° C. (Pa · s) |
|---|---|---|---|---|---|---|---|---|
| 75 | 786 Voranol to TMDI | 546.04 (0.2730) | 114.72 (0.5455) | 0.1350 (170) | 26.30 (0.2021) | 34.36 (0.3812) | 64.74 (0.1903) | 70 |
| | | | | DABCO: 1,4-Diazabicyclo [2.2.2] octane | | | | |
| 76 | 800 TMDI to Voranol | 546.14 (0.2731) | 114.63 (0.5451) | 0.4943 + 0.4959 (1240) | 26.8 + 13.10 (0.3067) | 34.30 (0.3806) | 64.64 (0.1899) | 10 |

TABLE 10

| Comparable Examples | Batch Size (grams) | Reaction Sequence (stepwise) | Voranol (grams) (mole) | TMDI (grams) (mole) | K-KAT348 (grams) (ppm) | HEMA (grams) (mole) | 1,4-Butanediol (grams) (mole) | ICEM (grams) (mole) | Viscosity @25° C. (Pa · s) |
|---|---|---|---|---|---|---|---|---|---|
| 77 | 800 | TMDI to Voranol | 546.22 0.2731 | 114.85 0.5462 | 0.1316 170 | 26.27 0.2019 | 34.32 0.3808 | 64.57 0.1897 | 80 |
| 78 | 800 | Voranol to TMDI | 545.71 0.2729 | 154.95 0.7369 | 0.1360 170 | 26.20 0.2022 0.4028 | 34.45 0.3823 | No | 135 |
| 79 | 800 | Voranol to TMDI | 545.54 0.2723 | 154.90 0.7366 | 0.1394 170 | 26.17 46.90 0.5615 | 27.08 0.3005 | No | 95 |
| 80 | 800 | Voranol to TMDI | 545.70 0.2730 | 154.89 0.7366 | 0.1377 170 | 39.02 0.2998 | 34.42 0.3819 | No | 90 |
| 81 | 800 | Voranol to TMDI | 545.98 0.2730 | 154.71 0.7357 | 0.1377 170 | 39.05 0.3001 | 31.57 0.3503 | No | 110 |
| 82 | 800 | Voranol to TMDI | 545.77 0.2729 | 154.88 0.7365 | 0.1372 170 | 39.06 0.3001 | 34.41 0.388 | No | 90 |
| 83 | 800 | All in 1-step | 546.05 0.2720 | 154.93 0.7368 | 0.1411 200 | 64.63 0.4966 | 34.79 0.3860 | No ICEM | 13 13 |
| 84 | 800 | V2T + HEMA- DBO 2-step | 545.79 0.2729 | 154.96 0.7369 | 0.1336 170 | 39.04 0.3000 | 34.72 0.3853 | No ICEM | 130 |
| 85 | 800 | IV2T + HEMA- DBO 3-step | 545.79 0.2729 | 154.96 0.7369 | 0.1336 170 | 39.04 0.3000 | 34.72 0.3853 | 65.08 0.1912 | 30 80 |

Example 86

It was unexpectedly discovered that dosing certain amount (10-30% wt/wt) of Resin B with Resin A could effectively improve the mechanical properties (Shore A hardness and tear strength) from such formulated pastes for both light body and heavy body impression materials, see Table 14A. Further increase in load of Resin B in the mixture could not offer any such performance enhancement.

Combo Resins with 90110 or 80/20 of Resin A comprising compounds of the formula (I) without any polysiloxane group and Resin B comprising compounds of the formula (I) according to the present invention, were also prepared by mixing all components of Resin A and Resin B in feed compositions (see Table 11) as part of composition approach to further reduce the reaction rate involved in hydroxyl-terminated siloxane monomer. Indeed moderate temperature raisings of 5° C. in 80/20 combo resin (ZZ2-4) and 9° C. in 90/10 combo resin (ZZ1-208) in comparison to 12° C. in Resin B only were found in such direct synthesis of Resin A and Resin B in 90/10 or 80/20 compositions.

Further, such Combo Resins were formulated (see Table 12) and pastes were made (Table 13) and evaluated (Table 14B), accordingly with the following test methods.

Description of Test Methods

1. Depth of Cure and Shore A Hardness:

Impression material is extruded in a cylindrical mold with 20-mm height and 12-mm inner diameter, and cured from one side for 30 seconds using a blue LED light source with 60±5 mW/cm2 intensity and peak wave length at 460±10 nm. The Depth of Cure is determined by measuring the height of cured specimen after removing the uncured portion. The Shore A Hardness is measured by a durometer on the cross section of cured specimen at 10-mm depth of cure.

2. Compression Set (Recovery) OLD Method:

Impression material is extruded in a cylindrical mold with 10-mm height and 8-mm inner diameter, and cured from one side for 20 seconds using a blue LED light source with 1000±100 mW/cm2 intensity and peak wave length at 460±10 nm. Counting from the time when light curing is completed, the height of the cured specimen is measured at 0'55" (recorded as A). At 1'00", the cured specimen is compressed by 30% (to a height of 7 mm) for 5 seconds, and then allowed to recover under no load. At 3'00", the height of the specimen is measured again (recorded as B). The recovery is calculated as $(1-(A-B)/10) \times 100\%$.

3. Compression Set (Recovery) NEW method:

Impression material is extruded in a cylindrical mold with 20-mm height and 12.5-mm inner diameter, and cured from both sides for 90 seconds (45 seconds each side) using a blue LED light source with 60±5 mW/cm2 intensity and peak wave length at 460±10 nm. Counting from the time when light curing is completed, the height of the cured specimen is measured at 0'55" (recorded as A). At 1'00", the cured specimen is compressed by 30% (to a height of 14 mm) within 1 second, and the deforming force is slowly released over a period of 5 seconds, after which the cured specimen is allowed to recover under no load. At 3'00", the height of the specimen is measured again (recorded as B). The recovery is calculated as $(1-(A-B)/20) \times 100\%$.

4. Tear Strength OLD Method:

Impression material is extruded in a dog bone-shaped mold. The material is cured either for 30 seconds in a halogen light oven such as Triad 2000 (Dentsply Sirona), or for 45 seconds using a blue LED light source with 60±5 mW/cm2 intensity and peak wave length at 460±10 nm. Within 2 hours following curing completion, the specimen is subject to tensile elongation at a crosshead speed of 100 mm/min. The tear strength is determined as the tensile stress at break of the specimen.

5. Tear Strength NEW Method:

Impression material is extruded in a mold in compliance with Die C of ATSM D624—"Standard Test Method for Tear Strength of Conventional Vulcanized Rubber and Thermoplastic Elastomers". The material is cured for 45 seconds using a blue LED light source with 60±5 mW/cm2 intensity and peak wave length at 460±10 nm. Within 2 hours following curing completion, the specimen is subject to tensile elongation at a crosshead speed of 500 mm/min. The tear strength is determined as the ratio between the force at break and the thickness of the specimen at the notch.

The compositions of corresponding activated resins (AL02-170-2) and KR2-11 and the compositions of formulated pastes thereof (AL02-171 and AL02-172, respectively, are shown below. Although paste from 90/10 Combo Resin (ZZ2-208) could offer excellent tear strength, it got lower Shore A hardness in comparison to the paste based on physically blended Resin A and Resin B in same composition, AL02-171 vs AL02-132 in Table 14B.

TABLE 12

Compositions of Activated Combo Resins

| Activated Combo Resin with Resin A and Resin B in 90/10 | AL02-170-2 Dual Initiator Formula % | L171211 Actual gms |
|---|---|---|
| ZZ1-208 | 98.875 | 197.74 |
| CQ | 0.125 | 0.25 |
| Recrystl. EDAB | 0.700 | 1.4 |
| Omnirad 380 | 0.250 | 0.50067 |
| BHT | 0.050 | 0.10947 |
| Total | 100.00 | 200 |
| Activated Combo Resin with Resin A and Resin B in 90/10 | KR2-11 Dual Initiator Formula % | L171212 Actual gms |
| ZZ2-4 | 98.875 | 197.75 |
| CQ | 0.125 | 0.25 |
| Recrystl. EDAB | 0.700 | 1.4 |
| Omnirad 380 | 0.250 | 0.5 |
| BHT | 0.050 | 0.1 |
| Total | 100.00 | 200 |

TABLE 13

Compositions of Formulated Pastes based Combo Resins

| | HEAVY BODY | |
|---|---|---|
| | AL02-171 ZZ1-208 | Lot171212KR |
| Ratio of Resin A and Resin B | % 90/10 | Actual gms |
| Activated Combo Resin AL02-170-2 | 84.27 | 84.28 |
| Ken React LICA 09 | 0.13 | 0.13053 |
| Peppermint | 0.20 | 0.20633 |
| Aerosil 200 | 5 | 5 |
| Sipernat 50 | 10 | 10.05 |
| Corona Magenta Conc.(20%) | 0.4 | 0.40003 |
| Total | 100 | 100.06 |

TABLE 11

Feed Compositions of Combo Resins

| Resin | TMDI (mole) | Voranol 4K (mole) | Voranol 2K (mole) | Silmer (mole) | K-KAT ppm | PEGMA 400 (mole) | C12OH (mole) | Viscosity @25° C. Pa·s | Si Content % wt/wt | MA Content Mmol/g |
|---|---|---|---|---|---|---|---|---|---|---|
| Resin A (ZZ1-182) | 4.69 | 0.94 | 1.87 | 0 | 285 | 4.22 | 0 | 23 | 0 | 0.42 |
| Resin B (ZZ1-181) | 0.50 | 0.10 | 0 | 0.25 | 340 | 0.28 | 0.08 | 12 | 29.1 | 0.32 |
| Combo Resin 90/10 (ZZ1-208) | 0.48 | 0.10 | 0.17 | 0.03 | 325 | 0.42 | 0.01 | 22 | 3.0 | 0.41 |
| Combo Resin 80/20 (ZZ2-4) | 0.49 | 0.10 | 0.15 | 0.06 | 210 | 0.40 | 0.02 | 20 | 5.65 | 0.40 |

TABLE 13-continued

Compositions of Formulated Pastes based Combo Resins

| | HEAVY BODY | |
|---|---|---|
| | AL02-172 | Lot171212KR ZZ2-4 |
| Ratio of Resin A and Resin B | % 80/20 | Actual gms |
| Activated Combo Resin KR2-11 | 84.27 | 84.27 |
| Ken React LICA 09 | 0.13 | 0.13 |
| Peppermint | 0.20 | 0.20095 |
| Aerosil 200 | 5 | 5.02 |
| Sipernat 50 | 10 | 10.01 |
| Corona Magenta Conc.(20%) | 0.4 | 0.4094 |
| Total | 100 | 100.04 |

TABLE 14A

Properties of Formulated Light Curable Heavy Body Pastes based on Mixed Resins

| Heavy Body Paste | Resin A/Resin B Ratio (wt/wt) | Shore A Hardness @10 mm 59 mW/cm$^2$/30" | Depth of Cure 59 mW/cm$^2$/30" (mm) | Tear Strength 100 mm/min 30" in LED (N/mm) | Recovery (%) |
|---|---|---|---|---|---|
| AL05-37-DF | 100/0 | 39.26 (1.6) | 17.94 (0.18) | 2.75 (0.26) | 94.06 (0.1) |
| AL05-72-DF | 90/10 | 63.6 (2.6) | 19.09 (0.1) | 9.77 (0.9) | 98.35 (0.1) |
| AL05-77-1DF | 70/30 | 60.6 (1.4) | 17.68 (0.29) | 7.06 (0.58) | 97.8 (0.1) |
| AL05-77-2DF | 50/50 | 47.5 (0.5) | 15.85 (0.6) | 4.09 (0.2) | 96.98 (0.3) |
| AL05-77-3DF | 30/70 | 18.2 (2.0) | 12.13 (0.4) | 1.47 (0.12) | 96.11 (0.2) |

Note:
The pastes listed in the above table were formulated with 25.3% wt/wt filler mix and specimen were cured by LED curing pad. Tear strength was tested by using new test method (see the details in test method description).

TABLE 14B

Properties of Formulated Light Curable Heavy Body Pastes based on Combo Resins

| HB | TRON Resin Resin A 90% | TRON Resin Resin B 10% | Consistency mm @500 g/30" | Strain Focus 8 mm/20" top only Color 2 min | Shore A@10 mm 59 mW/cm$^2$/30" (w/dist. of 46 mm) | DOC 59 mW/cm$^2$/30" (w/dist. of 46 mm) | Tear Strength 100 mm/min 30" in Triad top only | Compression Set (Recovery) |
|---|---|---|---|---|---|---|---|---|
| AL02-132 | ZZ1-182 | ZZ1-181 | 31 | 19.55 | 42.2 (0.2) 51.0 (1.0) | 15.7 | 319.2 (6.9) | 99.65 |
| AL02-171 | AL02-170-2 w/Combo Resin/ZZ1-208 | | 32.5 | 20.25 | 33.6 (1.3) 31.7 (1.1) | 15.01 | 384.7 (6.5) | 99.35 |
| AL02-172 | KR2-11 w/Combo Resin/ZZ2-4 | | 34 | 20.65 | 21.1 (1.2) 19.9 (0.1) | 11.06 | 300.3 (15.2) | 99.50 |

Note:
The pastes listed in this Table were formulated with 15% wt/wt filler mix and specimen were cured by TRIAD halogen light. Tear strength was tested by using OLD test method (see the details in test method description).

Example: 87

To a 2000 mL flask equipped with mechanical agitator, 1625 g of purchased hydroxyl-terminated siloxane, Silmer OH Di-10 (total acid value as 0.297 mgKOH/g) was added, followed by addition of 168 g of activated basic alumina oxide (~60 mesh). The content was mixed at room temperature for 4-8 h and then allowed to settle overnight, prior to decanting the top clear liquid for further filtration under reduced pressure to remove any solid particles. All clear liquid of 1476 g was collected (91% in yield). Samples were analyzed for total acid value and total moisture content analysis. 0.056 mgKOH/g for total acid value and 1006 ppm for moisture content were resulted.

Additional GC/MS was done for samples with similar treatment and it revealed no allyl alcohol could be detected, see Table 15 for the detailed compositions before & after pretreatment.

As shown in Table 15, treatment of Silmer/lot 11804022 or DMS/lot 3A-2388/aged with molecular sieve only could reduce total moisture content but failed to remove those acidic impurity and good mechanical performance of the formulated compositions from the resulting resin with such molecular sieve-treated Silmer monomer could not be reached. Thus the removal of the acidic impurity is critical to ensure adequate free-radical polymerization to construct the cross-linking network. Activated basic alumina oxide was found to be effective to achieve this goal. Other solid materials with weakly basic property should also work similarly in removing acidic impurities. As depicted in Table 15, we did confirm this by using a microporous ion-exchange resin with weakly basic groups (Amberlyst A21). With Amberlyst A21, an easier filtration process was achieved in comparison to using basic alumina oxide in Silmer treatment.

TABLE 15

Treatment Effect on Composition and Physical Properties of Hydroxyl-terminated Siloxanes from Different Lots and Vendors

| Materials | Treatment Method | pH value, Water-extracted | Acid Value, mg KOH/g | Aldehyde content, ppm | Ally Alcohol content, ppm | Moisture Content, ppm | P/P volatile, % |
|---|---|---|---|---|---|---|---|
| Silmer/lot11801005/aged | As-aged/Untreated | 3.68 | 0.297 | 164 | 522 | 1860 | 8.02 |
| Silmer/lot11801005/aged | 10% Al$_2$O$_3$ + 5% MS (XJ10-198-2) | 4.74 | 0.021 | 166 | 0 | 700 | 6.28 |
| Silmer/lot11801005/aged | 10% Al$_2$O$_3$/5% MS (XJ10-203) | 4.11 | 0.056 | | | 345 | |
| Silmer/lot11801005/aged | 10% Al$_2$O$_3$ (XJ11-5) | | 0.056 | | | 1006 | |
| Silmer/lot11801005/aged | 10% Amberlyst A21/5% MS (XJ11-7) | | 0.037 | | | 2915 | |
| Silmer/lot11804022/new | As-received/Untreated | 3.72 | 0.234 | 195 | 573 | 1350/1574 | 4.38 |
| Silmer/lot11804022/new | 10% Al$_2$O$_3$/5% MS (XJ10-199) | 5.17 | 0.049/0.112 | 181 | 0 | 250/378 | 3.65 |
| Silmer/lot11804022/aged | 5% MS (XJ10-200) | 4.4 | 0.111/0.111 | 178 | 24 | 210/485 | 3.15 |
| Silmer/lot11804022/aged | 10% Al$_2$O$_3$/5% MS (XJ10-202) | 4.67 | 0.056 | | | 686 | |
| Silmer/lot11804022/aged | 5% MS (XJ11-8B) | | 0.056 | | | 627 | |
| Silmer/lot11804022/aged | 10% Al$_2$O$_3$/5% MS/2.5% Amberlyst A21 (XJ11-10) | | | | | | |
| Silmer/lot1171022/aged | As-received/Untreated | n/a | 0.496 | 120 | 4435 | 2540 | |
| Silmer/lot1171022/aged | Aq. acid extracted/Undried(XJ10-194) | n/a | n/a | | 0 | 24 | 6.72 |
| Silmer/lot1171022/aged | vacuum dry @70° C. (XJ10-195) | n/a | 0.527 | 54 | 1582 | 2680 | 5.52 |
| Silmer/lot11701037/aged | As-received/Untreated | n/a | | | | | |
| Silmer/lot11701037/aged | 10% Al$_2$O$_3$/5% MS (XJ10-208) | n/a | 0.056 | | | 820 | |
| DMS/lot3A-2388/aged | As-received/Untreated | 4.49 | 0.036 | | | 1359/1560 | |
| DMS/lot3A-2388/aged | 10% MS (XJ10-201) | 5.47 | 0.056 | | | 386/785 | |
| DMS/lot2L-19956/aged | As-received/Untreated | 3.89 | 0.31 | | | 1404 | |
| DMS/lot2L-19956/aged | 10% Al$_2$O$_3$/5% MS (XJ11-4) | n/a | | | | 906 | |
| KF6000/lot803143/aged | As-received/Untreated | 2.11 | | | | 673 | |
| KF6000/lot803143/aged | 10% Al$_2$O$_3$/5% MS (XJ10-204) | 5.06 | | | | 973 | |

TABLE 16

Treatment Effects on Property and Reactivity of Silmer Monomers and Combo Resin

| Materials | Treatments | pH value water-extracted | Acid value mg KOH/g | Reactivity ΔT(° C.) | Paste's Performance |
|---|---|---|---|---|---|
| Silmer/lot11801005 (new) | As-received | n/a | n/a | 9.8 | Good |
| Silmer/lot11801005 (aged) | As-aged | 3.68 | 0.297/0.278 | 5.5 | Bad |
| Silmer/lot11801005 (aged) | 10% Al$_2$O$_3$ + 5% MS Repeat | 4.11 | 0.056 | 15.7 | Good |
| Silmer/lot11801005 (aged) | 10% Al$_2$O$_3$ Repeat | n/a | 0.056 | 11.3 | Good |
| Silmer/lot11801005 (aged) | 10% Amberlyst A21 | n/a | 0.037 | 4.4 | Good |

TABLE 17

Treatment Effects on Property and Reactivity of Silmer Monomers and Combo Resin

| Materials | Treatments | pH value water-extracted | Acid value mg KOH/g | Reactivity ΔT(° C.) | Paste's Performance |
|---|---|---|---|---|---|
| Silmer/lot11804022 (new) | As-received | 3.72 | 0.234/0.389 | 4.0 | Bad |
| Silmer/lot11804022 (aged) | 5% MS-treated only | 4.40 | 0.110/0.112 | 13.0 | No good |
| Silmer/lot11804022 (aged) | 10% Al$_2$O$_3$ + 5% MS | 5.17 | 0.049 | 12.5 | Good |
| Silmer/lot11804022 (aged) | 10% Al$_2$O$_3$ + 5% MS repeat | 4.67 | 0.056 | 16.1 | Good |
| Silmer/lot11804022 (aged) | 5% Al$_2$O$_3$ only | n/a | 0.056 | 13.0 | Good |

While the present disclosure has been described with reference to one or more embodiments, it will be understood by those skilled in the art that various changes may be made and equivalents may be substituted for elements thereof without departing from the scope of the disclosure. In addition, many modifications may be made to adapt a particular situation or material to the teachings of the disclosure without departing from the essential scope thereof. Therefore, it is intended that the disclosure not be limited to the particular embodiment disclosed as the best mode contemplated for carrying out this disclosure, but that the disclosure will include all embodiments falling within the scope of the appended claims. In addition, all numerical values identified in the detailed description shall be interpreted as though the precise and approximate values are both expressly identified.

The invention claimed is:

1. A light-curable dental impression material having improved shore hardness and improved tear strength, said impression material comprising:
A. a polymerizable polysiloxane resin mixture obtained by a process comprising steps of:
(a) treating an impure diol compound of formula (Xa)

HO-L$^4$(OH)   (Xa)

wherein
L$^4$ is a polysiloxane group of the formula (VIIIa)

wherein
R$^{1\#}$ is an alkylene having 1 to 8 carbon atoms;
R$^{2\#}$ is an alkyl having from 1 to 4 carbon atoms; and
y$^\#$ is an integer from 5 to 20;
with a solid acid absorbent material to obtain purified compound of formula (Xa),
wherein the purified compound of formula Xa has a total acid value of from 0.02-0.06 mg KOH/g,
(b) reacting a mixture comprising:
(i) x equivalents of purified compound of formula (Xa) and one or more di or polyol compounds of the following formula HO—L$^{4''}$(OH)$_{l''}$   (Xa')

wherein
L$^{4''}$ is an (l''+1)-valent linker group; and
l'' is an integer of from 1 to 5,
(ii) y equivalents of one or more compounds of a following formula (XI):

OCN–L$^3$NCO   (XI)

wherein
L$^3$ is a divalent linker group of Formula (VI)

wherein
R$^{a1}$ and R$^{a2}$ which may be a same or different, independently represent a hydrogen atom, a C$_{1-6}$ linear or branched alkyl group, a C$_{4-10}$ aryl group, a polymerizable double bond containing organic residue, a group of the following formula [–X''L'']$_m$R$^{a3}$, wherein X'' represents O, S, or NR$^{a4}$ wherein R$^{a4}$ represents a hydrogen atom, an organic residue containing a polymerizable double bond, a linear or branched C$_{1-6}$ alkyl group, or a C$_{4-10}$ aryl group, L'' represents a C$_{1-6}$ linear or branched alkyl group, a C$_{4-10}$ aryl group, or a SiR$^{a5}{}_2$ group wherein R$^{a5}$ which may be a same or different, independently represent an organic residue containing a polymerizable double bond, or a C$_{1-4}$ alkyl group, m is an integer from 1 to 20, and R$^{a3}$ is an organic residue containing a polymerizable double bond, a C$_{1-4}$ alkyl group, or a C$_{4-10}$ aryl group ; and
(iii) z equivalents of one or more compounds of a following formula (XII):

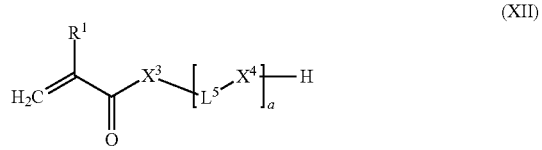

wherein
R$^1$ represents a hydrogen atom or a C$_{1-12}$ alkyl group;
X$^3$ represents an oxygen atom, a sulfur atom or a group NR$^2$, wherein R$^2$ is a hydrogen atom, C$_{1-12}$ alkyl group, or an allyl group;

$L^5$ is a divalent hydrocarbon linker group;
$X^4$ represents an oxygen atom, a sulfur atom or a group $NR^3$, wherein $R^3$ is a hydrogen atom, or a $C_{1-12}$ alkyl group; and
a represents an integer of from 1 to 20,
wherein $0.05 \leq x/y \leq 0.66$,
wherein x, y and z are the molar equivalents of component (a), (b) and (c);
to form the polymerizable polysiloxane resin mixture;

B. a particulate filler; and
C. a photoinitiator.

2. The light-curable dental impression material according to claim 1, wherein $L^{4"}$ is a group formula (VII):

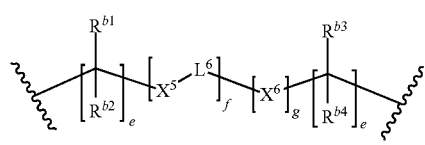

(VII)

wherein
$R^{b1}$, $R^{b2}$, $R^{b3}$ and $R^{b4}$ ; which is a same or different, independently represent a hydrogen atom, a $C_{1-6}$ linear or branched alkyl group, a $C_{4-10}$ aryl group, a polymerizable double bond containing organic residue, a group of the following formula $[-X'''L''']_m R^{b5}$, wherein $X'''$ represents O, S, or $NR^{b6}$ wherein $R^{b6}$ represents a hydrogen atom, an organic residue containing a polymerizable double bond, a linear or branched $C_{1-6}$ alkyl group, or a $C_{4-10}$ aryl group, $L'''$ represents a $C_{1-6}$ linear or branched alkyl group, a $C_{4-10}$ aryl group, or a $SiR^{b7}_2$ group wherein $R^{b7}$ which is a same or different, independently represent an organic residue containing a polymerizable double bond or a $C_{1-4}$ alkyl group, m is an integer from 1 to 20, and $R^{b5}$ is an organic residue containing a polymerizable double bond, a $C_{1-4}$ alkyl group or a $C_{4-10}$ aryl group;
$X^5$ and $X^6$ which is a same or different, and when more than one $X^5$ or $X^6$, are present, the $X^5$ and $X^6$ is the same or different, independently represent an oxygen atom, a sulfur atom and a group $NR^N$, wherein $R^N$ is a hydrogen atom or a $C^{1-4}$ alkyl group;
$L^6$ is a divalent hydrocarbon linker group;
e is an integer of from 1 to 10;
f is an integer of from 1 to 100; and
g is 0 or 1.

3. The light-curable dental impression material according to claim 1, wherein the solid acid-absorbent material is added in an amount of from 1 to 10% wt/wt based on total weight of the impure diol compound of Formula Xa.

4. The light-curable dental impression material according to claim 3, wherein the solid acid-absorbent material removes an active impurity of the impure diol compound of Formula Xa.

5. The light-curable dental impression material according to claim 4, wherein the active impurity of the impure diol compound of Formula Xa is selected from an allyl alcohol, an aldehydes, an acid or a combination thereof.

6. A polymerizable polysiloxane resin mixture obtained by a process comprising steps of:
(a) treating an impure diol compound of formula (Xa)

HO-L⁴(OH)  (Xa)

wherein
$L^4$ is a polysiloxane group of the formula (VIIIa)

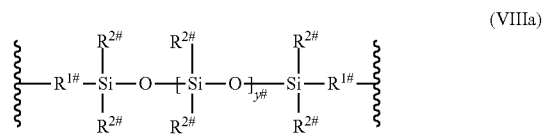

(VIIIa)

wherein
$R^{1\#}$ is an alkylene having 1 to 8 carbon atoms;
$R^{2\#}$ is an alkyl having from 1 to 4 carbon atoms; and
$y^\#$ is an integer from 5 to 20;
with a solid acid absorbent material to obtain purified compound of formula (Xa),
wherein the purified compound of formula Xa has a total acid value of from 0.02-0.06 mg KOH/g,
(b) reacting a mixture comprising:
(i) x equivalents of purified compound of formula (Xa) and one or more di or polyol compounds of the following formula HO-L⁴"(OH)_{l"}  (X)

wherein
$L^{4"}$ is an (l"+1)-valent linker group; and
l" is an integer of from 1 to 5,
(ii) y equivalents of one or more compounds of a following formula (XI):

OCN-L³NCO  (XI)

wherein
$L^3$ is a divalent linker group of Formula (VI)

(VI)

wherein
$R^{a1}$ and $R^{a2}$ which may be a same or different, independently represent a hydrogen atom, a $C_{1-6}$ linear or branched alkyl group, a $C_{4-10}$ aryl group, a polymerizable double bond containing organic residue, a group of the following formula $[-X"L"]_m R^{a3}$, wherein $X"$ represents O, S, or $NR^{a4}$ wherein $R^{a4}$ represents a hydrogen atom, an organic residue containing a polymerizable double bond, a linear or branched $C_{1-6}$ alkyl group, or a $C_{4-10}$ aryl group, L" represents a $C_{1-6}$ linear or branched alkyl group, a $C_{4-10}$ aryl group, or a $SiR^{a5}_2$ group wherein $R^{a5}$ which may be a same or different, independently represent an organic residue containing a polymerizable double bond, or a $C_{1-4}$ alkyl group, m is an integer from 1 to 20, and $R^{a3}$ is an organic residue containing a polymerizable double bond, a $C_{1-4}$ alkyl group, or a $C_{4-10}$ aryl group ; and
(iii) z equivalents of one or more compounds of a following formula (XII):

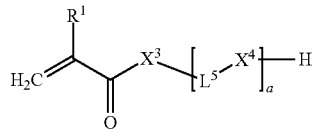 (XII)

wherein
- $R^1$ represents a hydrogen atom or a $C_{1-12}$ alkyl group;
- $X^3$ represents an oxygen atom, a sulfur atom or a group $NR^2$, wherein $R^2$ is a hydrogen atom, $C_{1-12}$ alkyl group, or an allyl group;
- $L^5$ is a divalent hydrocarbon linker group;
- $X^4$ represents an oxygen atom, a sulfur atom or a group $NR^3$, wherein $R^3$ is a hydrogen atom, or a $C_{1-12}$ alkyl group; and
- a represents an integer of from 1 to 20,
- wherein $0.05 \leq x/y \leq 0.66$,
- wherein x, y and z are the molar equivalents of component (a), (b) and (c);
- to form the polymerizable polysiloxane resin mixture for use in a light-curable dental impression material.

* * * * *